US007019131B2

(12) United States Patent
Wong et al.

(10) Patent No.: US 7,019,131 B2
(45) Date of Patent: Mar. 28, 2006

(54) PROGRAMMABLE ONE-POT OLIGOSACCHARIDE SYNTHESIS

(75) Inventors: Chi-Huey Wong, Rancho Santa Fe, CA (US); Zhiyuan Zhang, San Diego, CA (US); Ian Ollmann, Foster City, CA (US); Timor Baasov, Haifa (IL); Xin-Shan Ye, Beijing (CN)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/400,090

(22) Filed: Mar. 25, 2003

(65) Prior Publication Data

US 2004/0024201 A1    Feb. 5, 2004

Related U.S. Application Data

(63) Continuation of application No. 09/762,377, filed as application No. PCT/US99/18151 on Aug. 10, 1999, now Pat. No. 6,538,117.

(60) Provisional application No. 60/096,001, filed on Aug. 10, 1998.

(51) Int. Cl.
*C08B 37/00*     (2006.01)
*G06F 19/00*     (2006.01)
*G01N 31/00*     (2006.01)

(52) U.S. Cl. .................. 536/124; 536/123.1; 536/18.5; 536/18.6; 536/118; 536/17.4; 536/17.5; 536/17.9; 536/4.1; 536/126; 514/53; 435/97; 435/74; 435/75

(58) Field of Classification Search ................ 536/124, 536/123.1, 18.5, 18.6, 118, 77.4, 17.5, 17.9, 536/4.1, 126; 514/53; 435/97, 74, 75
See application file for complete search history.

(56) References Cited

U.S. PATENT DOCUMENTS 6,323,339 B1 * 11/2001 Seeberger et al. .......... 536/124

OTHER PUBLICATIONS

Hanessian, S., "Preparative Carbohydrate Chemistry", 1997, Marcel Dekker, Inc. (New York-Basel-Hong Kong), pp. 313-338.
Takahashi, et al., "Synthetic Study of Oligosaccharide Library Toward Automation-Combinatorial Synthesis and Structure-Activity Relationship of Oligosaccharides having Phytoalexin Elicitor Activity", *Tennen Yuki Kagobutsu Toronkai Koen Yoshishu* 2000, 42, 121-126.

* cited by examiner

*Primary Examiner*—James O. Wilson
*Assistant Examiner*—Devesh Khare
(74) *Attorney, Agent, or Firm*—Donald G. Lewis

(57) ABSTRACT

The reactivity of a number of p-methylphenyl thioglycoside (STol) donors which are either fully protected or have one hydroxyl group exposed has been quantitatively determined by HPLC in conjunction with the development of a broadly applicable approach for a facile one-pot synthesis of oligosaccharides. The influence on reactivity of the structural effects of different monosaccharide cores and different protecting groups on each glycoside donor is characterized and quantified. In addition, a correlation between glycosyl donor reactivity and the chemical shift of the anomeric proton by 1 H NMR has been established. A database of thioglycosides as glycosyl donors has been created using this reactivity data. The utility is demonstrated by the easy and rapid one-pot assembly of various linear and branched oligosaccharide structures. In addition, a computer program as been described for use as a database search tool and guide for the selection of building blocks for the one-pot assembly of a desired oligosaccharide or a library of individual oligosaccharides.

12 Claims, 32 Drawing Sheets

Some Designed building blocks of mannosides with free OH at 2-position

Some Designed building blocks of thiogalactoside

Some Designed building blocks of sialic acid thioglycoside

Both pure α and β anomers

PROGRAMMABLE ONE-POT OLIGOSACCHARIDE SYNTHESIS

TECHNICAL FIELD

The invention relates to synthetic methods for producing oligosaccharides. More particularly, the invention is directed to databases and algorithms employable for optimizing the overall yield of a one-pot synthesis of oligosaccharides.

BACKGROUND

Carbohydrates are ubiquitous in biological systems, involved in such important functions as inflammation (Phillips, M. L. et al. Science 1990, 250, 1130; Lasky, L. A. Science 1992, 258, 964; Giannis, A. Angew. Chem. Int. Ed. Engl. 1994, 33, 178; and Yuen, C.-T. et al. J. Biol. Chem. 1994, 269, 1595), immunological response (Varski, A. Proc. Natl. Acad. Sci. USA 1994, 91, 7390; Ryan, C. A. Proc. Natl. Acad. Sci. USA 1994, 91, 1; and Meldal, M. et al. in Carbohydrate Antigens; (Garegg, P. J. et al., Eds; ACS Symposium Series No. 519; American Chemical Society; Washington, D.C., 1993)), metastasis (Feizi, T. Curr. Opin. Struct. Biol. 1993, 3, 701), and bacterial and viral infection (Varski, A. Glycobiology 1993, 3, 97). While the synthesis of peptides and oligonucleotides was automated decades ago, there are no such general synthetic procedures available for the construction of complex oligosaccharides. Several recent reviews on oligosaccharide synthesis have been published (Paulsen, H. Angew. Chem. Int. Ed. Engl., 1990, 29, 823–839; Banoub, J. Chem Rev. 1992, 92, 1167–1195; Toshima, K. et al. Chem. Rev. 1993, 93, 1503; Schmidt. R. R. et al. Adv. Carbohydr. Chem. Biochem. 1994, 50, 21; and Danishefsky, S. J. et al. Angew. Chem. Int. Ed. Engl., 1996, 35, 1380). The necessity for regio- and stereo-control in glycoside bond forming processes often leads to laborious synthetic transformations, tremendous protecting group manipulations, and tedious intermediate isolations which complicate the overall synthetic process and decrease synthetic efficiency.

In order to facilitate the rapid synthesis of oligosaccharides, a new chemoselective glycosylation strategy, the "one-pot sequential glycosylation," has recently been developed (Fraser-Reid, B. et al. C. Synlett 1992, 927; Raghavan, S. et al. J. Am. Chem. Soc., 1993, 115, 1580; Yamada, H. et al. Tetrahedron Lett., 1994, 35, 3979; Yamada, H. et al. J. Am. Chem. Soc. 1994, 116, 7919; Chenault, H. K. et al. Tetrahedron Lett., 1994, 35, 9145; Ley, S. V. et al. Angew. Chem. Int. Ed. Engl. 1994, 33, 2292; Grice, P. et al. Synlett 1995, 781; Geurtsen, R. et al. J. Org. Chem. 1997, 62, 8145; Grice, P. et al. Chem. Eur. J. 1997, 431). This approach is based on the observation that a large disparity between the reactivities of different glycosyl donors can be achieved simply by varying the protecting groups and the electron donating or withdrawing character of the leaving group within a given class of glycosyl donors (e.g. thioglycosides). As a result, even though identical chemistry is performed at each glycosidic coupling step, with proper planning a high degree of sequence selectivity can be achieved between competing donors of the same class, eliminating the need for protecting group manipulation between coupling steps. The synthetic approach is designed such that the choice of protecting groups on sugar components (ibid, Fraser-Reid, B. et al. 1992; Raghavan, S. et al. 1993; and Yamada, H. et al. 1994), or the combination of protecting groups and anomeric substituent (ibid, Yamada, H. et al. 1994; and Chenault, H. K. et al. 1994) will lead to a decrease in donor reactivity over the course of the synthetic sequence. The most reactive donor is used for the non-reducing end and an unreactive donor is used for the reducing end of the given oligosaccharide target.

Using these procedures, multiple coupling steps were successfully performed by many laboratories to generate various lengths of complex oligosaccharides.(Green, L. et al. Synlett. 1998, 4, 440). This methodology is, however, not generally applicable because of the lack of precise reactivity values of useful glycosyl donors and acceptors. Quantitative analysis of the glycosylation reactivity of several glycosyl donors can been achieved using NMR (Douglas, N. L. et al. J. Chem. Soc. Perkin Trans. 1, 1998, 51). A particularly desirable goal in this research is to establish a generally applicable method that will allow the rapid synthesis of desired oligosaccharides from designed monomeric building blocks in a programmable and predictive manner. Such a method can be used in the rapid assembly of complex oligosaccharides and may be further developed toward automation.

SUMMARY

As a first step towards this goal, we disclose here a general procedure for the quantitative measurement of relative reactivities of various glycosyl donors and acceptors using HPLC. Employing this methodology, up to fifty different donor and acceptor molecules, comprising six different monosaccharide skeletons and eleven commonly used protecting groups, have been evaluated. For each structure, a Relative Reactivity Value (RRV) is determined With this relative reactivity database in hand, we have developed a general computer program compatible with Macintosh computers which can search the database to identify optimal combinations of glycosyl building blocks. This strategy enables the automated design of a rapid, one-pot synthetic protocol for the synthesis of linear and branched oligosaccharides (Scheme 1).

Scheme 1.

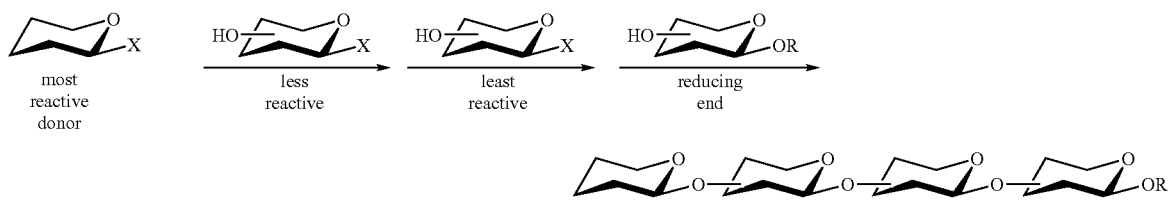

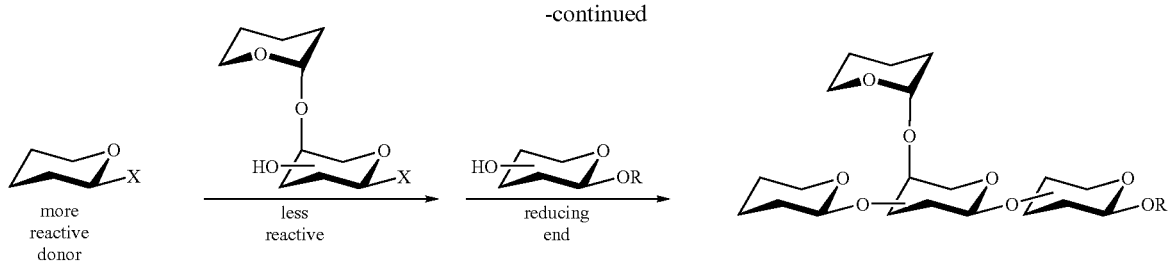

One aspect of the invention is directed to an improved process for synthesizing an oligosaccharide product. The oligosaccharide product is of a type which includes a linear sequence of four or more glycosyl units linked to one another by glycosidic linkages. The sequence starts with a first glycosyl unit at a nonreducing end, concludes with a final glycosyl unit at a reducing end, and includes two or more intermediate glycosyl units sequentially arrayed between the first and final glycosyl units. The process is of a type which includes a condensation of protected glycosyl donors or protected glycosyl donor/acceptors with protected glycosyl donor/acceptors or protected glycosyl acceptors for producing a protected oligosaccharide intermediate. The protected oligosaccharide intermediate is then deprotected for producing the oligosaccharide product. More particularly, the improvement is directed to an additional step wherein a database is provided with regard to the relative reactivity values for variously protected glycosyl donors corresponding to the first glycosyl unit and for variously protected glycosyl donor/acceptors corresponding to each of the intermediate glycosyl units and for variously protected acceptors corresponding to the final glycosyl unit. The variously protected glycosyl donors are of a type which have an activated anomeric carbon and lacking a free hydroxyl; the variously protected glycosyl donor/acceptors are of a type which have both an activated anomeric carbon and one free hydroxyl group; the variously protected acceptors are of a type which have one free hydroxyl group and a blocked anomeric carbon. The improve further includes a step wherein a preferred glycosyl donor is selected corresponding the first glycosyl unit; preferred donor/acceptors are selected corresponding to each of the intermediate glycosyl units; and a preferred acceptor is selected corresponding the final glycosyl unit. The preferred glycosyl donor, each of the preferred glycosyl donor/acceptors, and the preferred acceptor being selected for optimizing condensation reactions leading to the production of the protected oligosaccharide intermediate. In the above condensation step, the preferred glycosyl donor, the preferred donor/acceptors, and the preferred acceptor are added in a sequential fashion under condensation conditions for synthesizing the protected oligosaccharide intermediate in a one-pot synthesis, starting at the nonreducing end and progressing sequentially to the reducing end.

Another aspect of the invention is directed to a process for constructing a database of relative reactivity values for variously protected glycosyl donors, glycosyl donor/acceptors, and glycosyl acceptors. The variously protected glycosyl donors each have an activated anomeric carbon and lacking a free hydroxyl; the variously protected glycosyl donor/acceptors each have both an activated anomeric carbon and one free hydroxyl group; the variously protected acceptors each have one free hydroxyl group and a blocked anomeric carbon. The database is of a type which is employable for optimizing a synthesis of an oligosaccharide product. The process employs a step for determining and storing by electronic storage means the relative reactivity values for the variously protected glycosyl donors, glycosyl donor/acceptors, and glycosyl acceptors.

Another aspect of the invention is directed to a process for selecting a preferred glycosyl donor, preferred glycosyl donor/acceptors, and a preferred glycosyl acceptor for optimizing condensation reactions leading to a one-pot sequential synthesis of a protected oligosaccharide product. The process employs a database of relative reactivity values for variously protected glycosyl donors, glycosyl donor/acceptors, and glycosyl acceptors. The process includes a step for algorithmicly searching the database of relative reactivity values for selecting preferred glycosyl donors, glycosyl donor/acceptors, and glycosyl acceptors employable in a one-pot sequential synthesis with an optimal overall yield for producing the protected oligosaccharide product.

DETAILED DESCRIPTION

Figure 1:
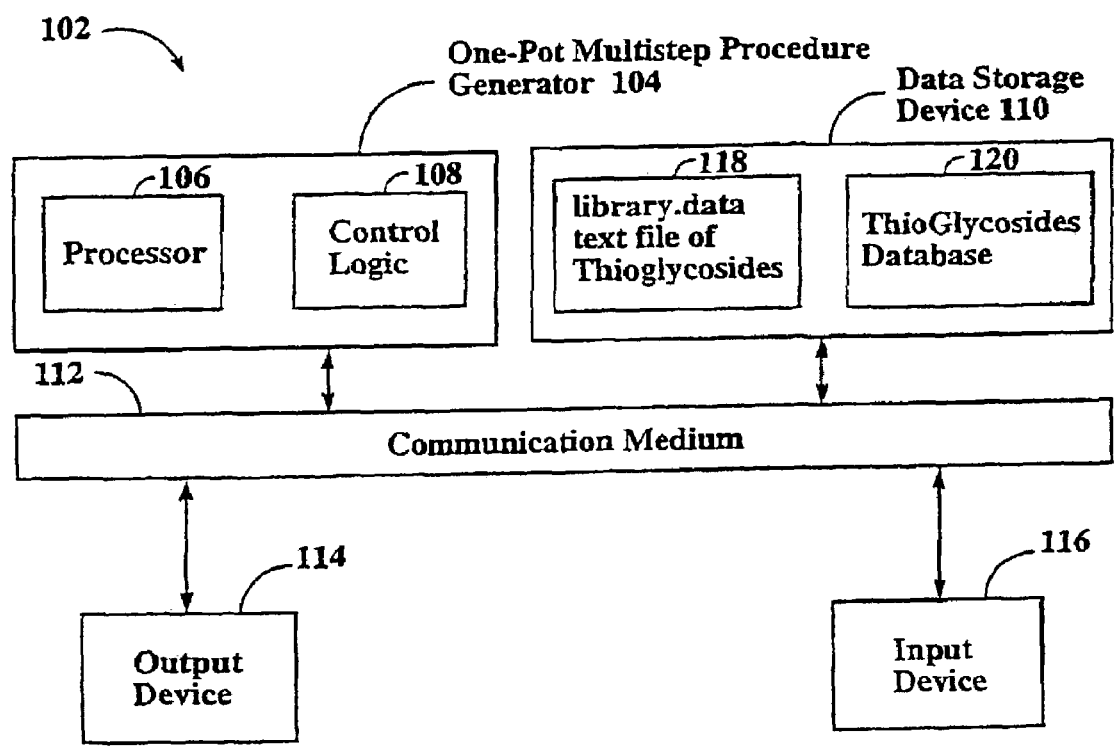
FIG. 1 is a block diagram of the whole system.
Figure 2:
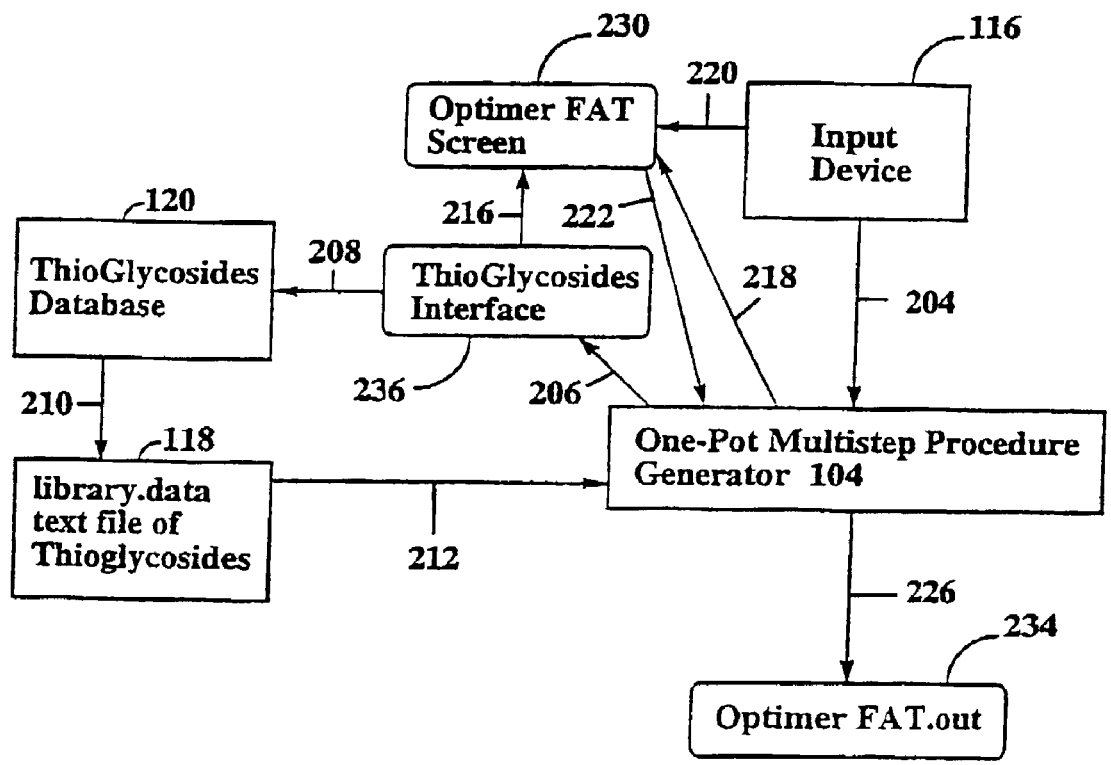
FIG. 2 is a flow diagram depicting the preferred flow of data among the elements of the invention.
Figure 3:
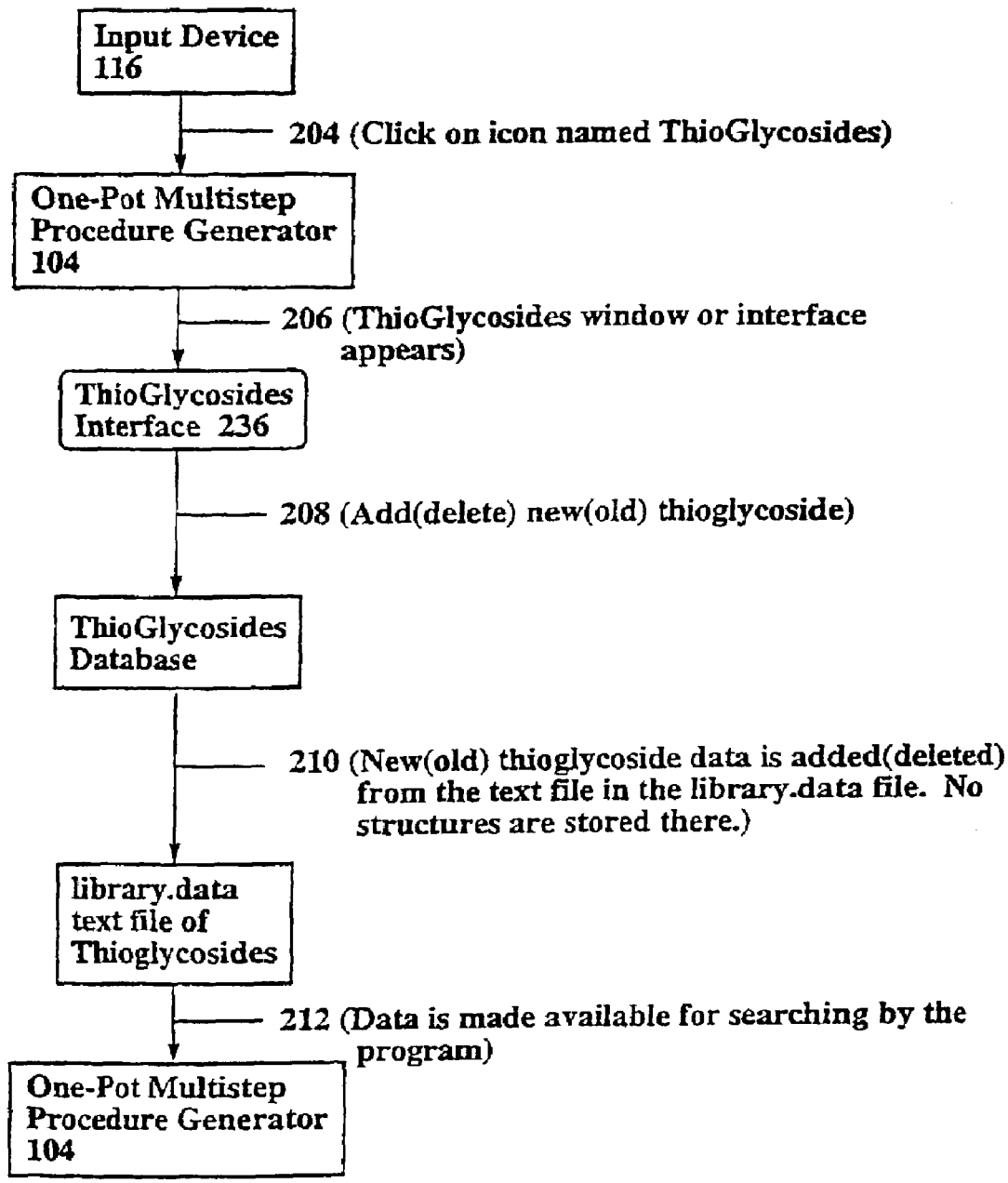
FIG. 3 is a flow chart depicting the preferred operation during addition and deletion of data.
Figure 4:
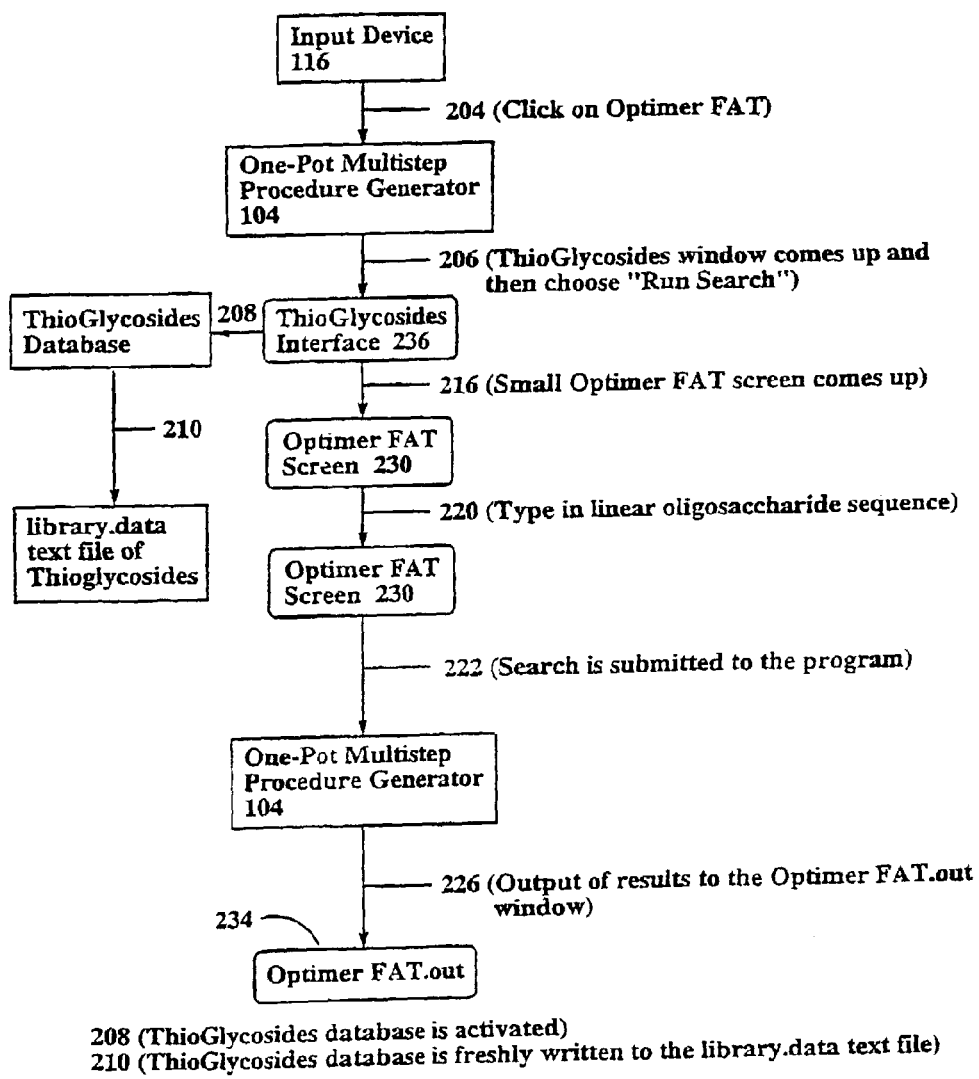
FIG. 4 is a flow chart depicting the preferred operation by choosing a sequence through the ThioGlycosides icon.
Figure 5:
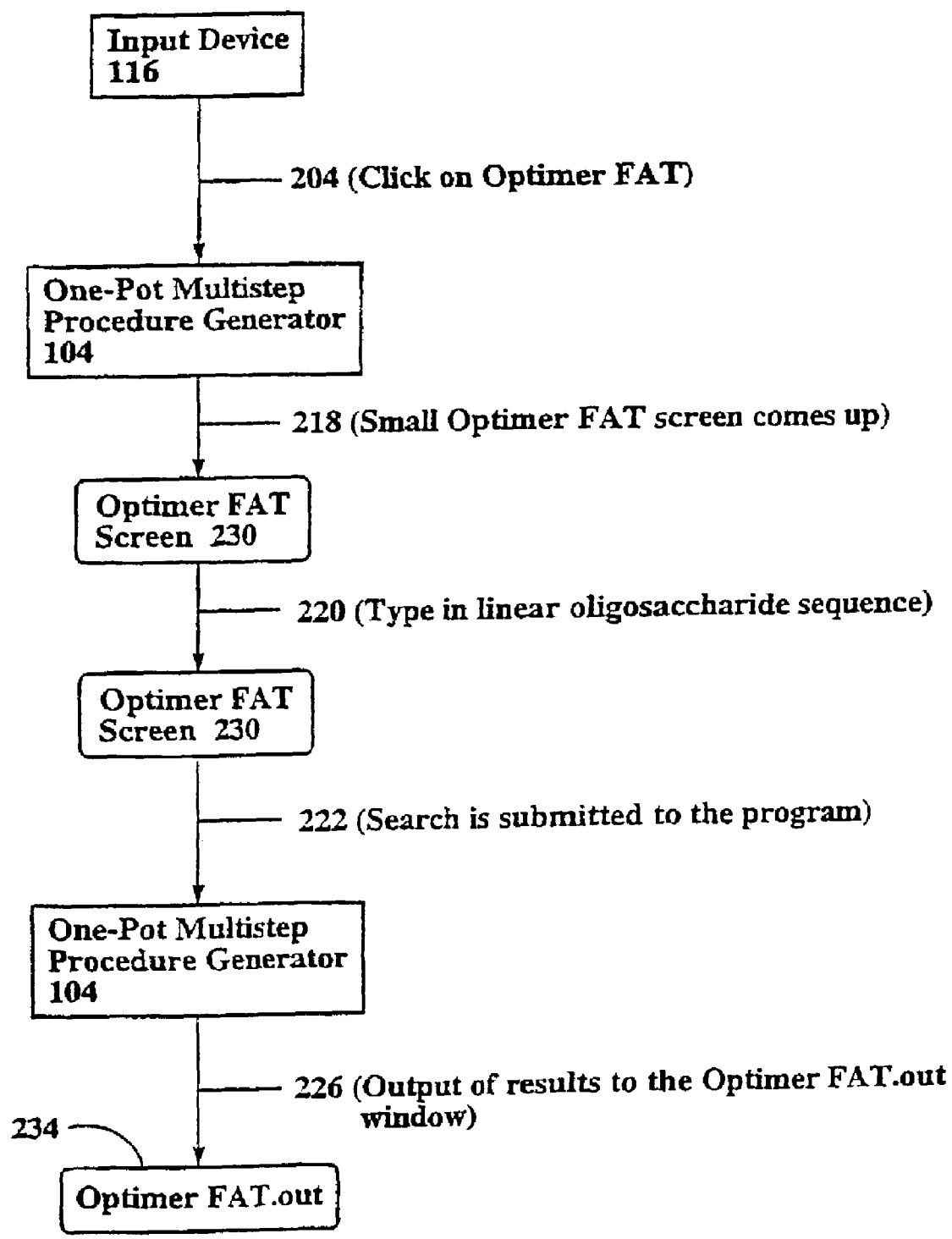
FIG. 5 is a flow chart depicting the preferred operation when choosing a sequence through the Optimer FAT screen directly.
Figure 6:
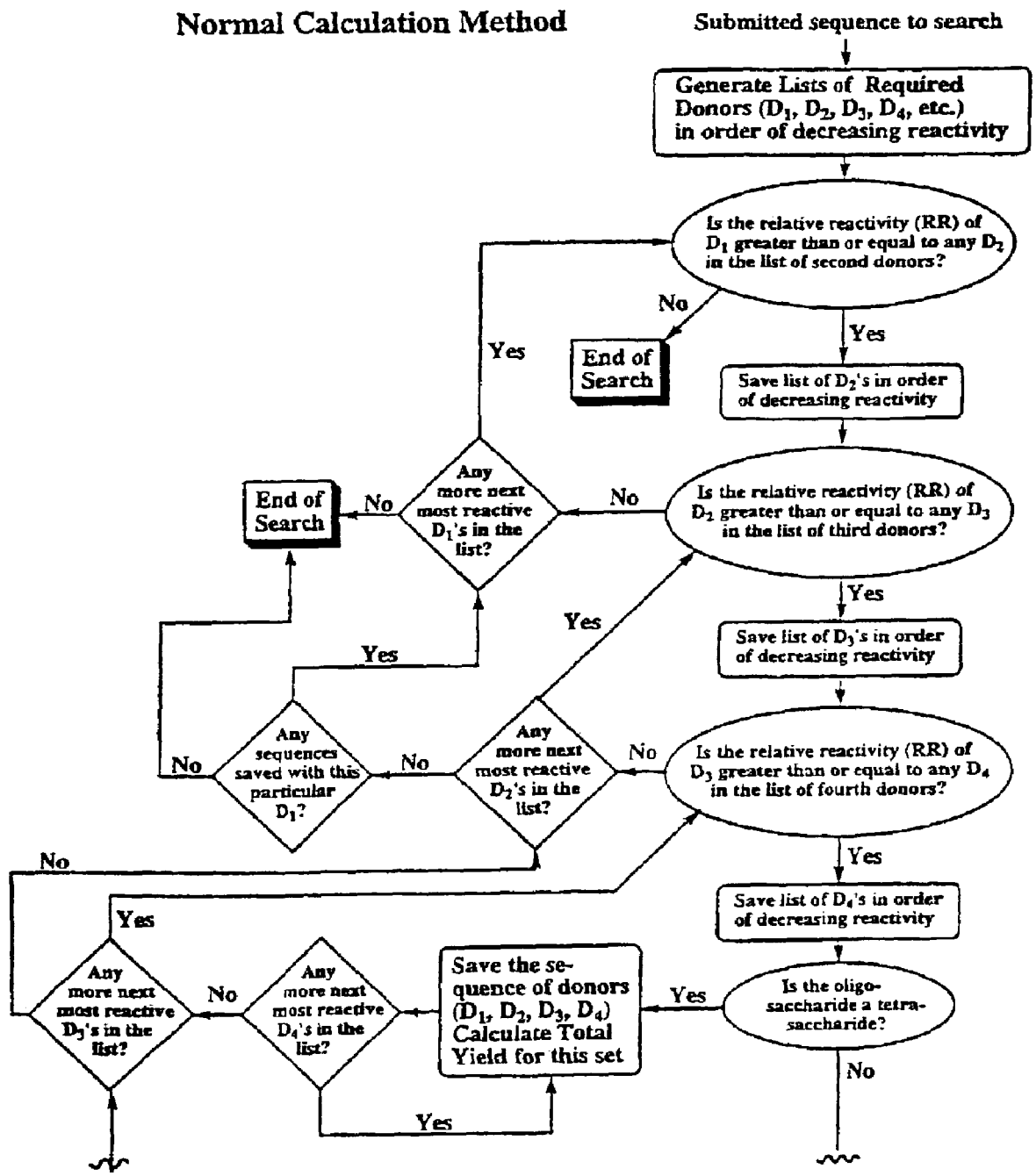
FIG. 6 is the first half of a flow chart depicting the order of events when a sequence is submitted to the program for searching using the normal calculation method or search.
Figure 7:
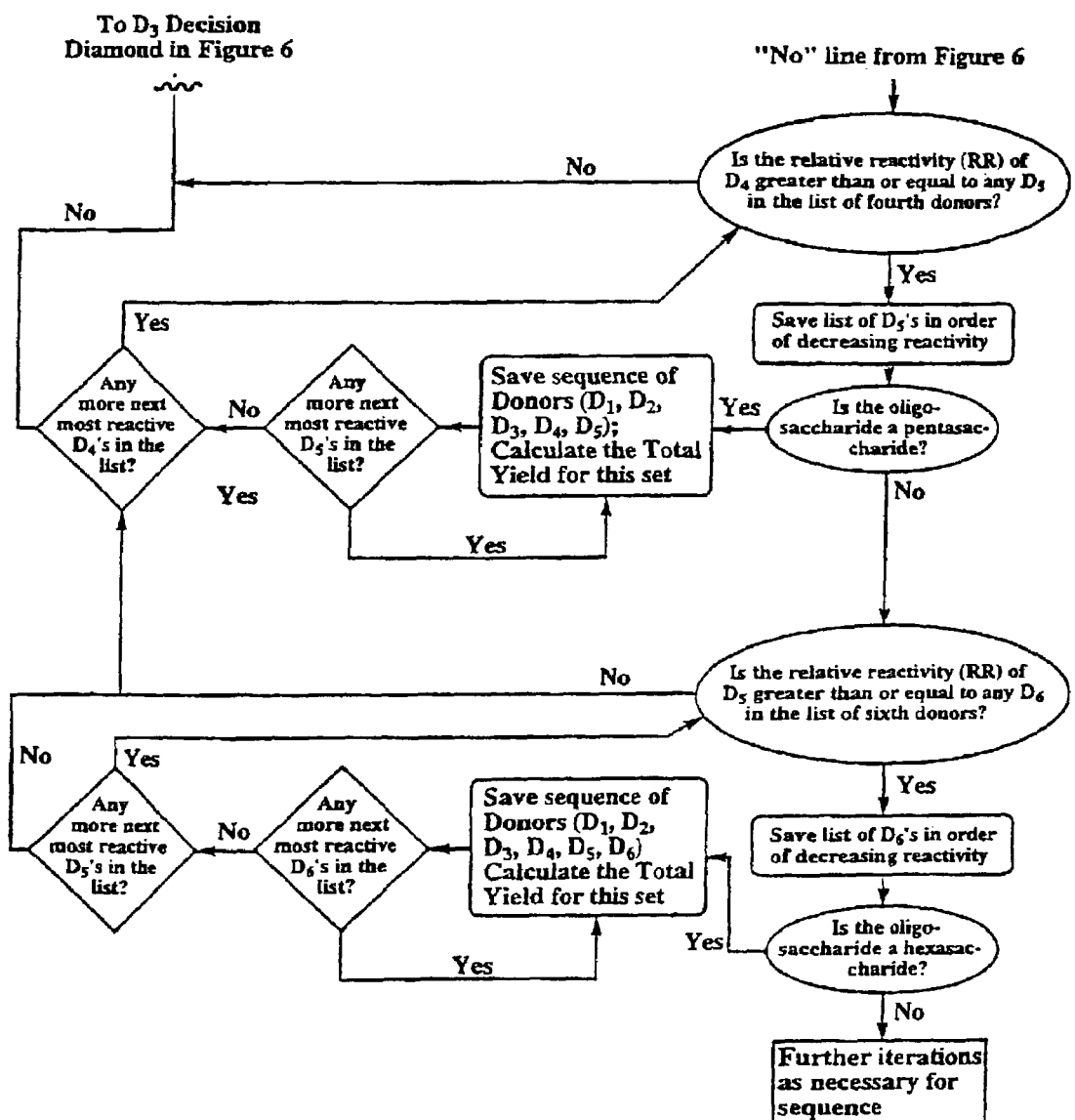
FIG. 7 is the second half of a flow chart depicting the order of events when a sequence is submitted to the program for searching using the normal calculation method or search.
Figure 8:
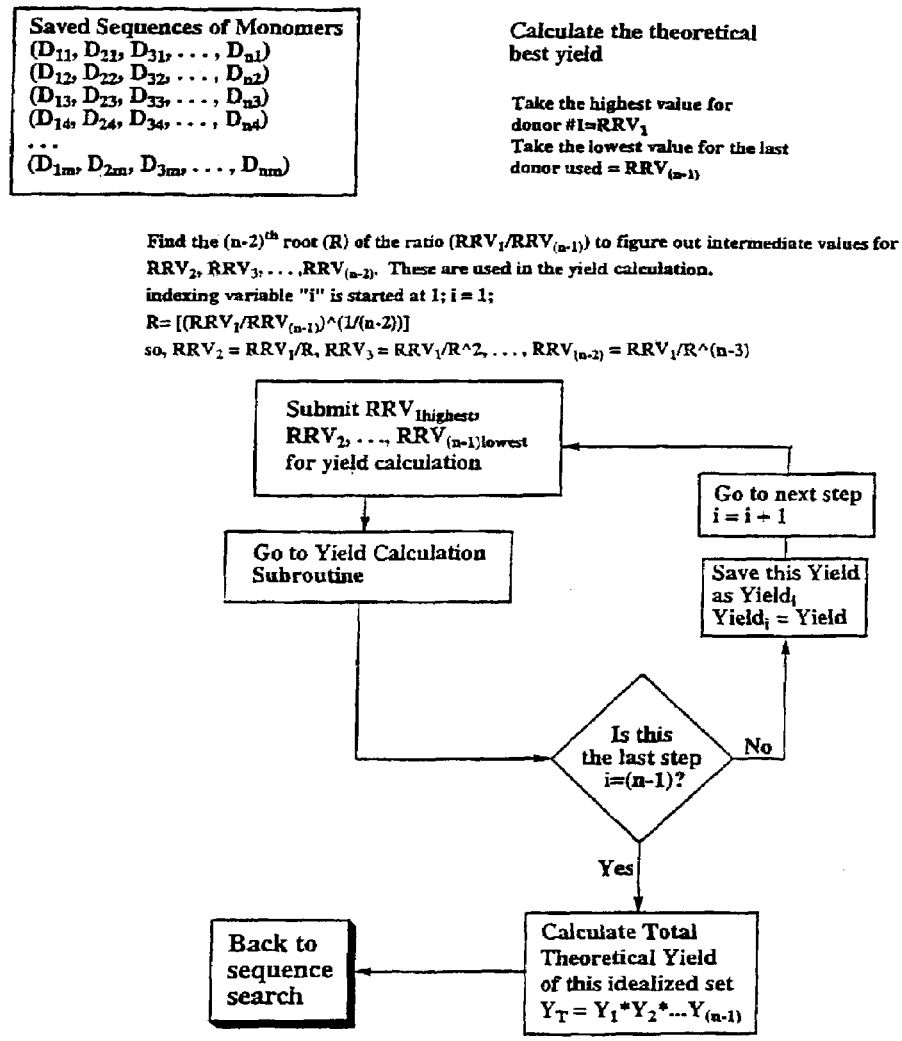
FIG. 8 is a flow chart showing the preferred flow of data when a calculation of best theoretical yield is calculated for the most reactive first monomer and the least reactive last donor/acceptor.
Figure 9:
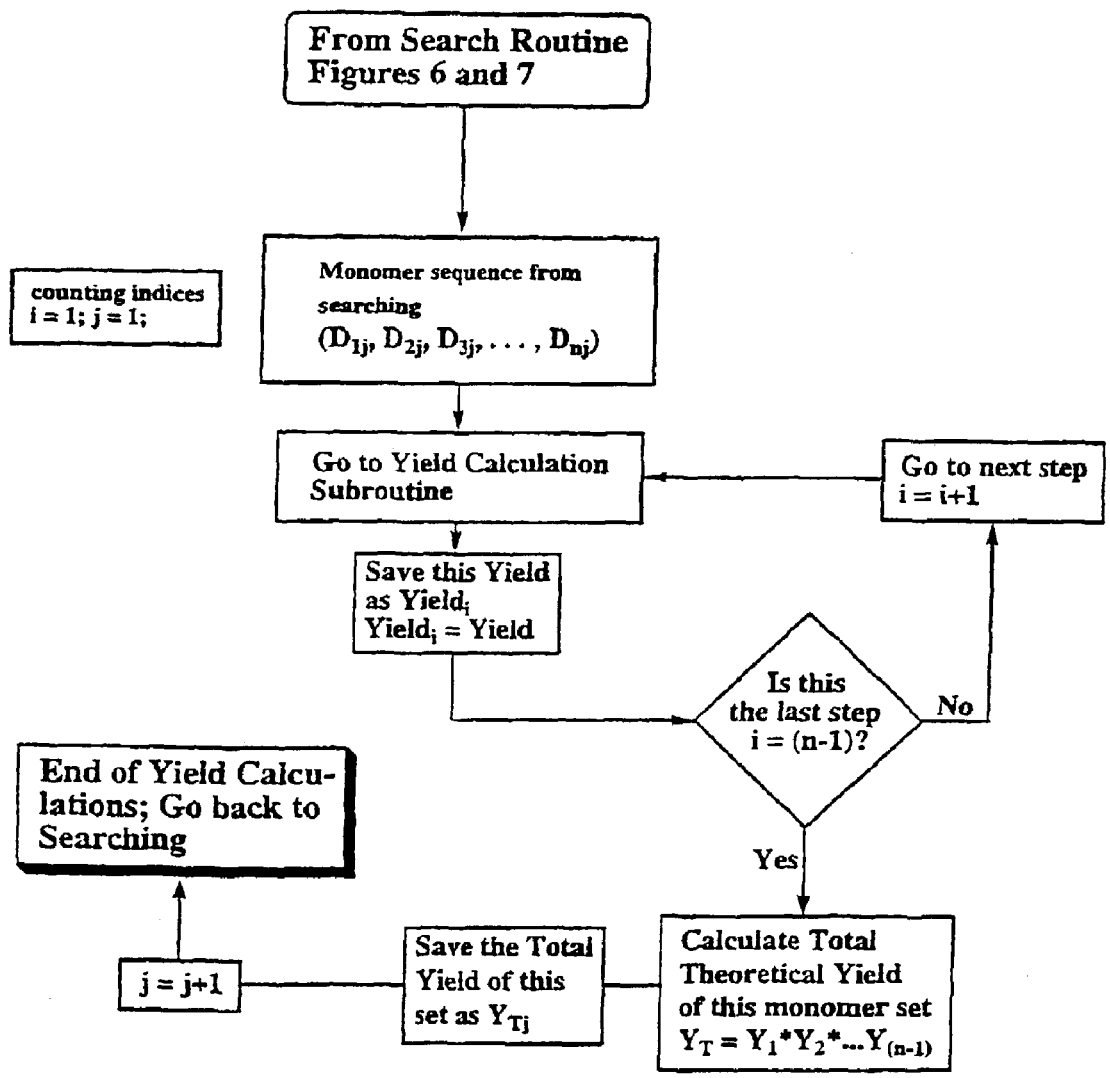
FIG. 9 is a flow chart showing the preferred flow of data when calculating the best theoretical yield possible for the given sequences of monomers.
Figure 10:
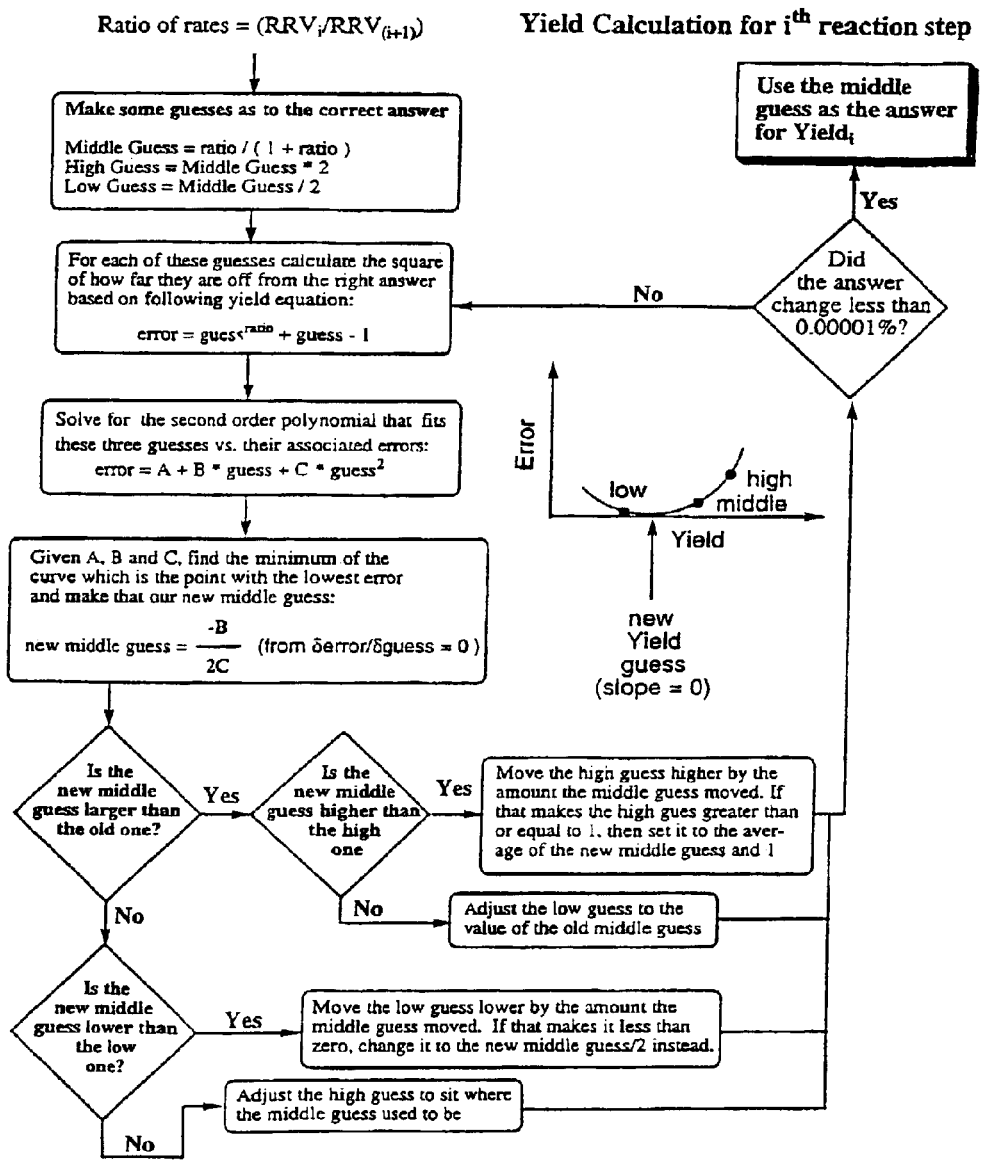
FIG. 10 is a preferred method for calculating the yield of a given step from the relative reactivity ratios of the donor and donor/acceptor in a given step.
Figure 11:
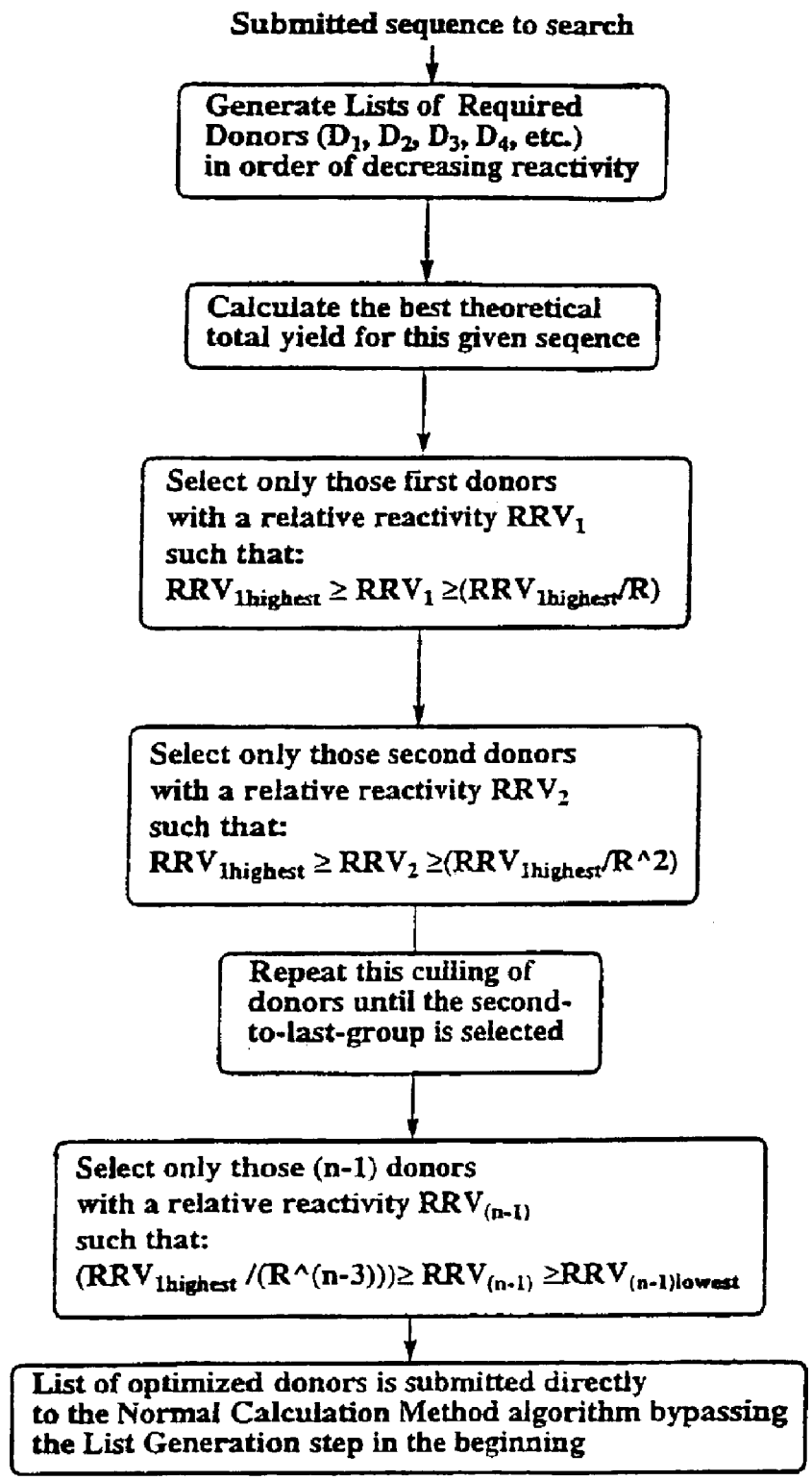
FIG. 11 is the preferred sequence for monomer preselection using the intelligent search.
Figure 12:
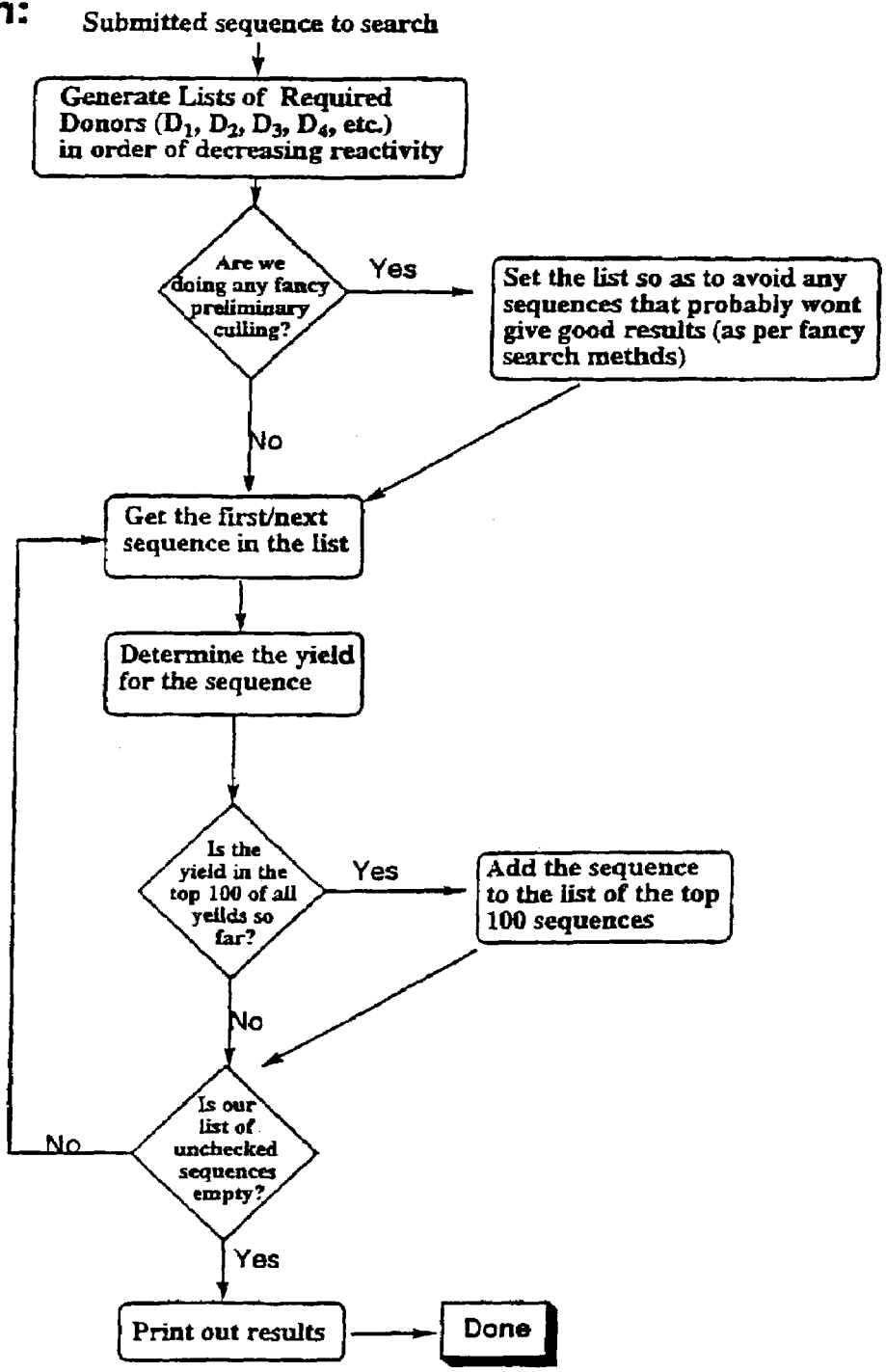
FIG. 12 show the flow diagram for the main search.
Figure 13:
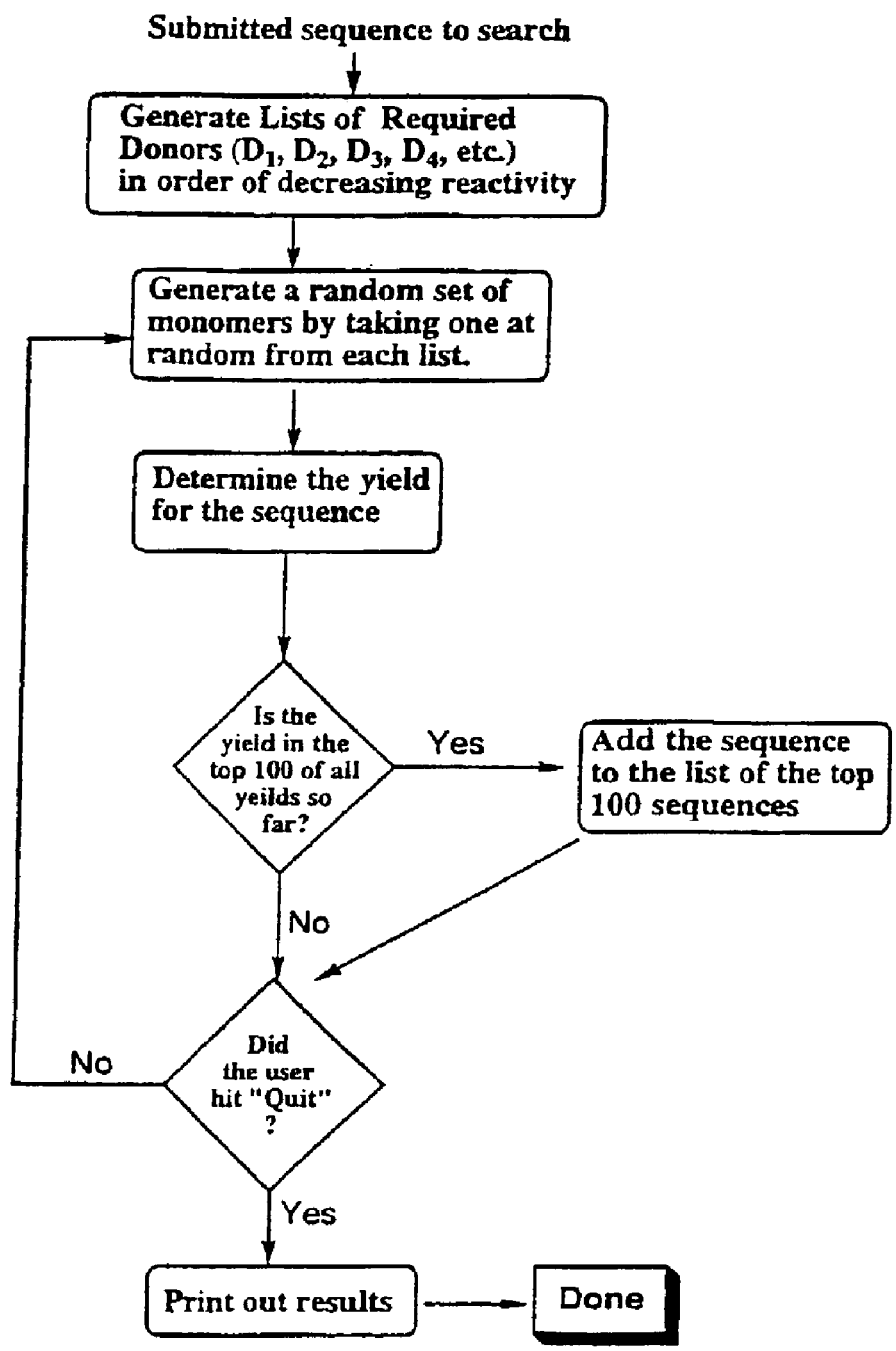
FIG. 13 illustrates the operation during the Monte Carlo search.
Figure 14:
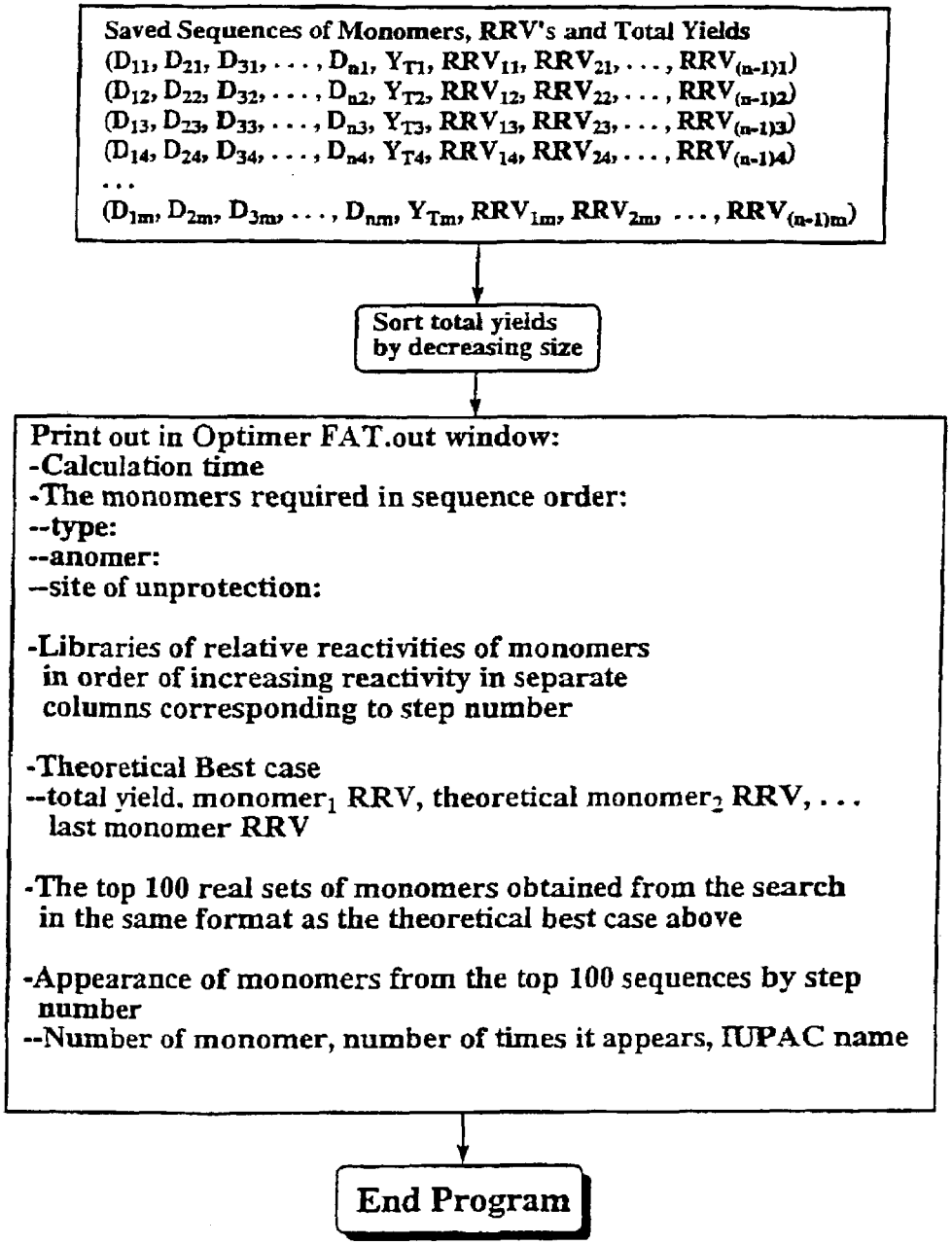
FIG. 14 is a flow chart showing the information obtained by the operation of the program and the form of the printout.
Figure 15:
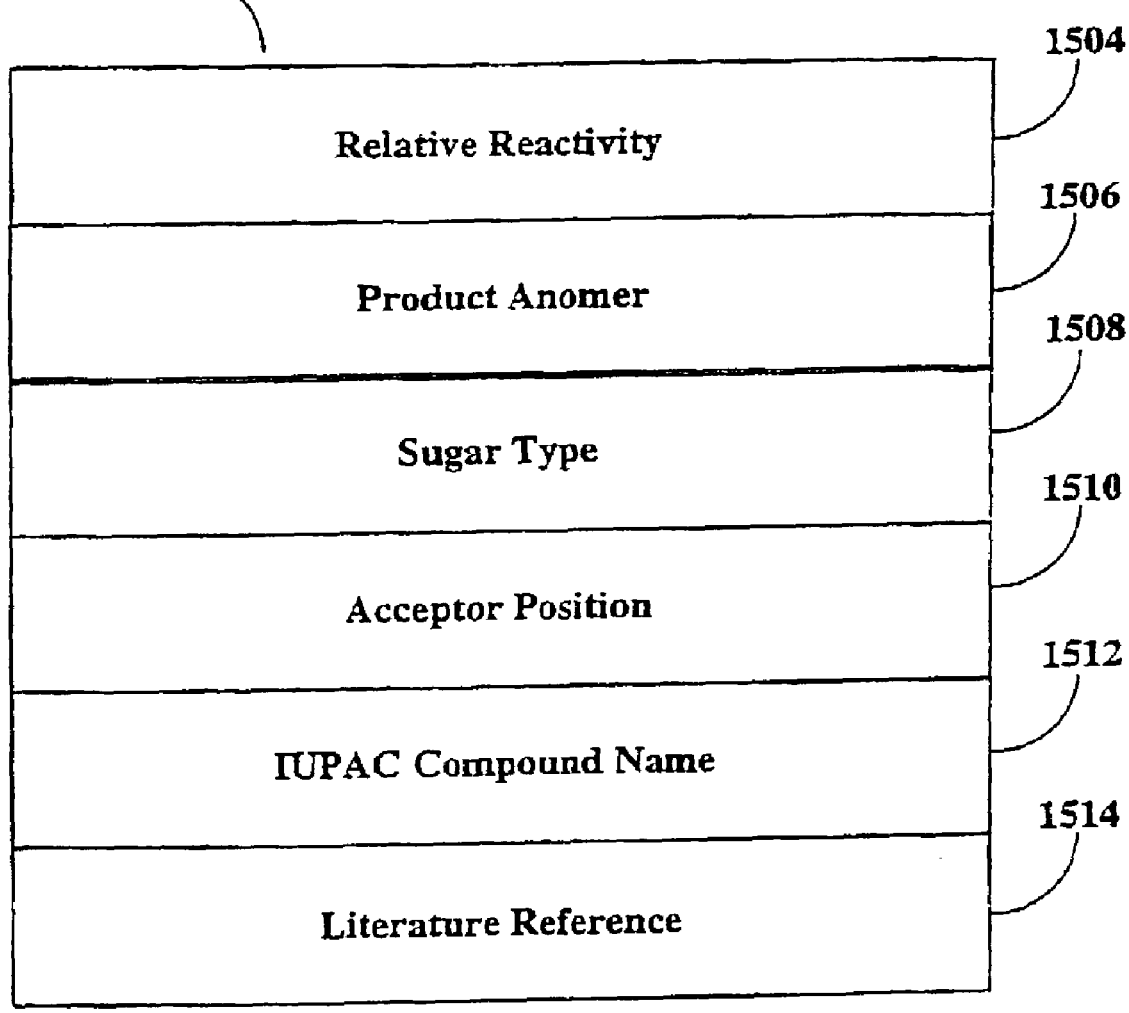
FIG. 15 illustrates a preferred text file record format common to records in the library.data text file.
Figure 16:
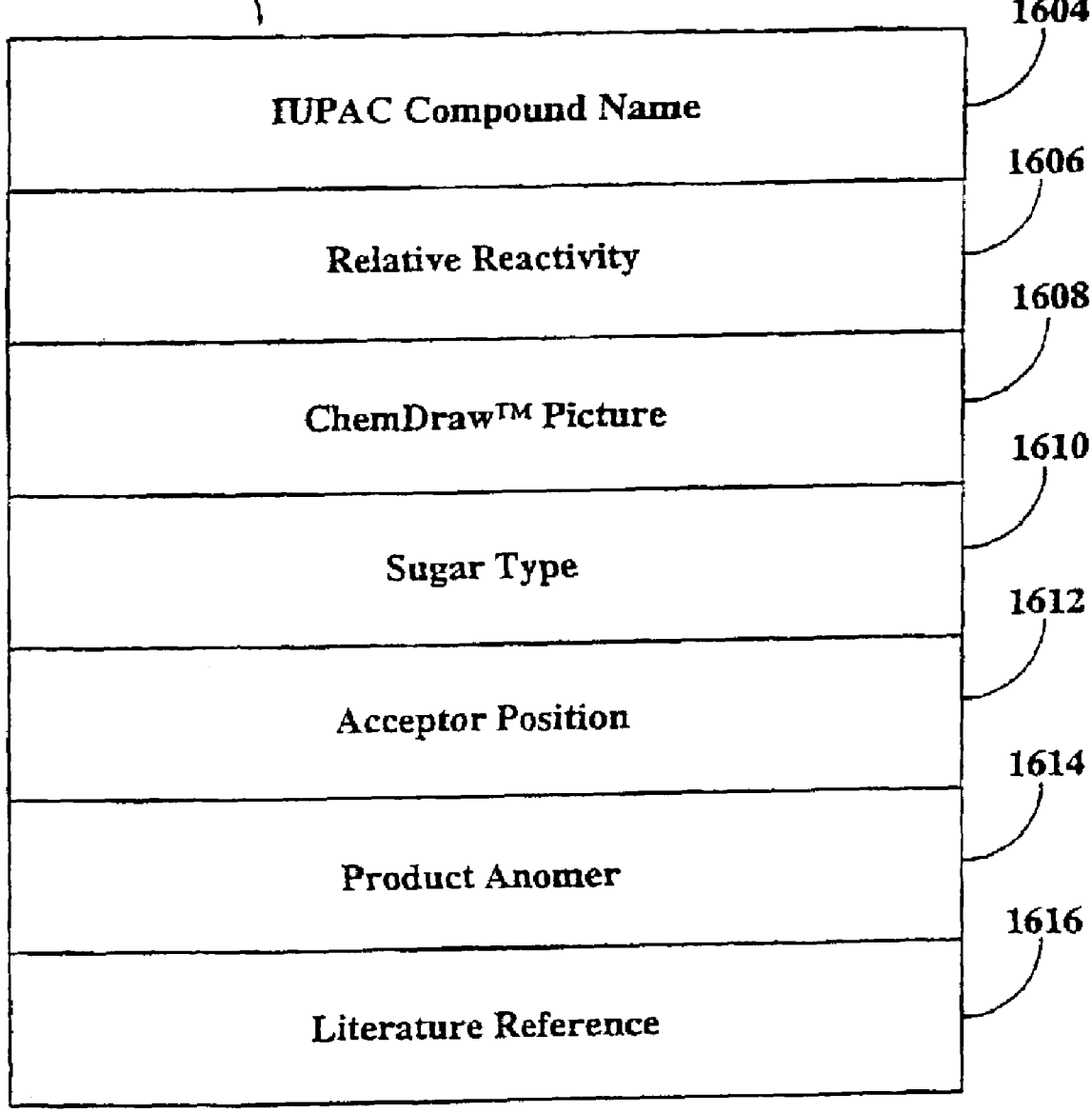
FIG. 16 illustrates a preferred database record format common to records in the ThioGlycosides database.

General Strategy:

As a first step to this investigation, the following questions were examined: 1) what is the best choice of leaving group at the anomeric center of glycosyl donor, 2) what promoter system will be most appropriate for the coupling reaction, which is sufficiently general to handle a wide variety of glycosyl donors and acceptors, 3) what methodology should be used to rapidly and accurately assess the reactivities of different glycosyl donors?

Among the commonly used leaving groups, we chose thioglycosides as "universal building blocks" because they are stable under most reaction conditions frequently used for the construction of building blocks.

The synthesis and application of thioglycosides was recently revied by Garegg, P. J. (Garegg, P. J., *Adv. Carbohydr. Chem. Biochem.* 1997, 52, 179). They can be activated by various conditions such as NIS-TfOH (Konradsson, P. et al. *Tetrahedron Lett.* 1990, 31, 4313; and Veeneman, G. H. et al. J. H. *Tetrahedron Lett.* 1990, 31, 1331), MeOTf (Lonn, H. *Carbohydr. Res.* 1989, 135, 105), DMTST (Fugedi, P. et al. *Carbohydr. Res.* 1986, 149, C9), IDCP (Veeneman, G. H. et al. *Tetrahedron Lett.* 1990, 31, 275), Selectfluor (Burkart, M. D. et al. *J. Am. Chem. Soc.,* 1997, 119, 11743) and other promoters. The characteristic high UV absorbency of p-methylphenylthio (STol) group (for example, for pmethylphenyl mercaptan (Pinkernell, U. et al. Cammann, K. *Anal. Chem.* 1994, 66, 2599) in MeOH at (=256 nm, $\epsilon=5\times10^4$ $M^{-1}$ $cm^{-1}$) facilitates the precise quantification of the reactivities of glycosyl donors. In addition, thiogylcosides with one hydroxy group as acceptor as well as donor are easily prepared and thioglycosides are readily converted to other glycosyl donors commonly used in oligosaccharide synthesis, including sulfoxides (Kahne, D. et al. *J. Am. Chem. Soc.,* 1993, 115, 1580), fluorides, (Mukayama, T. et al. *Chem. Lett.* 1981, 431; Nicolaou, K. C. et al. *J. Am. Chem. Soc.,* 1984, 106, 4189; and ibid, Burkart, M. D. 1997) or halides (Sato, S. et al. *Carbohydr. Res.* 1986, 155, C6-. (b) Anderson, F. O. et al. *Tetrahedron Lett.* 1986, 27, 3919). Finally accessible alternative glycosylation chemistries may later allow for the use of several different donor types in a cooperative fashion as part of an orthogonal coupling strategy (Ito, Y. et al. *J. Am. Chem. Soc.* 1994, 116, 12073). We chose NIS-TfOH as the main promoter for this study. It is a stoichiometric reagent and suitable for a variety of thioglycosides.

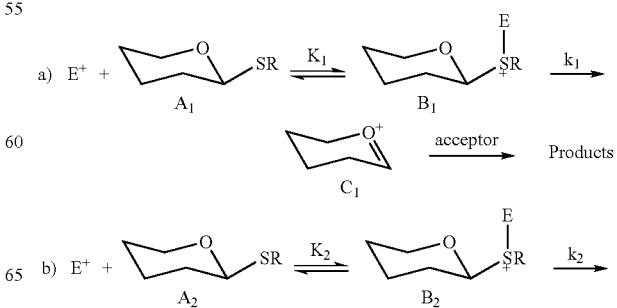

Scheme 2.

Our approach to the quantification of glycosyl donor reactivities is based on earlier works by Sinnot (Sinnott, M. L, *Chem. Rev.*, 1990, 90, 1171) and Fraser-Reid (Fraser-Reid, B. et al. *J. Org. Chem.* 1990, 55, 6068), which employ a competition reaction between two donors to determine the relative rates of reactivity between them. The overall competition reaction is thought to proceed as shown in Scheme 2. Two glycosyl donors $A_1$ and $A_2$ are forced to compete in a reversible fashion for a common electrophile ($E^+$), forming activated intermediates $B_1$ and $B_2$. These intermediates may collapse to the corresponding transient oxocarbenium cations $C_1$ and $C_2$, which then rapidly react with the acceptor molecule to give the products. Assuming the rate determining step is the step B (C, then the overall reaction can be described by an apparent second-order rate constant, rate=$k_{obs}[E^+][A]$. This is related to the first-order rate equation (rate=k [C]) by the relation, $k_{obs}$=k/K. Our measured rate constants, $k_{obs}$ are relative second-order rate constants, not absolute quantities. Measuring the rates as relative values allows us to escape rate constant dependence on the identity of the activator. To the extent that B(C remains the rate-determining step and the mechanism is the same, this should help ensure that the relative rates measured here will remain useful for many different activators and perhaps other donor types as well. This analysis is also true for glycosyl donors with neighboring group participation which occurs after the rate-determining step.

Figure 17:
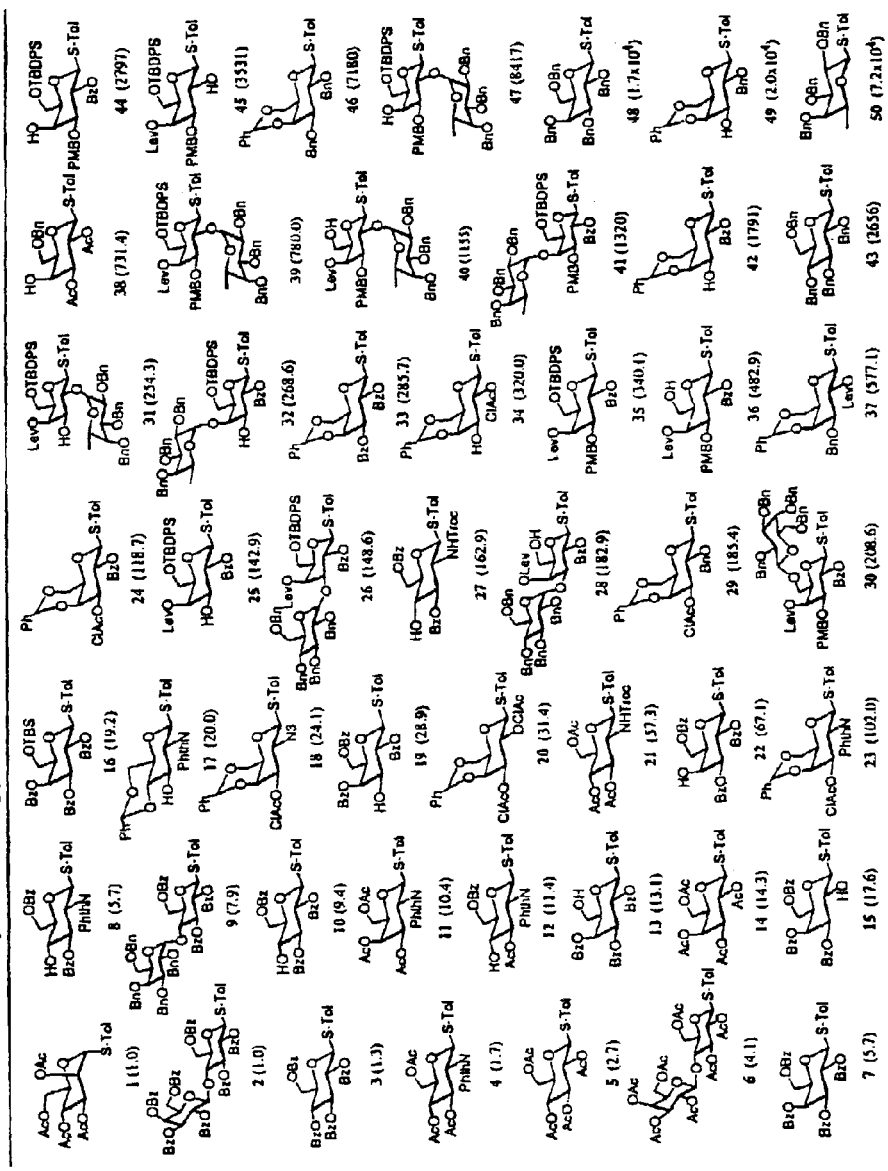
FIG. 17 illustrates a table of relative Reactivity Values of various thioglycosides. The table was constructed on the basis of the manner shown in Chart 1. The relative reactivity value (RRV) of the most unreactive compound, acetylated mannoside, was defined as 1.0. Compounds are numbered as the decreased reactivity trend, and the RRV/s are shown in parentheses.

Construction of the General Reactivity Database:

The table of FIG. 17 was constructed by comparison of reactivities between the various glycosyl donors and a small set of reference compounds (7, 14, 33 and 48). The relative reactivities between the four reference compounds were also examined. Based on these data, the relative reactivities of all 50 compounds were quickly determined through simple multiplication of the relative rate constant ratios with the reference compounds. Since these values are relative, they are normalized such that the least reactive donor in the library has a reactivity of 1.0 (Chart 1).

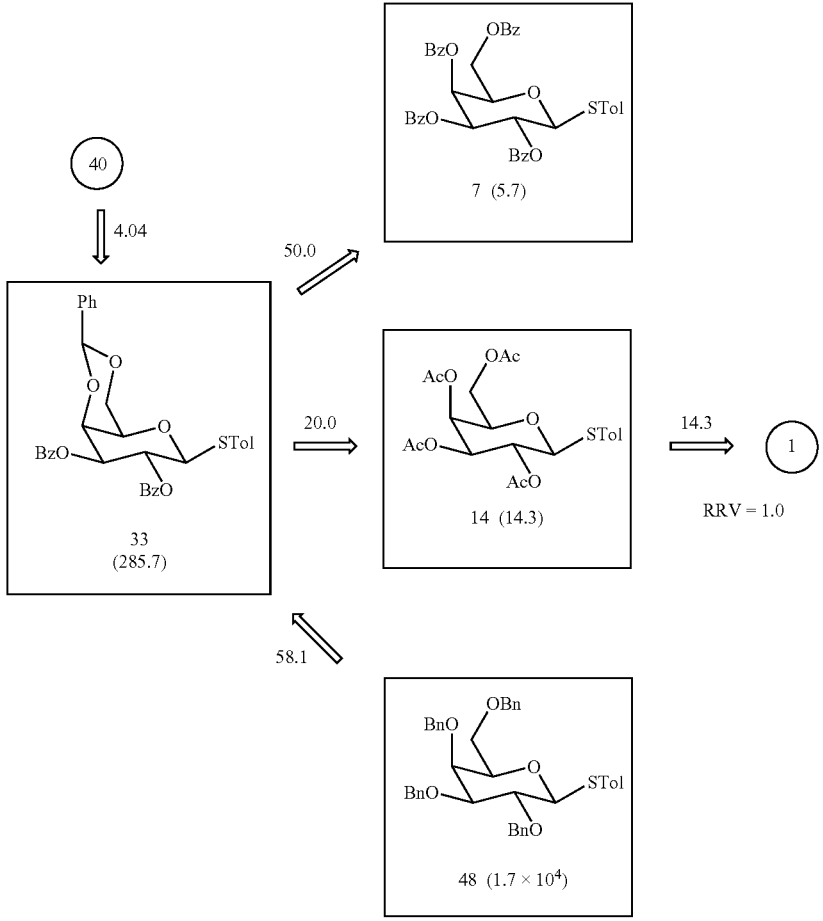

Chart 1.

RRV (40) = 4.04 × 20.0 × 14.3 = 1155

The individual RRV's which were used to make the table were determined by a direct competition assay. Unlike the previous works (ibid, Dougpls, N. L. 1998), however, we did not directly obtain relative rate ratios from ratios of product formation. While it is possible to directly measure a relative first-order rate constant by a competition assay between two donors using a large excess of reagents A over activator $E^+$ (Scheme 2) such that the donor (A) concentrations do not change appreciably over the course of the reaction, these methods did not immediately lend themselves to HPLC analysis in our case. Since we followed the reaction by disappearance of the donor rather than appearance of product (see experimental section), arranging the experiment so that pseudo-first order kinetics are observed is relatively different.

equiv. of thioglycoside within certain time. For the competition reactions, the conditions were exactly the same as with NIS-TfOH (see general procedure in experimental section), except that DMTST was taken as 2-mole equiv. relative to the donors (each 1-mole equiv.) and the reaction time was continued for 3 h. This measurement can only be performed between donors with small reactivity difference.) These preliminary results suggest that different promoters do not dramatically affect the relative reactivities of glycosyl donors. Thus, the RRV's in the table of FIG. 17 may also be applicable to other promoters as well. We have taken advantage of this fact, employing DMTST in a one-pot oligosaccharide synthesis (see One-Pot OligoSaccharide Synthesis below) as a solution to the problem of by-product participation in the glycosylation reaction when NIS is used as an activator.

TABLE 2

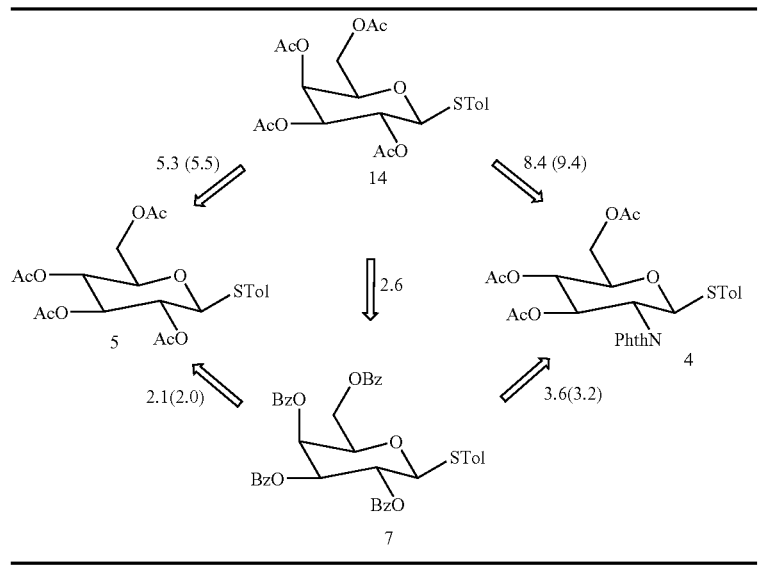

Figure 21:
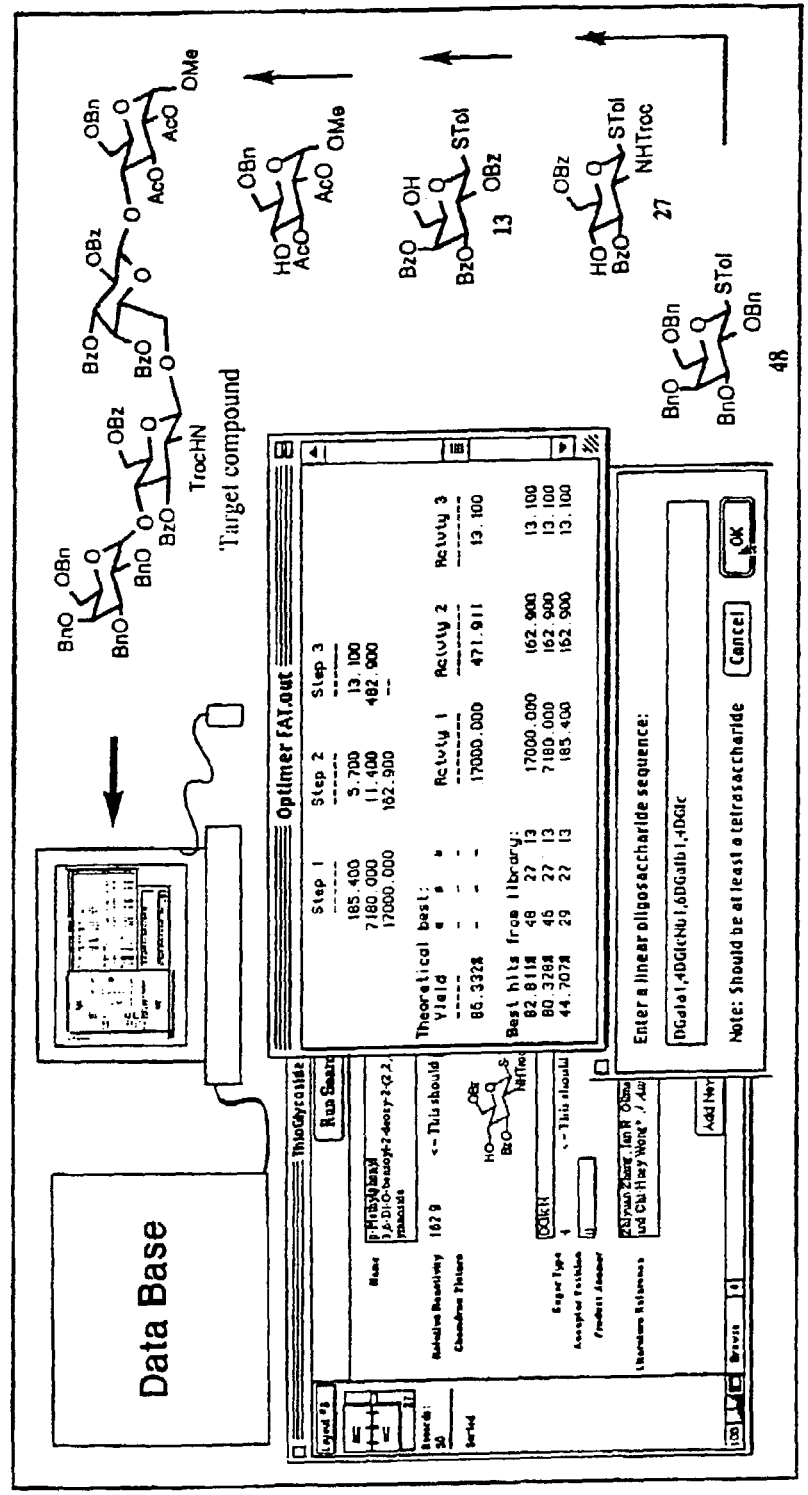
FIG. 21 illustrates the relationship between expected yield and the rate ratios between the donor and acceptor.
Figure 22:
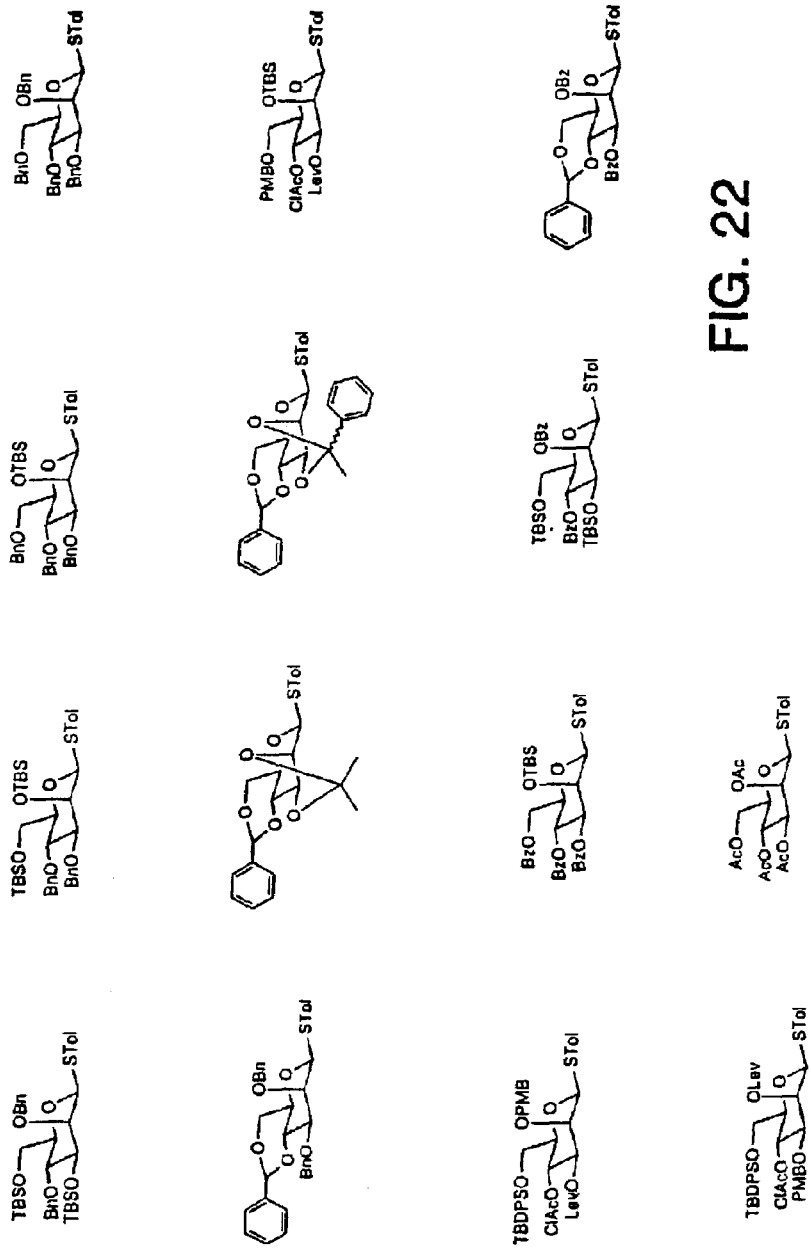
FIG. 22 illustrates some designed building blocks of fully protected mannosides.
Figure 23:
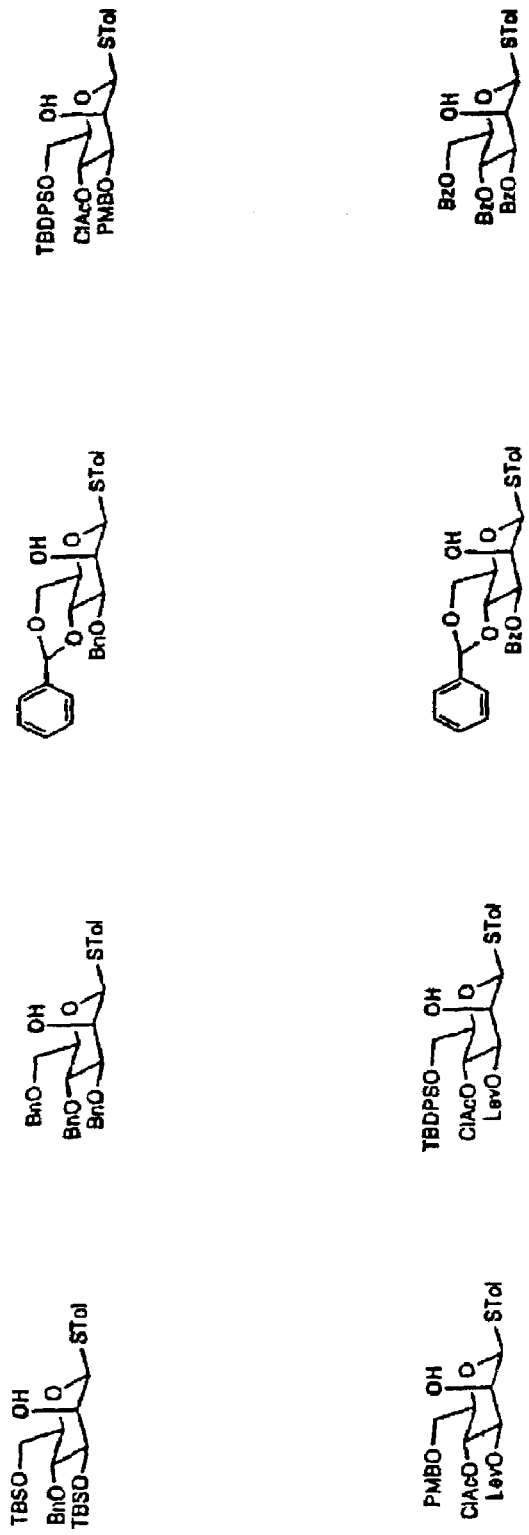
FIG. 23 illustrates some designed building blocks of mannosides with free OH at 2 position.
Figure 24:
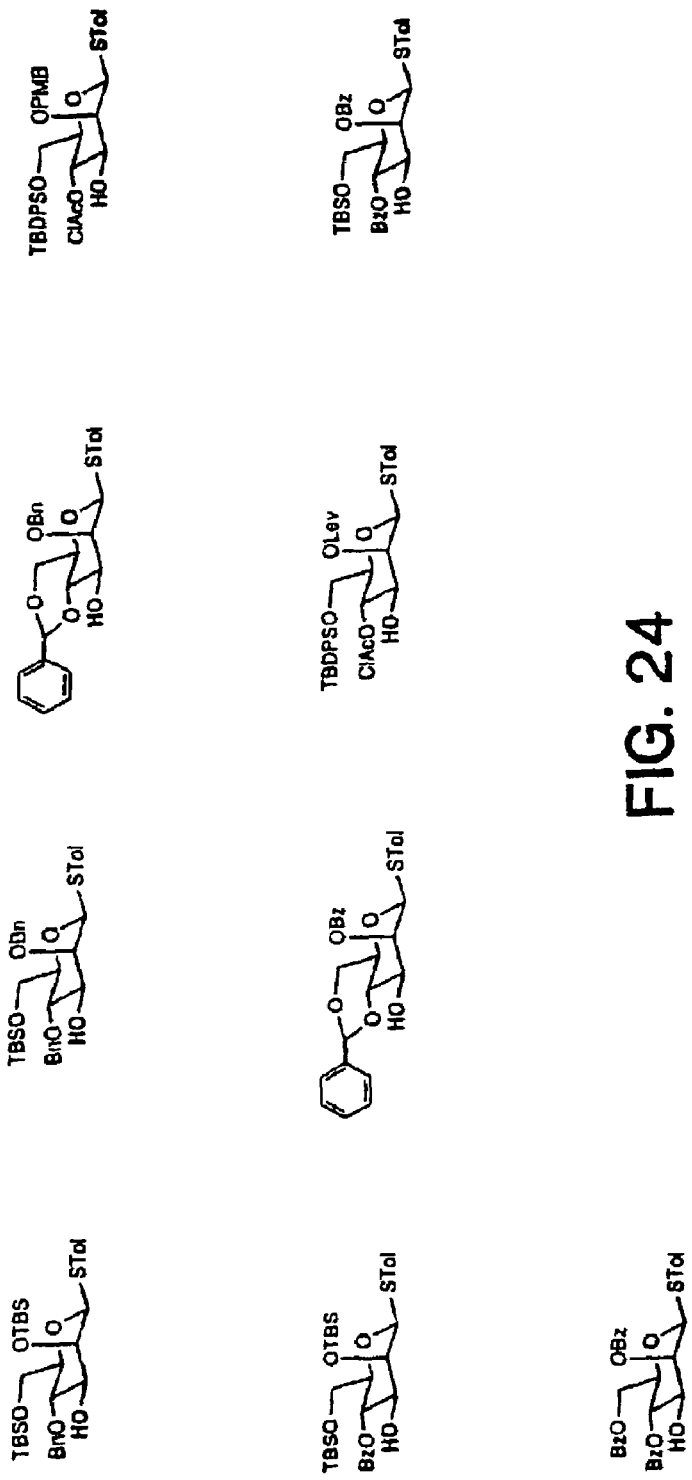
FIG. 24 illustrates some designed building blocks of mannosides with free OH at 3 position.
Figure 25:
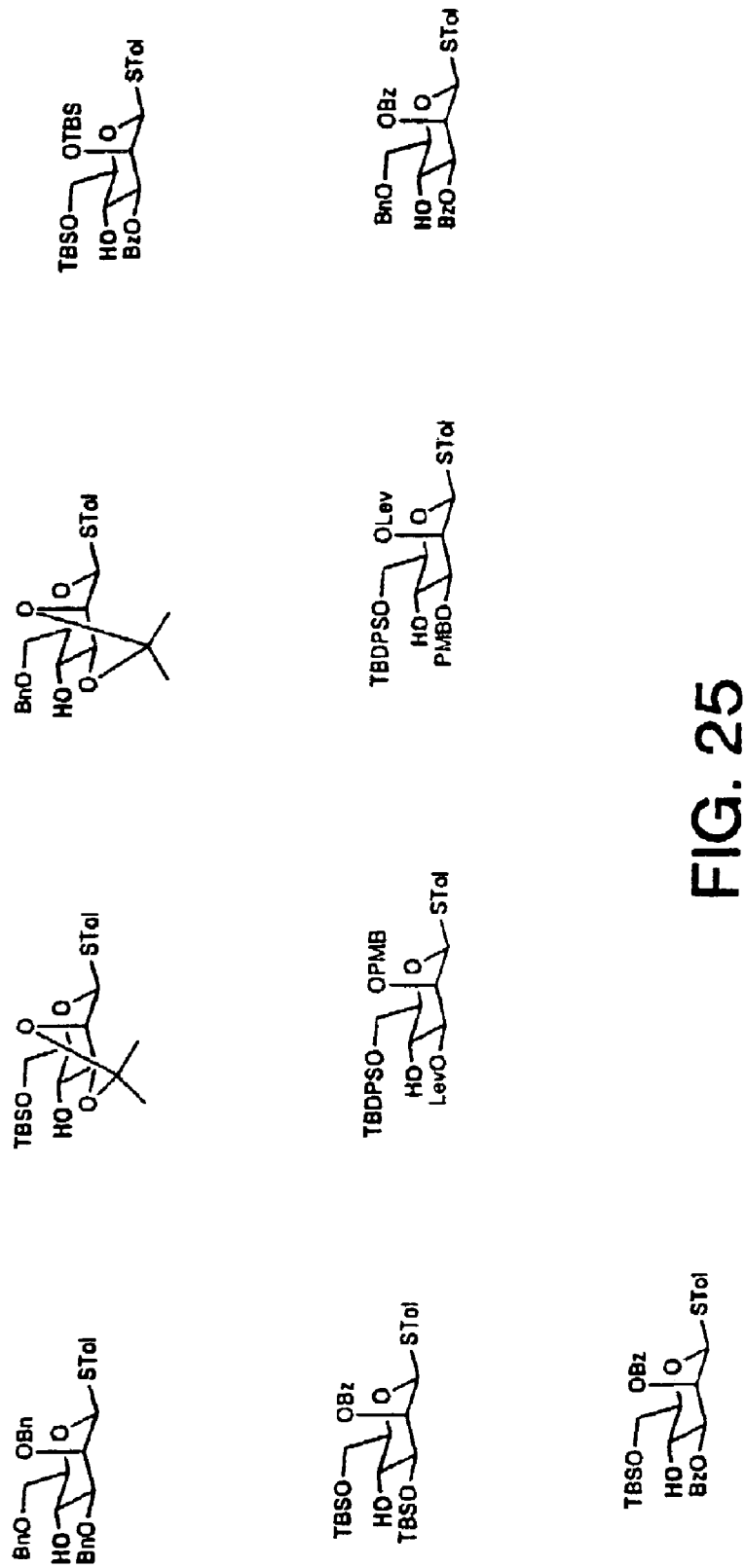
FIG. 25 illustrates some designed building blocks of mannosides with free OH at 4 position.
Figure 26:
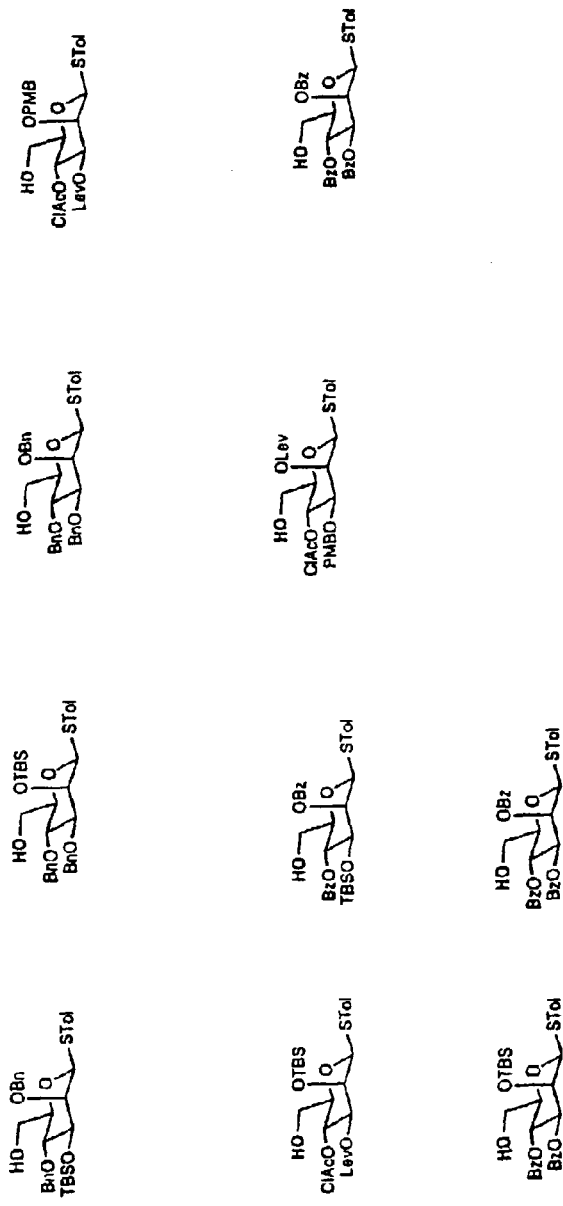
FIG. 26 illustrates some designed building blocks of mannosides with free OH at 6 position.
Figure 27:
FIG. 27 illustrates some designed building blocks of mannosides with two OH groups.
Figure 28:
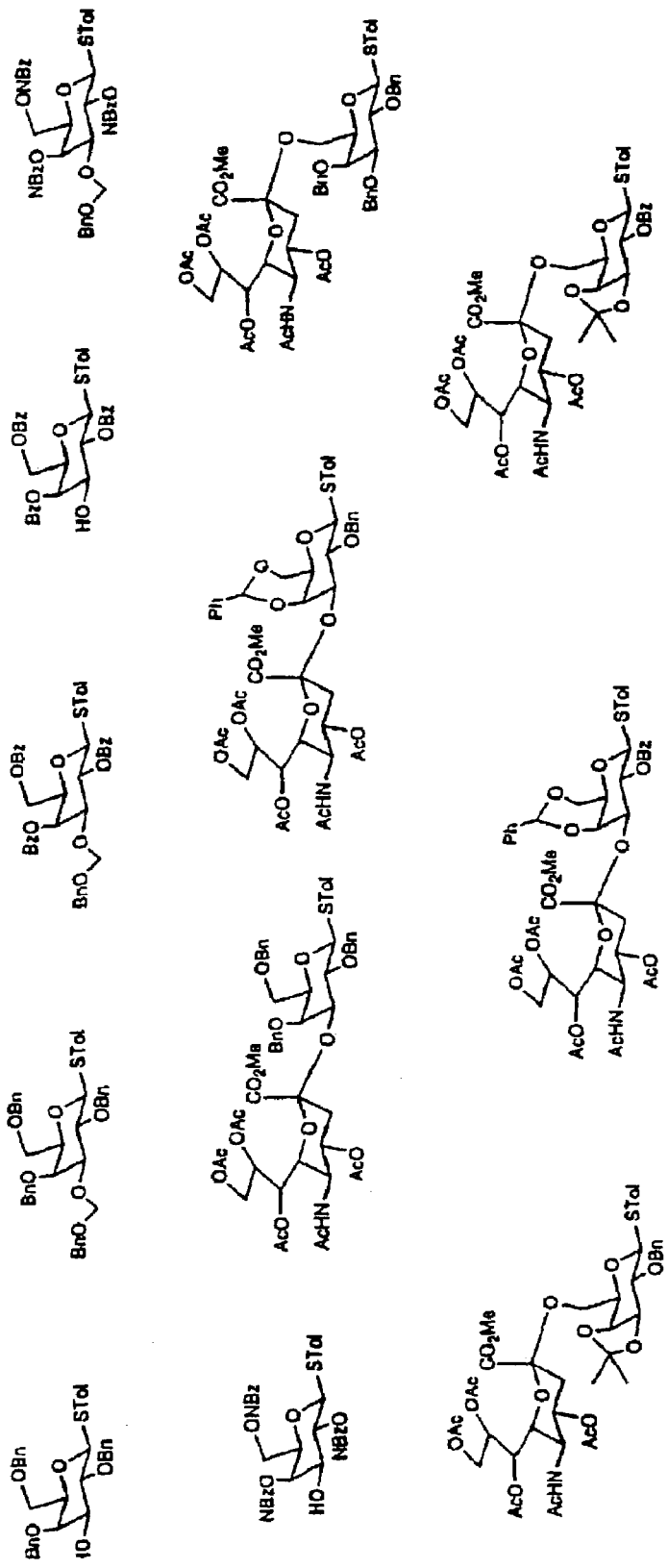
FIG. 28 illustrates some designed building blocks of thiogalactoside.
Figure 29:
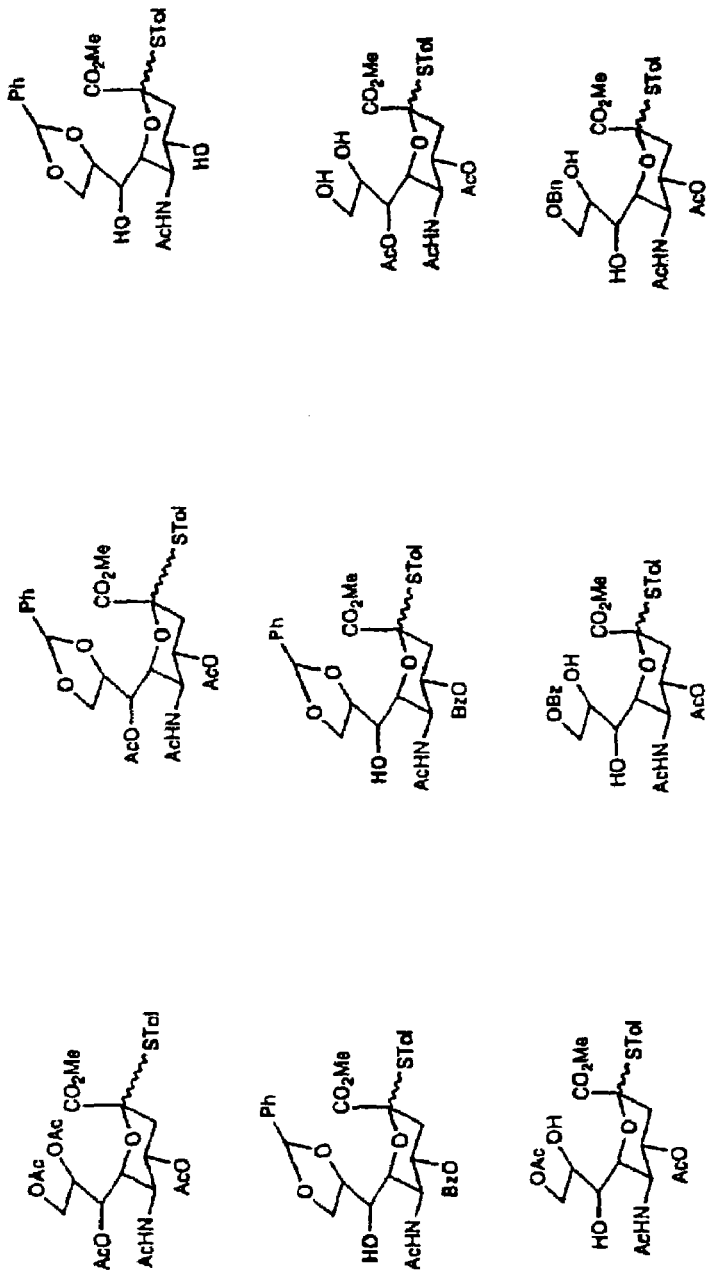
FIG. 29 illustrates some designed building blocks of sialic acid thioglycoside.
Figure 30:
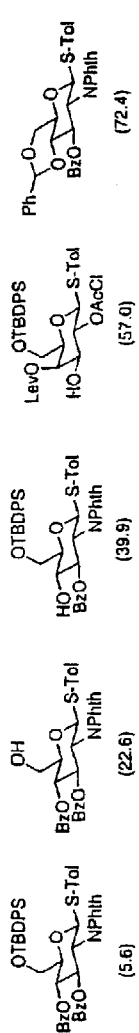
FIG. 30 illustrates relative reactivity values of some thioglycosides.
Figure 31:
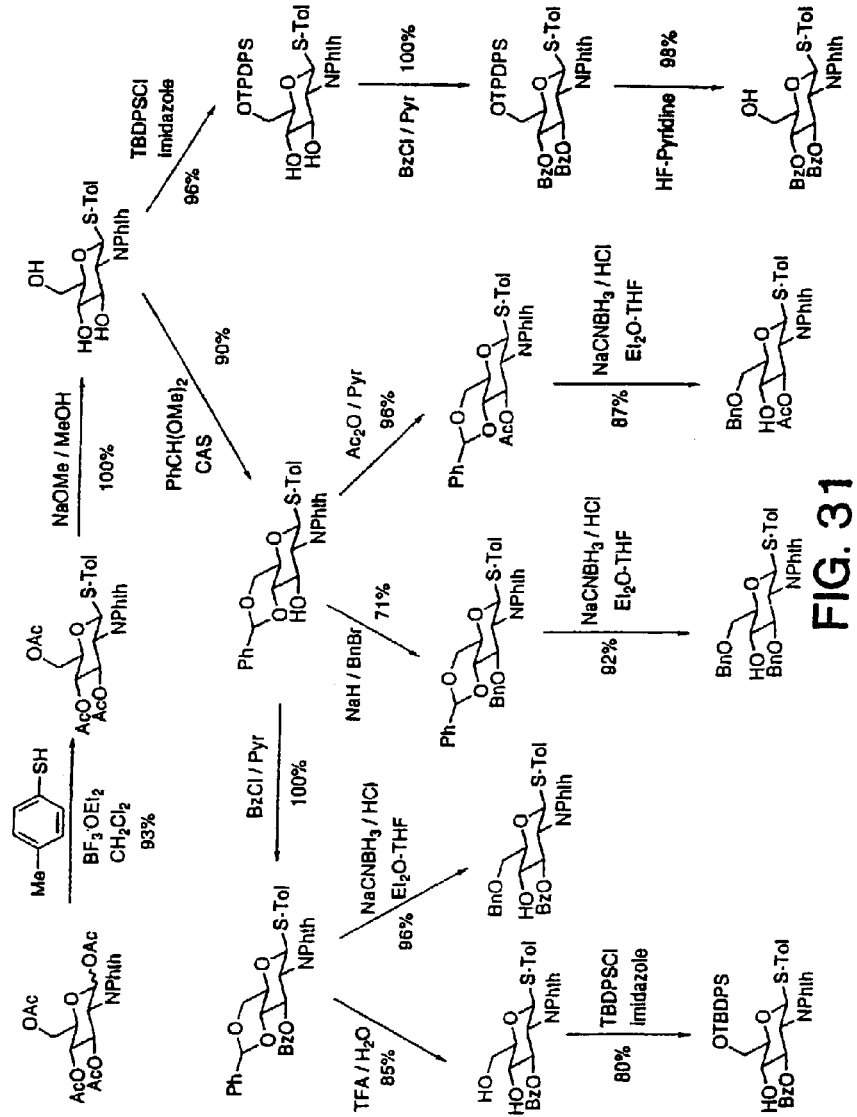
FIG. 31 illustrates synthetic schemes for some building blocks.
Figure 32:
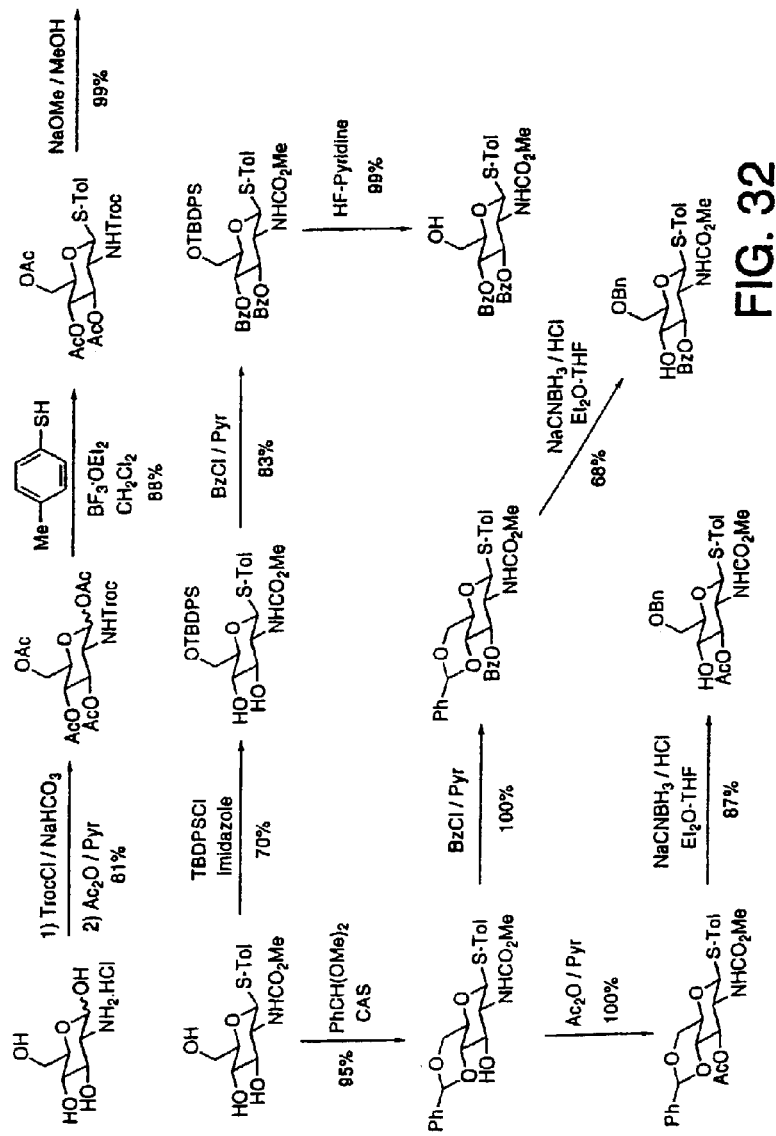
FIG. 32 illustrates further synthetic schemes for some building blocks.
Figure 33:
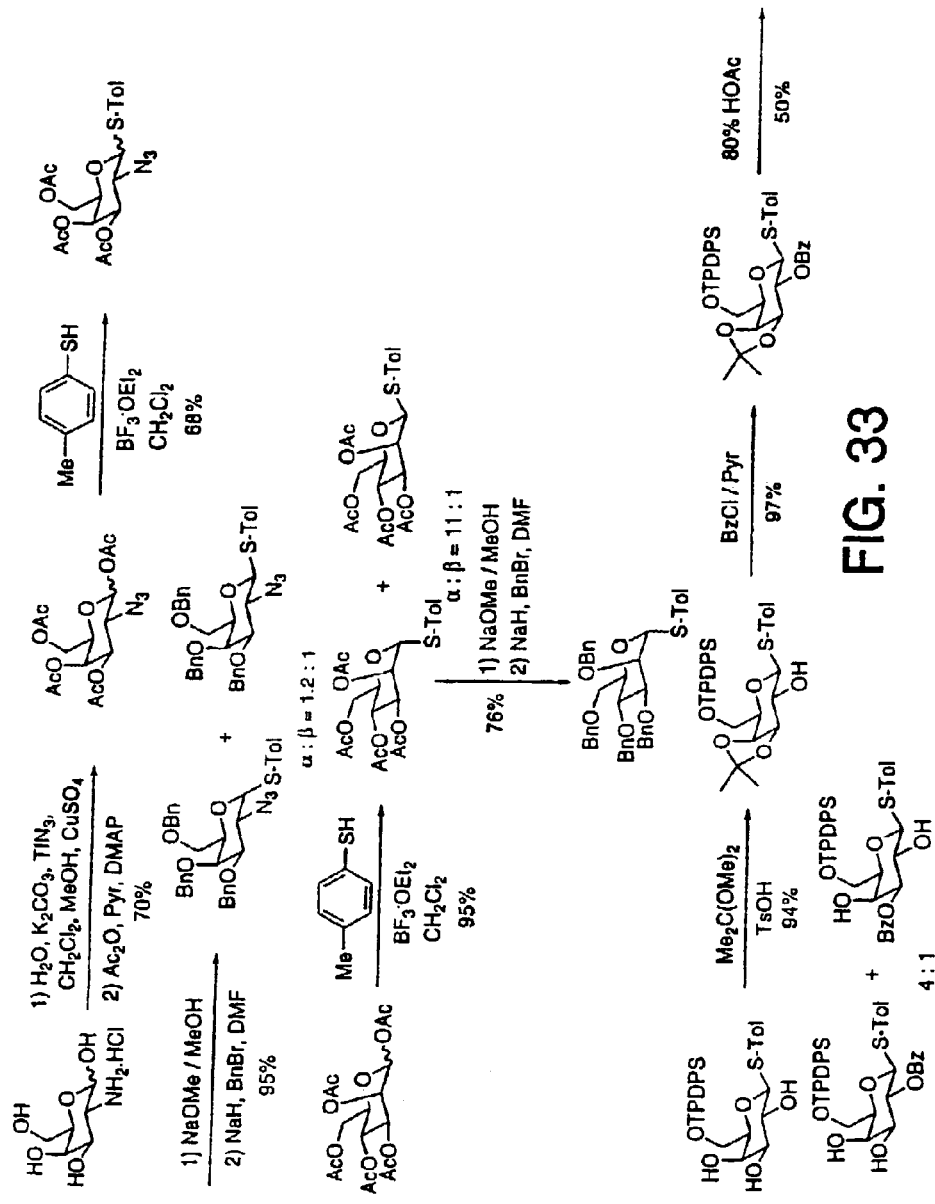
FIG. 33 illustrates further synthetic schemes for some building blocks.

In order to enhance the sensitivity of the experiment, we chose to allow a significant portion of the donors to be consumed. 1:1:1 stoichiometries of $A_1$:$A_2$:$E^+$ in the presence of five equivalents of acceptor (methanol) were used. The integrated second-order rate equations from Scheme 2 give the relationship between relative rate constant ratios and donor concentrations as shown in equation 1. A typical HPLC analysis of relative reactivities in a competition experiment is shown in FIG. 21.

$$k_{obs,1}/k_{obs,2}=\ln([A_1]_t/[A_1]_o)/\ln([A_2]_t/[A_2]_o) \quad (1)$$

The internal self-consistency of these measurements were determined by examining a series of relative rate constants (Table 2). Comparing the experimental data and calculated data with each pair shows that the average error is about 10%. This accuracy should be sufficient for the use of this data library for guiding one-pot oligosaccharide syntheses.

In addition, we were interested in how different promoters will affect the reactivities of glycosyl donors. We measured the relative reactivities between two pairs of donors: 14 vs 11, and 7 vs 5, with two promoter systems: NIS-TfOH and DMTST. The observed RRV's were approximately the same in both promoter systems: $k_{14}/k_{11}$=1.4 (NIS-TfOH) and 1.4–2.0 (DMTST), and $k_7/k_5$=2.0 for NIS-TfOH and 1.3–1.7 for DMTST. (Note: A precise measurement with DNTST is difficult as its efficiency for the activation is lower than NIS, normally 4 equiv. of DMTST are used for the glycosylation and the reaction is much slower than NIS. We observed that 2 equiv. could be enough to complete a reaction with 1

Structural Effects of Monosaccharides on the Anomeric Glycosylation Reactivity:

The completion of the table of FIG. 17 allows us to examine the influence of stereochemistry and identity of different substituents on the anomeric reactivity of various types of glycosyl donors. From the results in Table 3, it is clear that the most reactive sugar is fucose followed by galactose, glucose and mannose. (Table 3.-A) Perbenzylated fucose 50 is 4.2-fold more active than perbenzylated galactose 48, and the latter is 6.4-fold more active than perbenzylated glucose 43. The higher reactivity of the fucoside is probably because the —$CH_3$ group is more highly electron donating than the —$CH_2OBn$ group. The reactivity order of different sugar cores appears to remain very similar when the experiments are performed with different types of protecting groups. For example, when peracetylated galactose 14 (Table 3-B) was competed against peracetylated glucose 5, the ratio of 5.3 in favor of galactose 14 was obtained. The higher reactivity of the galactoside than the glucoside has been reported in the study of hydrolysis of glycosyl halides (Paulsen, H., *Angew. Chem. Int. Ed. Engl.,* 1982, 21, 155) and glycosides (Miljkovic, M. et al. *J. Org. Chem.* 1997, 62, 7597). It presumably arises due to the stereo- and inductive effects and possible involvement of the axial 4-O lone-pair electrons in the stabilization of the oxocarbenium ion intermediate (ibid, (Miljkovic, M. et al. 1997). Based on the results in Table 3, the reactivity order of monosaccharides appears to be Fucose>Galactose>Glucose>Mannose.

TABLE 3

A

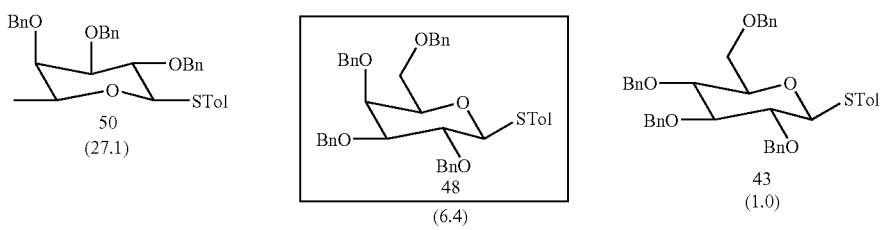

B

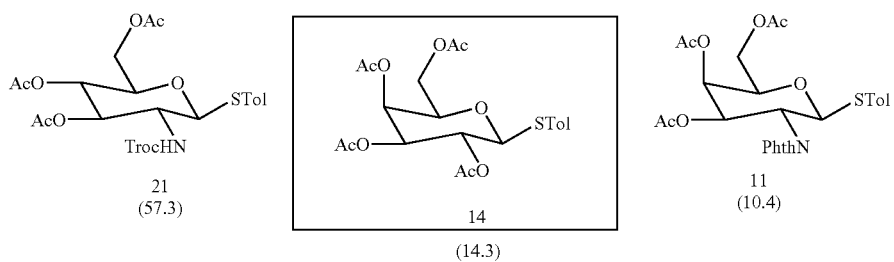

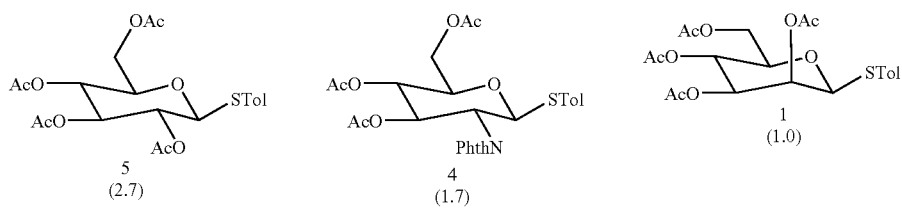

Since amino sugars are widely found in natural systems, and provide very distinct electronic and structural features, we wanted these important systems to be included in our investigation. Initially, we selected the most abundant glucosamine and galactosamine cores. The phthalyl group keeps the above trend of the reactivity difference between galactose and glucose structures (the reactivity of N-phthalyl galactose 11 is 6.1-fold higher than that of N-phthalyl glucose 4), the unusually high reactivity of trichloroethyl oxycarbonyl (Troc) group protected amines was very surprising. For example, the N-Troc protected glucosamine 21 (Table 3B) is 33.7-fold more reactive than the corresponding N-phthalyl protected glucosamine 4. Furthermore, glucosamine 21 becomes even more reactive (5.5-fold) than the corresponding galactosamine 11 in which the amine is protected with phthalyl group. This observation is particularly important in terms of regulating the relative reactivities of aminoglycoside donors for the assembly of a target compound with a 2-amino sugar either at (or close to) the non-reducing end or at (or close to) the reducing end. The elevated reactivity of N-Troc protected glucosamines might be the result of the electron giving property of the HN-trichloroethoxyl carbonyl group to stabilize the intermediate as shown in the following tentative mechanism. The research is underway to test the proposal.

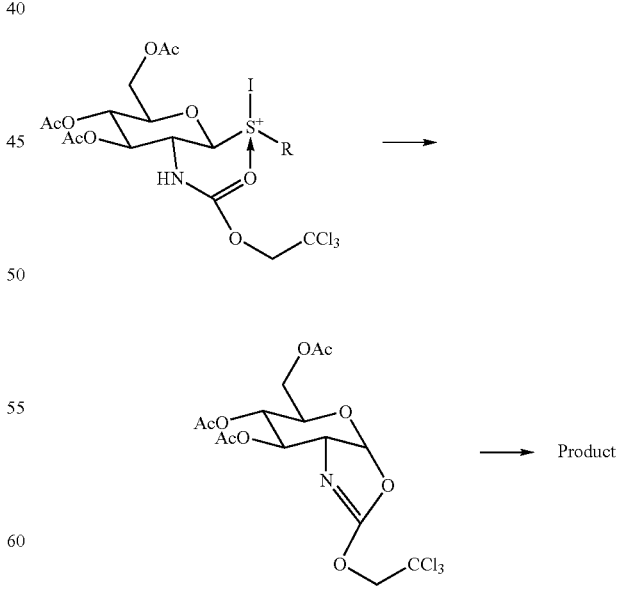

For an accelerated acetolysis of 2-AcNH glucoside in acetic acid, see Cocker, D. et al, *J. Chem. Soc. Perkin Trans.* 2 1976, 618.-

Effect of Protecting Groups on the Reactivity of Thioglycoside Donors:

The effect of substituents on the reactivity at the anomeric center has been long recognized. (Feather, M. S. et al. *J. Org. Chem.* 1965, 30, 153; Capon, B.; *Chem. Rev.* 1969, 69, 407; Fraser-Reid, B. et al. *Can. J. Chem.* 1969, 47, 393; Paulsen, H. et al *Carbohydr. Res.* 1974, 38, 312.) Glycosyl donors with ester protecting groups undergo glycosylation reactions much more slowly than do the corresponding donors with ether protection. The reason for this phenomenon is that the electron withdrawing character of the ester group destabilizes the putative cationic transition state leading to glycoside formation. Recently Ley and co-workers have provided the first systematic quantitation of such an effect by comparing the reactivity differences between benzoate and benzyl groups on rhamnosyl and mannosyl donors.(ibid, Douglas, N. L. 1998). In our hands, this effect seems to be one of the most pervasive and consistent determinants of glycosyl reactivity.

TABLE 4

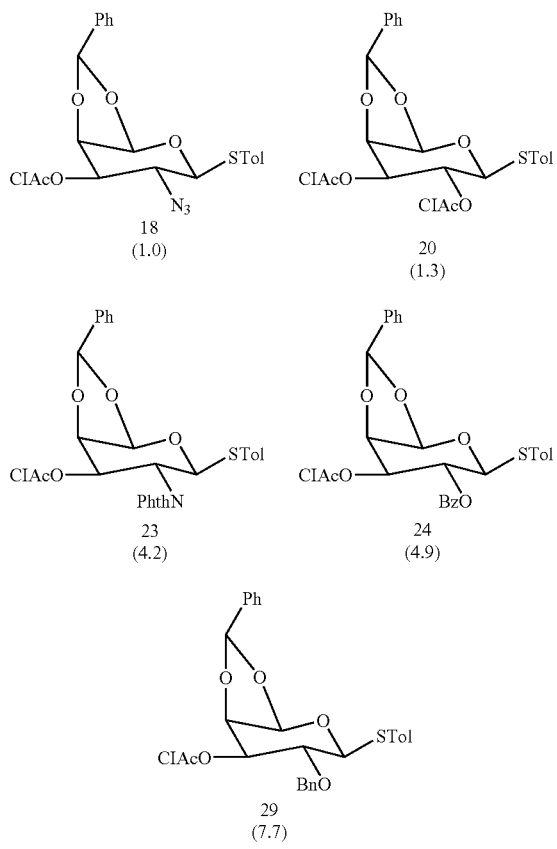

The data presented here allow detailed examination of the activation or deactivation of a series of glycosyl core structures in conjunction with a number of different protecting groups at the 2-position. Within the specific confines of the galactosyl core (Table 4), for example, we can conclude that the deactivating power of different electron withdrawing groups is in the order of —$N_3$>—OClAc —NPhth>—OBz>—OBn.

Effects of the Electron Withdrawing Group Position:

The reactivity perturbation arising from the exchange of one protecting group for another was found to be highly dependent on the position of the protecting group around the glycosyl core, as well as the identity of that core. The first effect can be demonstrated by comparing the reactivity of sugars with a benzoyl protecting group versus those with a hydroxyl group at the same position (Table 5). Removal of benzoyl group from the 4-O position causes the largest increase in the rate of reaction. This was however not seen for other pyranoses, for which the protecting group at the 2-position has been found to be more important (ibid, Douglas, N. L. 1998). This might be explained by the participation of 4-oxygen of galactose in the stabilization of putative cationic transition state (ibid, Paulsen, H. 1982). The observed stronger effect of C3-OH relative to that of C2-OH might be explained by its close association with the substituent at the 4-position. In addition to the destabilization of the presumed cationic transition state through inductive effects, benzoylation of the 3-position may also diminish the participation of the lone-pair electrons of C4 oxygen in the stabilization of the cationic transition state. From Table 5, the observed influence of the positions of the benzoate group is in the order of 4>3>2>6. These results are different from those observed for the mannose system, in which the order of 2>6>4>3 was determined (ibid, Douglas, N. L. 1998). In the latter case, except the neighboring 2-position, the proximity of the benzoate to the ring oxygen was found more important than its distance from the anomeric position.

TABLE 5

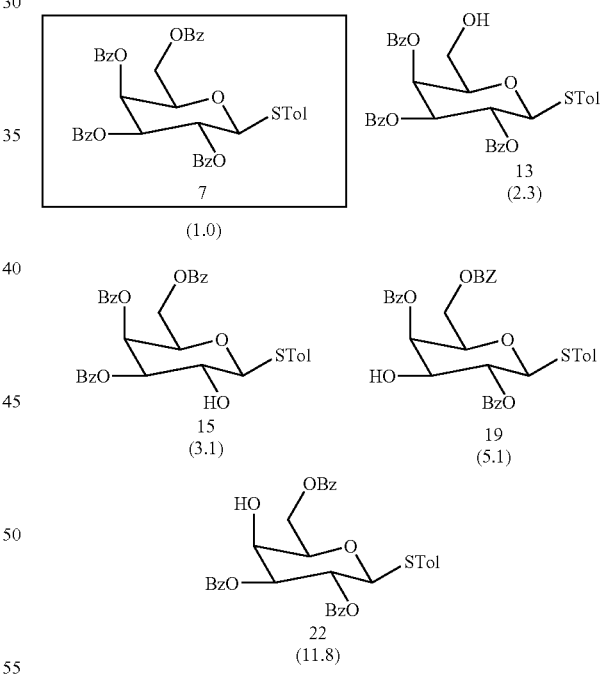

The results presented in Table 5 also provide, for the first time to our knowledge, a direct reactivity comparison between the protecting group and the hydroxyl group in the same position. Such data is of particular importance for the design of highly chemoselective one-pot glycosylation sequences (Scheme 1) in which the acceptor molecule in one step becomes the donor in the following step (ibid, Grice, P. et al 1997). Therefore, the reactivity measurements of glycoside donors that also contain one free hydroxyl group is crucial for the successful accomplishment of such a challenging task. For this purpose we have examined and broadly quantified the influence of various protecting groups and monosaccharide type on the reactivity of monohydroxy glycosides as donors (Table 5–7).

pound 29, Table 4), the same comparison between benzoate and benzyl systems in 3-hydroxyl free galactosides 42 and 49 (Table 6A) gave the factor of 11.2. Similar inconsistency

TABLE 6

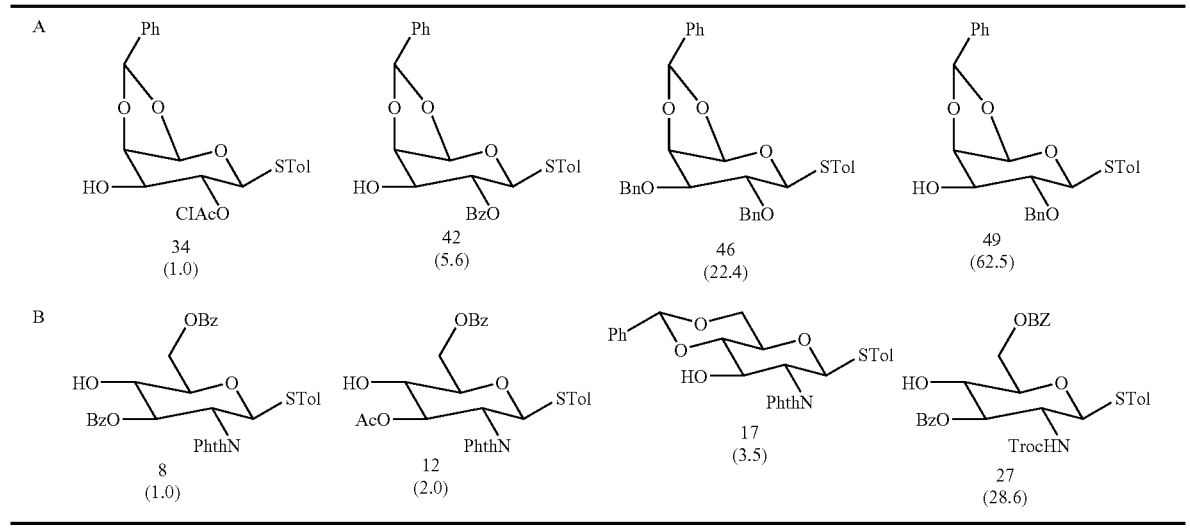

It should also be noted that the reactivity of 4,6-benzylidene protected galactose derivatives that have a free 3-OH group (structures in Table 6A) is influenced by C-2 protecting groups in the same manner as when the 3-OH was protected. Thus, the deactivating effects of different groups at the C-2 position are in the same order (—OClAc>—OBz>—OBn) as it was observed from the 3-OClAc protected galactoside derivatives in Table 5. However, the magnitude of the deactivating effects is significantly dependent on the identity of the other protecting groups on the molecule. For example, while the benzoate protection at 2-position caused the galactoside 24 to be 1.6 times less reactive than the benzyl group in the same position (compound 29, Table 4), the same comparison between benzoate and benzyl systems in 3-hydroxyl free galactosides 42 and 49 (Table 6A) gave the factor of 11.2. Similar inconsistency in the deactivation power is seen for the pair 2-OAcCl (20) and 2-OBn (29) when the position-3 was protected (5.9-fold difference, Table 4), or free (62.5-fold difference between 34 and 49 in Table 6A.) Thus, there are not consistent quantifiable reactivity trends which lend themselves to a simple numerical reactivity model. Though there exist consistent qualitative trends (e.g. —OBn is less deactivating than —OBz) the degree of this influence appears to be highly dependent upon the structure of the rest of the molecule. As a result, we have taken the approach of directly measuring the relative reactivity of each donor that enters our library.

TABLE 7

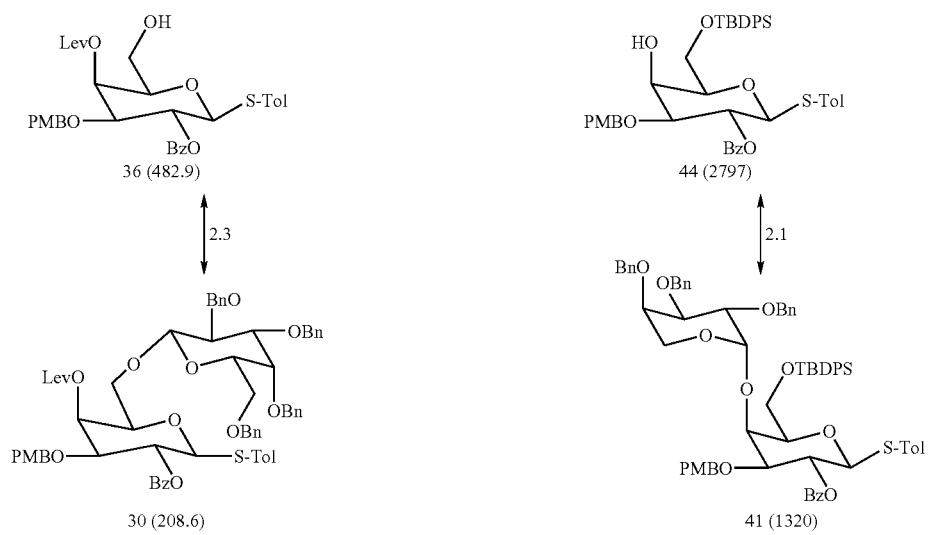

TABLE 7-continued

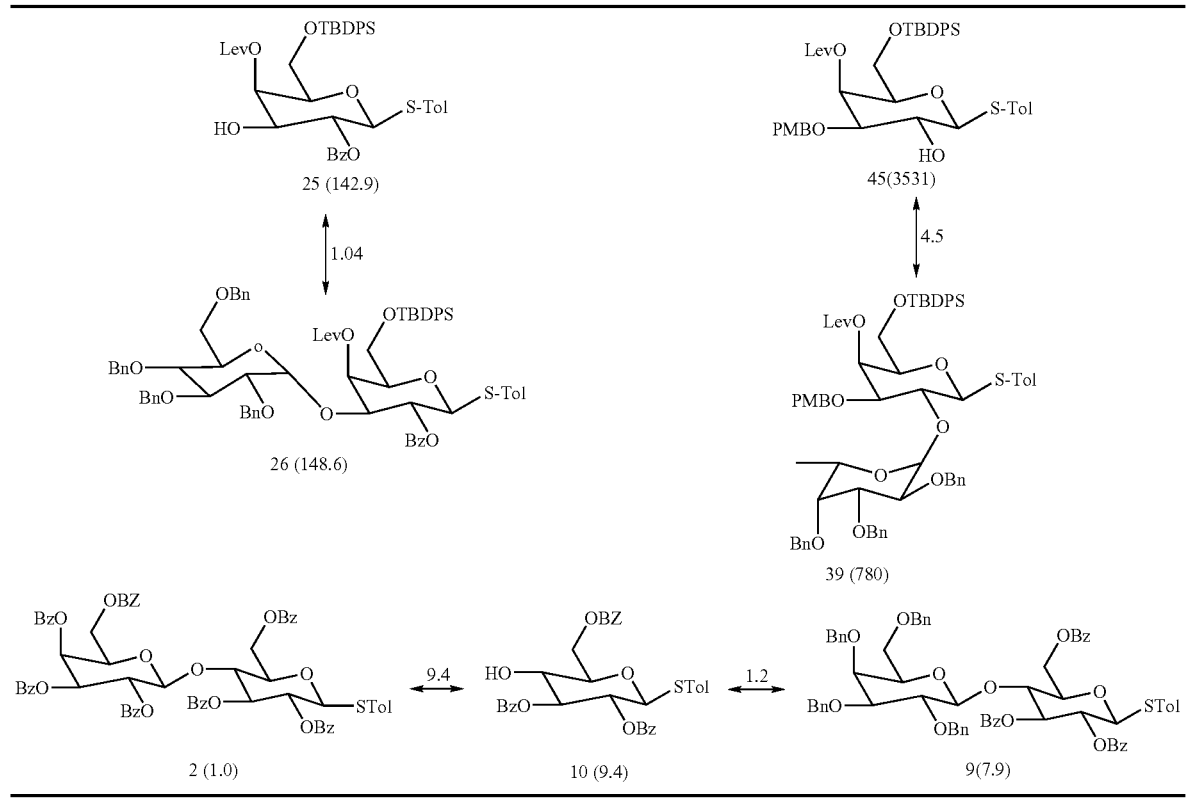

The Effect of Glycosylation on Donor Reactivity:

Glycosylation of a free hydroxyl has a slight deactivating effect on the anomeric reactivity of the acceptor. This is significant as for the second and later steps, the reactivity of the growing oligosaccharide reducing end generally has not been explicitly characterized. Fortunately, the deactivating effect of glycosylation is typically small in most cases relevant to the synthesis. This issue was examined on a series of different structures and the results are shown in Table 7. In general, the results show that glycosylation of the hydroxyl function of a given monohydroxy sugar, causes a small decrease in reactivity. Glycosylation by a per-benzylated sugar causes decrease in reactivity by a factor of 1.1–2.3 depending on the position of glycosylation, while glycosylation by a per-benzoylated sugar caused more significant decrease in reactivity (a factor of 9.4 for 2 (10). A somewhat larger deactivating effect from perbenzylated sugars when glycosylating the 2-position of the acceptor was observed in one case (a factor of 4.5 for 45 (39). This may be the result of significant steric effect on the anomeric center. It seems that the degree of deactivation introduced by the glycosyl structure varies with the reactivities of the glycosyl donors. Less reactive glycosyl donors are more strongly deactivating once the glycosyl linkage is formed.

Fortunately, in the context of the synthetic methodology developed here, the glycosylation reactions that have the most impact on the anomeric reactivity of the acceptor are those that are the most electron withdrawing (those that tend to come at the very end of the synthetic route. The largest deactivation will occur on the last donor. Since the reducing end is typically expected to be an unreactive glycoside such as a methyl glycoside, there is no competing reaction at the step when it is appended to the oligosaccharide chain and so deactivation is not expected to be a problem at that step.

Thus, the worst relevant reactivity shifts due to glycosylation will occur upon glycosylation of the third residue from the reducing end by the fourth residue from the reducing end. In cases of syntheses of tetra-, penta- or hexa-saccharides, the fourth residue from the reducing end is expected to be reasonably active. Therefore, its deactivating effect is not likely to be large even in the worst of cases for targets of this size. However, it should be noted that in extended synthetic schemes, it would likely be prudent to leave a larger reactivity window between donors at the last steps of the reaction sequence to account for glycosylation-associated deactivation.

Figure 18:
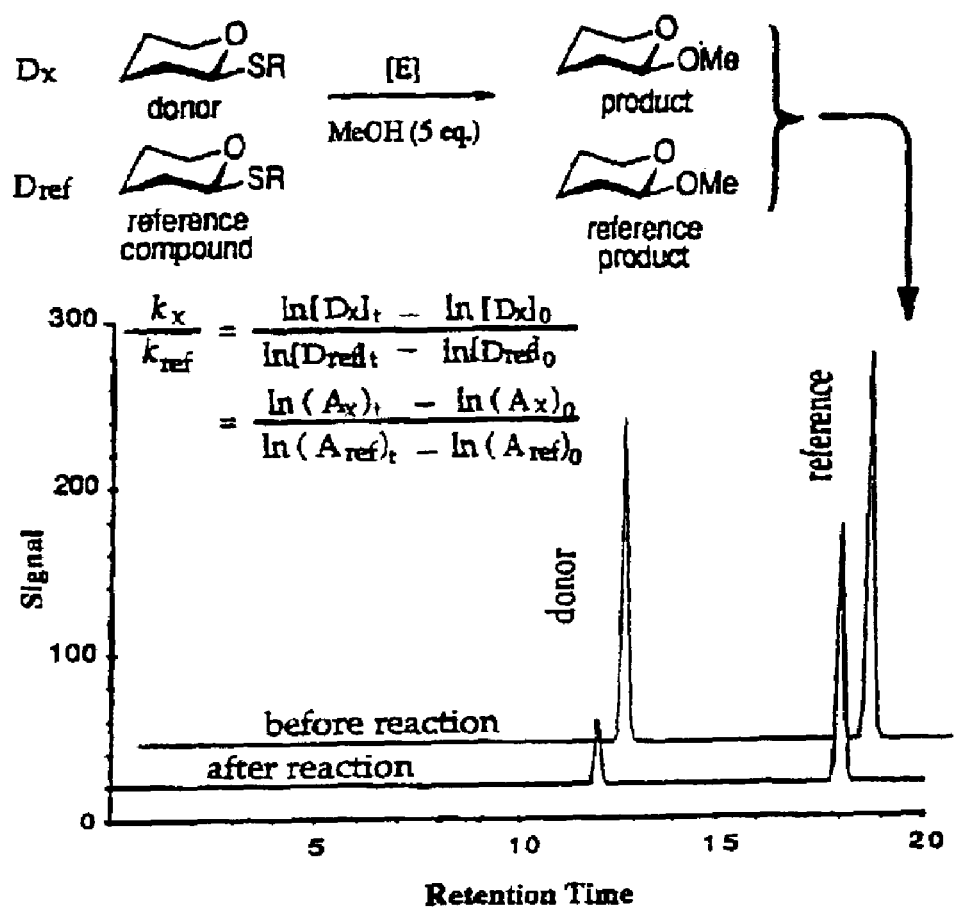
FIG. 18 illustrates an example of the relative reactivity measurement between a thioglycoside ($D_x$) and the reference compound ($D_{ref}$) by using HPLC (see Experimental Section for Details). The intensity of absorbance at 256 nm for each remaining donor was measured to determine the relative reactivity $k_x/k_{ref}$. $[D]_t$, donor concentration at time t; $(A)_t$, donor absorbance at time t.

Correlation between Chemical Shift of Anomeric Proton NMR with ln(RRV's):

During the study of thioglycoside reactivity, we have observed that the chemical shift of the anomeric proton of the more active perbenzylated thioglycoside 48 is remarkably farther up-field than the less active perbenzoylated analog 7 ($\delta$=4.58 ppm vs $\delta$=4.98 ppm). Interestingly, when we examined some compounds which have the same protecting group (—OBz) at the C-2 position on the same core structure (e.g. galactose), we observed a good linear correlation between the chemical shifts of the anomeric protons and the corresponding ln(RRV's) (FIG. 18). Compounds with different protecting groups at C-2 position do not show a good correlation, probably due to different shielding effects or other unknown mechanisms. Since the stability of the glycosylation transition state appears to be largely influenced by the electron density of the anomeric center, the chemical shift of the anomeric proton might be used to rapidly determine the anomeric reactivities in certain cases.

Prediction of Optimal Donor Reactivities:

Notwithstanding the appearance of unwanted side reactions and other effects which detract from the yield of all glycosylation reactions, the highest yielding glycosylation steps will be those which have the greatest difference in anomeric reactivity between the donor and the acceptor. Thus, a high yielding multi-step procedure is one which will employ the largest reactivity difference at each step. As a result, those donors which are destined to react in the first coupling step should be drawn from the pool of the most reactive donors available and those which are destined to react at the last coupling step should be drawn from the pool of least reactive available donors. The logarithmic nature of Equation 1 implies that there is a strongly diminishing return in yield to be gotten from increasing the ratio of relative anomeric reactivities of the donor and acceptor at a given step. Thus, reducing the ratio of relative rates for one step so as to increase it for another will result in a sizeable loss in overall yield unless the ratio in the first step was larger than that of the second to begin with. Thus, it should be evident that for optimal yield, the ratio of reactivities between donor and acceptor should be the same (and as large as possible) for each step. The principle of constant rate ratios allows us to predict that the optimum relative reactivity value ($k_x$) to be used at each step x in a sequence of N steps is given by equation 2. $k_1$ is the relative reactivity constant of the donor to be used in the first step. $k_N$ is the relative reactivity constant of the donor to be used in the $N^{th}$ step:

$$k_x = k_1 (k_N/k_1)^{(x-1)/(N-1)} \qquad (2)$$

Figure 19:
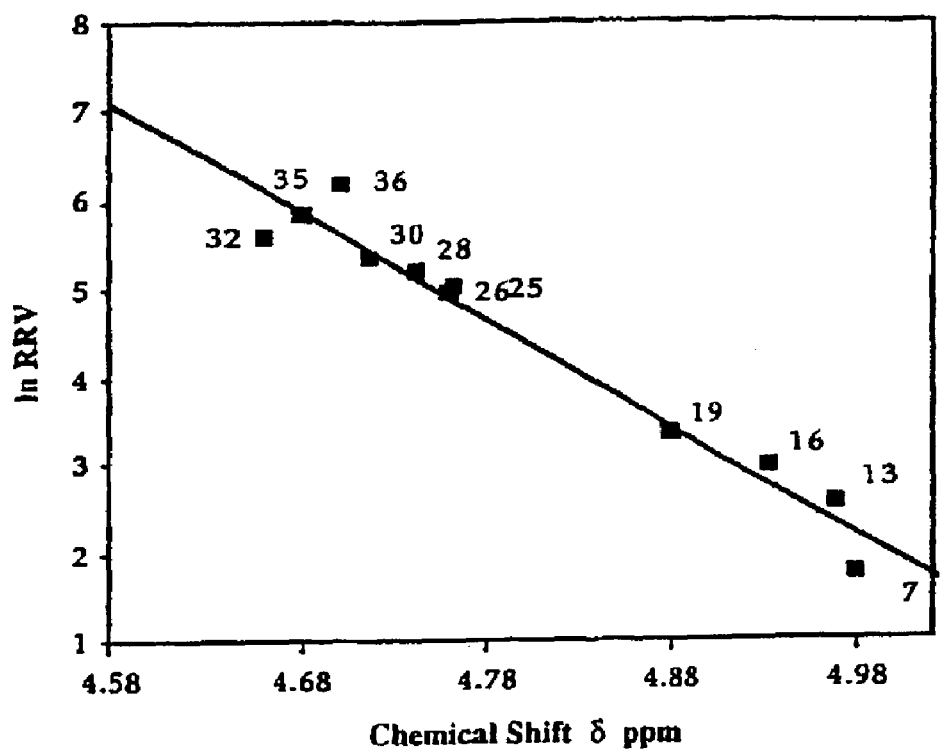
FIG. 19 illustrates the relationship between the chemical shifts of the anomeric protons of thioglycosides and their lnRRVs.

Computational Approach:

Since exactly the right donor reactivity as predicted by Equation 2 is not always available for every step, we generated a computer program that can search the donor library for the best sets of available donors, allowing for the programmed assembly of oligosaccharides. The program, named "OptiMer," interfaces with a database of donors (data from the table of FIG. 17) stored using the FileMaker Pro 4.0 (FileMaker Inc.) database program. The database stores the type of sugar core that it contains, the location of any unprotected hydroxyls that may be glycosylated, and the α- or β-directing nature of the substituent at the 2position which is used to predict the product stereochemistry at the anomeric carbon. OptiMer considers all this information when examining sequence combinations. In addition, the database also stores a picture of the compound, its name and a reference to the literature where the preparation of the donor is described. Once given a target sequence (e.g. DGalα1,4DGlcNβ1,6DGalβ1,4DGlc) the program searches the in house database to identify the 100 best sets of available characterized oligosaccharide donors (see FIG. 18 as an example). For large sequences, a "Monte Carlo" search method is also available, which simply tests combinations at random. The frequency with which each donor appears at each step in the list of the best 100 donor sets is tabulated and the user is presented with a list of donors at each step which tend to give the highest overall yields (FIG. 19). The chemist is then free to make an educated choice as to which donors to use based on availability, cost and knowledge of the optimal mathematical relationships between donor reactivities as detailed above. We believe this program will become very useful when the number of building blocks is expanded.

One-Pot Synthesis of Oligosaccharides:

With this database and the computer program in hand, we then performed the one-pot synthesis of several tri- and tetrasaccharides (Schemes 3 and 4). The building blocks were added sequentially in order of their decreasing RRV's. Scheme 3 illustrates the synthesis of linear trisaccharides 52, 53 and 54. The overall yield of each trisaccharide synthesis is in the range of 60%, which corresponds to about 80% yield of each coupling step. Trisaccharide 52 contains both α- and β-glycosidic linkages, and was prepared with the donor 48 being active and the acceptor 19 being inactive. Indeed, according to their RRV's, perbenzylated 48 is 588-fold more reactive than the benzoylated 19. However, the syntheses of trisaccharides 53 (Scheme 3b) and 54 (Scheme 3c) could not be performed without the quantitative information on the RRV's of the appropriate donor and acceptor molecules. In the synthesis of 53, we first employed the relatively activating N-Troc protecting group for 2-amino glycosides. The 2-N-Troc protected thioglucoside 21 is 4.4 fold more active than the benzoylated galactoside 13. This difference in RRV's was sufficient to perform the one-pot synthesis of trisaccharide 53 in the overall yield of 56%.

The synthesis of trisaccharide 54 (Scheme 3c) demonstrates the sequential construction of two alpha glycosidic bonds in a one-pot manner. The thioglycosides used in this synthesis are 50 and 49, and the difference in their RRV's is only 3.6-fold. In order to increase the selectivity of the coupling step, the donor 50 was used with 1.5 equiv. and the reaction was performed with the promoter DMTST. The results in Scheme 3 demonstrate that the RRV's database can be sufficiently applied not only for NIS-TfOH promoted reactions, but also for the DMTST-promoted glycosylations, and may further be utilized for other promoters to activate thioglycosides.

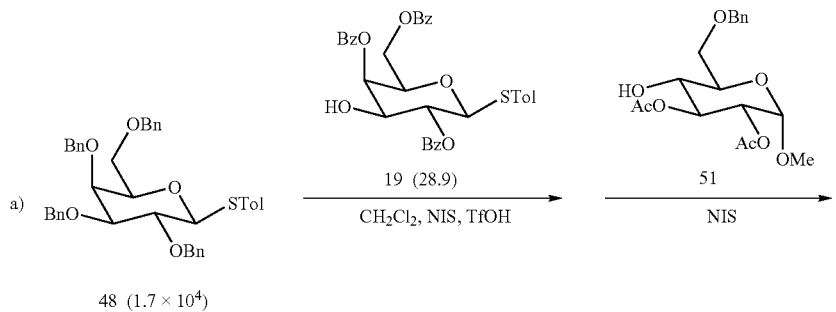

Scheme 3.

-continued

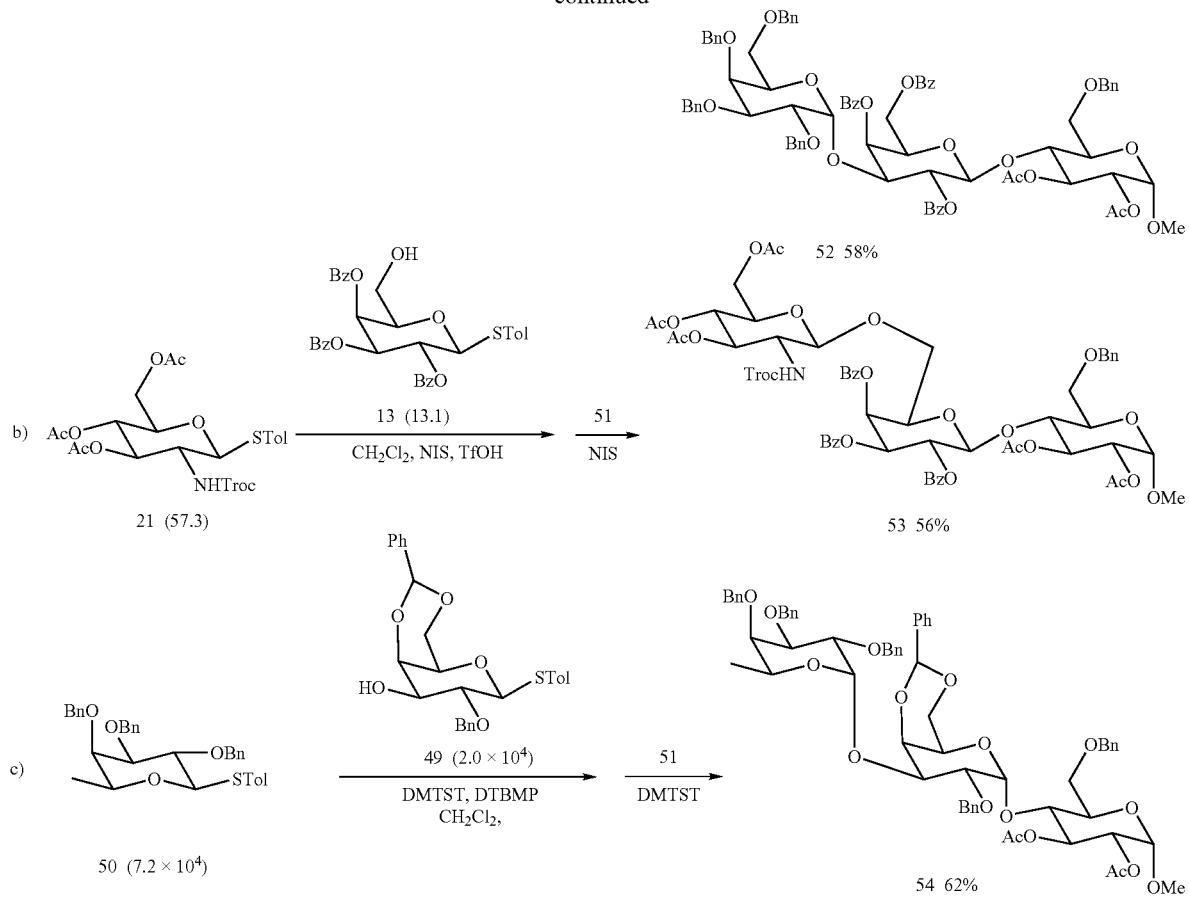

To demonstrate the application of the relative reactivity donor database, we constructed two different tetrasaccharides, compounds 55 and 57 (Scheme 4), in a one-pot manner. In the synthesis of 55 we used the reactivity differences of 104 (48(27) and 5.9 (27(13) for the first two glycosylation steps, respectively. While these reactivity differences were sufficient to synthesize the target tetrasaccharide 55 in an overall 40% yield (about 74% yield for each coupling step), it should be noted that the efficiency of this synthesis is much lower than it is predicted by the OptiMer search (82%, see FIG. 18). Two main reasons for this high discrepancy between the theoretical and experimental results are immediately apparent. One reason is that at this stage of the development, the OptiMer program does not consider the possibility of the occurrence of side reactions (e.g. decomposition reactions) and the deactivation introduced by the newly formed glycosyl bond. Thus the reaction yields reported by OptiMer should be considered yield optima, analogous to a 100% yield in a normal reaction.

Scheme 4.

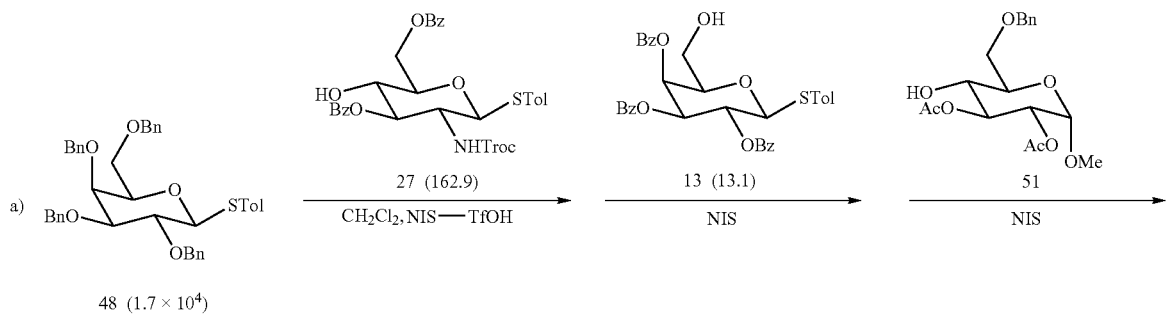

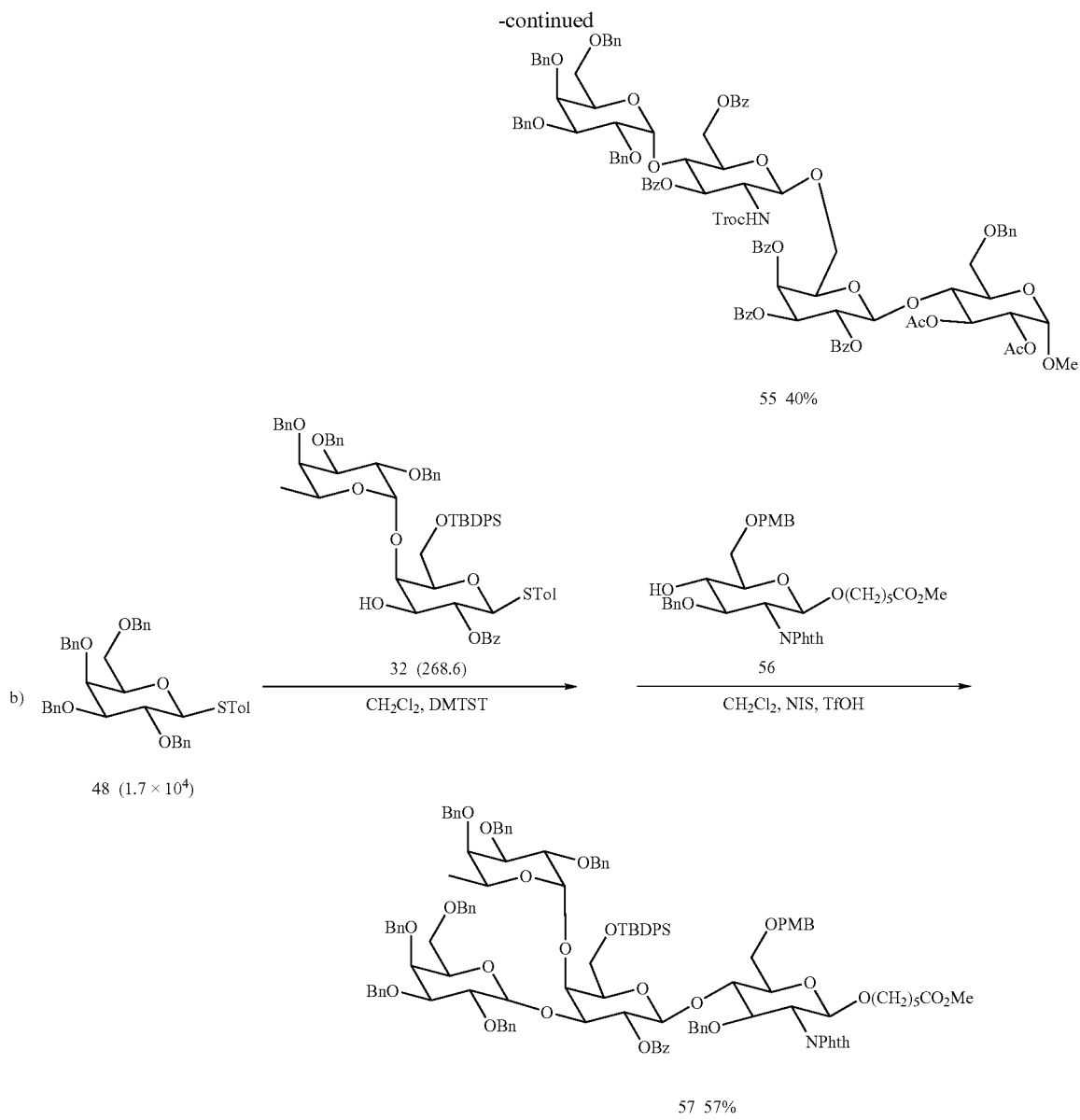

The second main reason relates to the promoter system NIS-TfOH. When using NIS-TfOH, an equimolar amount of succinimide is generated in the reaction mixture. Although the nitrogen of succinimide is a poor nucleophile, in the case of highly unreactive acceptors, it can compete effectively for the remaining pool of activated glycosyl donors. This is most important when the hydroxyl of the sugar acceptor is very hindered (e.g. 4-OH of glucose, 4-OH of galactose) or has a poor nucleophilicity (e.g. due to electron-withdrawing substituents in the vicinal position). Indeed, in several cases of the preparation of the disaccharide building blocks in the table of FIG. 17, we have isolated and characterized the glycosyl succinimide products. For example, in the synthesis of the lactoside 9, in addition to the target disaccharide 9 (65%), the succinimide product 58 (15%) was also isolated as a byproduct. The low reactivity of the 4-OH of glucoside 10 (RRV=8.4), coupled with an increased reactivity of the transient intermediate cation derived from the initial reaction of galactoside 48 (RRV=1776) with iodonium ion, could explain the formation of 57. Moreover, since in the one-pot sequential synthesis, the succinimide accumulates from step to step, it may become especially problematic for the later steps, resulting a significant decrease in the overall yield of the target glycosylation product. One way to avoid such problems is to use a combination of two promoter systems: DMTST and NIS-TfOH. Although DMTST is less active than NIS-TfOH and is not suitable for unreactive donors, it does not produce a nucleophile as a side product. It can be used at the initial steps of one-pot syntheses, which often contain very reactive thioglycosides. In later steps, which contain less reactive thioglycosides for which DMTST is no longer appropriate, the reaction can be promoted by NIS-TfOH, thereby diminishing the overall buildup of succinimide. This protocol was successfully employed for the assembly of the branched tetrasaccharide 57 (Scheme 4b). This work highlights the importance of further investigation into thioglycoside activators with non-nucleophilic by-products.

Based on the orthogonal protection-deprotection strategy developed in our laboratory for the synthesis of a highly branched oligosaccharide library (Wong, C.-H. et al. *J. Am. Chem. Soc.* 1998, 120, 7137), we have also demonstrated the possibility of combination of orthogonal protection-deprotection strategy and the one-pot sequential strategy in the synthesis of branched oligosaccharide. This combination provides an efficient method for rapid assembly of highly branched oligosaccharide libraries, as shown in the construction of the branched tetrasaccharide 57 (Scheme 4b). We have prepared some orthogonally protected disaccharides thioglycoside analogs and studied their reactivities (the table of FIG. 17). In the synthesis of the branched tetrasaccharide 57, we first performed the reaction between 48 and 32 in the presence of NIS-TfOH, and found that the reaction proceeds with very fast consumption of the donor to give exclusively the succinimide galactoside. All the starting acceptor 32 could be recovered from this reaction mixture. We assume that the elevated reactivity of the donor 48 coupled with high steric hindrance of the secondary hydroxyl in 32 leads to a very efficient competition of succinimide to afford the by-product.

To solve this problem, the reaction between 48 and 32 was performed by the use of DMTST as a coupling reagent (Scheme 4b). In these conditions, the reaction proceeded smoothly and the product, without the isolation, was further treated with acceptor 56 in the presence of NIS-TfOH to afford 57 in a one-pot two-step procedure (57% yield). Further investigation is underway in order to construct 57 from the corresponding monosaccharides in a one-pot manner by using the similar combination of NIS and DMTST. In addition, the strategy employed for the synthesis of tetrasaccharide 57 (Scheme 4b) might be a general strategy for the preparation of branched oligosaccharides library. The key of such an approach is the orthogonally protected monosaccharide, like galactoside 59 (ibid, Wong, C.-H. et al 1998) and 35 (see experimental). This sugar was selectively deprotected at each position to generate the corresponding mono-hydroxy sugars 25, 36, 44 and 45, carrying a free hydroxyl groups at 3, 6, 4 and 2 position, respectively. Each of these compounds was glycosylated by the donor with higher RRV, to generate the corresponding disaccharides; for example, 25(26, 36(30, 44(41, and 45(39. The observed disaccharides each can be further deprotected selectively at the remaining three positions of the orthogonally protected sugar portion to generate 4·3=12 mono-hydroxy disaccharides (e.g., compound 32 was prepared from 41 by selective deprotection of 3-p-methoxybenzyl group). These structures can then be subjected to the one-pot assembly of tetra- or pentasaccharides, as we have demonstrated here in the synthesis of 57 (Scheme 4b), and is generally illustrated in Scheme 1. Such an approach, with an ultimate aid of the relative reactivity database, forms a basis for the construction of linear and branched oligosaccharide libraries, and approximately 30 fully protected oligosaccharides have been prepared using this reactivity-based one-pot strategy (Table 8). Complete deprotection and selective deprotection of the library will generate a larger library. This work is in progress in our laboratory and will be reported in due course.

TABLE 8

| Entry | Oligosaccharides |
|---|---|
| 1 | L-Fucα1,2Galα1,6GlcN |
| 2 | L-Fucβ1,2Galα1,6GlcN |
| 3 | L-Fucα1,2Galβ1,6GlcN |
| 4 | L-Fucα1,3Galβ1,3GlcN |
| 5 | L-Fucα1,3Galβ1,4GlcN |
| 6 | L-Fucα1,3Galα1,4Glc |
| 7 | L-Fucα1,3Galβ1,6GlcN |
| 8 | L-Fucβ1,3Galα1,6GlcN |
| 9 | L-Fucα1,4Galβ1,3GlcN |
| 10 | L-Fucα1,4Galβ1,4GlcN |
| 11 | L-Fucα1,4Galα1,6GlcN |
| 12 | L-Fucβ1,4Galβ1,6GlcN |
| 13 | L-Fucα1,4Galβ1,6GlcN |
| 14 | L-Fucα1,2<br>\|<br>Galα1,3Gall,6GlcN |
| 15 | L-Fucα1,4<br>\|<br>Galα1,3Galβ1,4GlcN |
| 16 | L-Fucα1,4GlcNβ1,6Galα1,4Glc |
| 17 | Galα1,3Galβ1,3GlcN |
| 18 | Galα1,3Galβ1,4GlcN |
| 19 | Galα1,3Galβ1,4Glc |
| 20 | Galα1,3Galβ1,6GlcN |
| 21 | Galα1,3Galα1,6GlcN |
| 22 | Galα1,6Galβ1,3GlcN |
| 23 | Galα1,6Galβ1,4GlcN |
| 24 | Galβ1,6Galβ1,4GlcN |
| 25 | Galα1,6Galβ1,6GlcN |
| 26 | Galβ1,6Galβ1,6GlcN |
| 27 | Glcα1,3Galβ1,6GlcN |
| 28 | Glcα1,3Galβ1,3GlcN |
| 29 | Glcα1,3Galβ1,4GlcN |
| 30 | GlcNβ1,6Galβ1,4Glc |
| 31 | L-Fucα1,6<br>\|<br>Glcα1,3Galβ1,4GlcN |

Conclusion:

Here we disclose a process for synthesizing oligosaccharides into a systematic and rapid procedure. To achieve this result, an approach is pursued based on the chemoselective glycosylation of single acceptors in the presence of other less reactive donors. This concept brought into a predictable and reproducible practice by our development of a general methodology for the easy, rapid, and precise measurement of the relative reactivities of almost any glycosyl donor by HPLC. This methodology is employed to quantify the relative reactivities of a series of glycoside donors for use as off-the-shelf reagents in the one-pot synthesis. In addition to allowing one to plan a series of one-pot sequential syntheses of linear and branched oligosaccharides, the database of donors and reactivities also reveals a wealth of structural factors which contribute to the reactivity of the anomeric position. As observed by others, the electron withdrawing contribution of some protecting groups about the ring influences reactivity. Also characterized herein are the impact of the identity of the sugar, the position of protecting groups and other important factors which contribute to anomeric reactivity.

It is further disclosed herein that among the monosaccharide and disaccharide structures tested, the fucose core is the most reactive followed by galactose, glucose and mannose.

For 2-aminoglycosides, it is shows that their reactivity is significantly influenced by the protecting group at the nitrogen. The —NTroc group has a large activating effect compared to the —NPhth or azide group. By utilizing the Troc- and Phth-groups as a versatile protecting groups for the amine function, we have demonstrated that the change of only a single protection on the amine can be sufficient in order to regulate the reactivities either of a given monosaccharides or between different monosaccharide structures. The degree of deactivation at the anomeric center by benzoyl protection (as compared to the free hydroxyl at that position) was found to be the greatest at the 4 position on the galactose core, with the overall order of 4>3>2>6.

Because the absolute influence of a given protecting group can not be simply accounted for, it is necessary to determine the reactivity of each monomer separately. For this purpose, the Relative Reactivity Value (RRV) is defined as a relative measure of reactivity for a given monosaccharide or disaccharide. By measuring the RRV's of up to fifty different mono- and disaccharide structures, we were able to create the first database of donor reactivities and demonstrated its usefulness for rapid one-pot assembly of various oligosaccharide structures. In addition, we observed the linear correlation between the glycosyl donor reactivity and the chemical shift of the anomeric proton by $^1$H-NNM. To aid in the planning of high yielding syntheses with available reagents, a computer program, OptiMer, is disclosed that searches through the database of characterized donors and identifies sets of monomer donors which are likely to give the best yield. This database can be rapidly expanded to accommodate other mono- and oligosaccharide systems. The further development of this new synthesis strategy will surely impact the rapid access to the molecular diversity of carbohydrate structures to facilitate the discovery of carbohydrate ligands and receptors, which in turn paves a way to a deeper understanding of their biological functions.

SYNTHETIC PROTOCOLS

General Methods:

Chemicals used were reagent grade and used as supplied except where noted. Solvents were either dried by standard procedures or used as purchased. Unless otherwise stated, all reactions were performed under an argon atmosphere. All thioglycosides used in this research are p-methylphenyl thioglycosides. Compounds 3, 4, and 43 (Balavoine, G. et al. *J. Carbohydr. Chem.* 1995, 14, 1217), compounds 5, 6, and 14 (Magnusson, G. *J. Org. Chem.* 1977, 42, 913), compound 7 (Burkart, M. D. et al. *J. Am. Chem. Soc.* 1997, 119, 11743), and compound 51 (DeNinno, M. P. et al. *Tetrahedron Lett.* 1995, 36, 669) are known structures and prepared according to the published procedures. All glycosylation experiments were performed by using molecular sieves, which was flame-dried right before the reaction under high vacuum. Analytical thin layer chromatography was performed using silica gel 60 $F_{254}$ glass plates (Merck); compound spots were visualized by UV light (254 nm) and/or by staining with yellow solution containing $Ce(NH_4)_2(NO_3)_6$ (0.5 g) and $(NH_4)_6Mo_7O_{24} \cdot 4H_2O$ (24.0 g) in 6% $H_2SO_4$ (500 mL). Flash column chromatography was performed on silica gel 60 Geduran (35–75 μm, EM Science). $^1$H NMR spectra were recorded on a Bruker AMX-400 or a Bruker AMX-500 instrument. Low and high resolution mass spectra were recorded under fast atom bombardment (FAB) conditions. HPLC measurements were performed on HITACHI HPLC D-7000 system equipped with UV detector L7400, pump L7100 and software D-7000. All the experiments were performed by using a normal phase column 86-100-D5 (MICROSORB-MV™, RAININ INST. COMPANY INC.) with the solvent system hexane-EtOAc.

General procedure for competition experiments. A mixture of two thioglycoside donors (0.01 mmol of each, $D_{ref}$ is the reference donor and $D_x$ is any other donor molecule), absolute MeOH (0.05 mmol) and molecular sieves (AW-300) in dichloromethane (1.0 mL) was stirred at room temperature for 10 min. An aliquot of this mixture (40 μL) was taken and separately injected (10 μL for each injection) into the HPLC in order to determine the baseline separation conditions, and also to measure a coefficient (a) between the absorption (A) and the concentration of the donor molecule [D], a=A/[D]. The solution of 0.5 M NIS in acetonitrile (20 μL, 0.01 mmol) was added to the above mixture, followed by addition of a solution of 0.1 M TfOH (10 μL, 0.001 mmol), and the reaction was left at room temperature for 2 h. The mixture was diluted with dichloromethane (2 mL), filtered, washed with saturated aqueous sodium thiosulfate containing 10% sodium hydrogen bicarbonate, dried ($Na_2SO_4$) and concentrated to dryness. The residue was dissolved in dichloromethane (1.0 mL) and the concentrations of the remained donors ($[D_x]$ and $[D_{ref}]$) were measured by HPLC using the same conditions (10 μL for each injection) as determined for the mixture before the addition of reagents. The example of such an experiment is given in FIG. 19.

Synthesis of building blocks. Scheme 5 illustrates the representative synthesis of certain building blocks found in the table of FIG. 17.

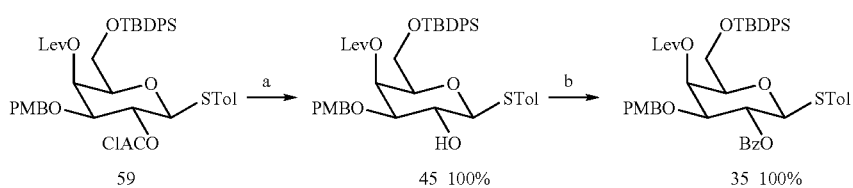

Scheme 5.

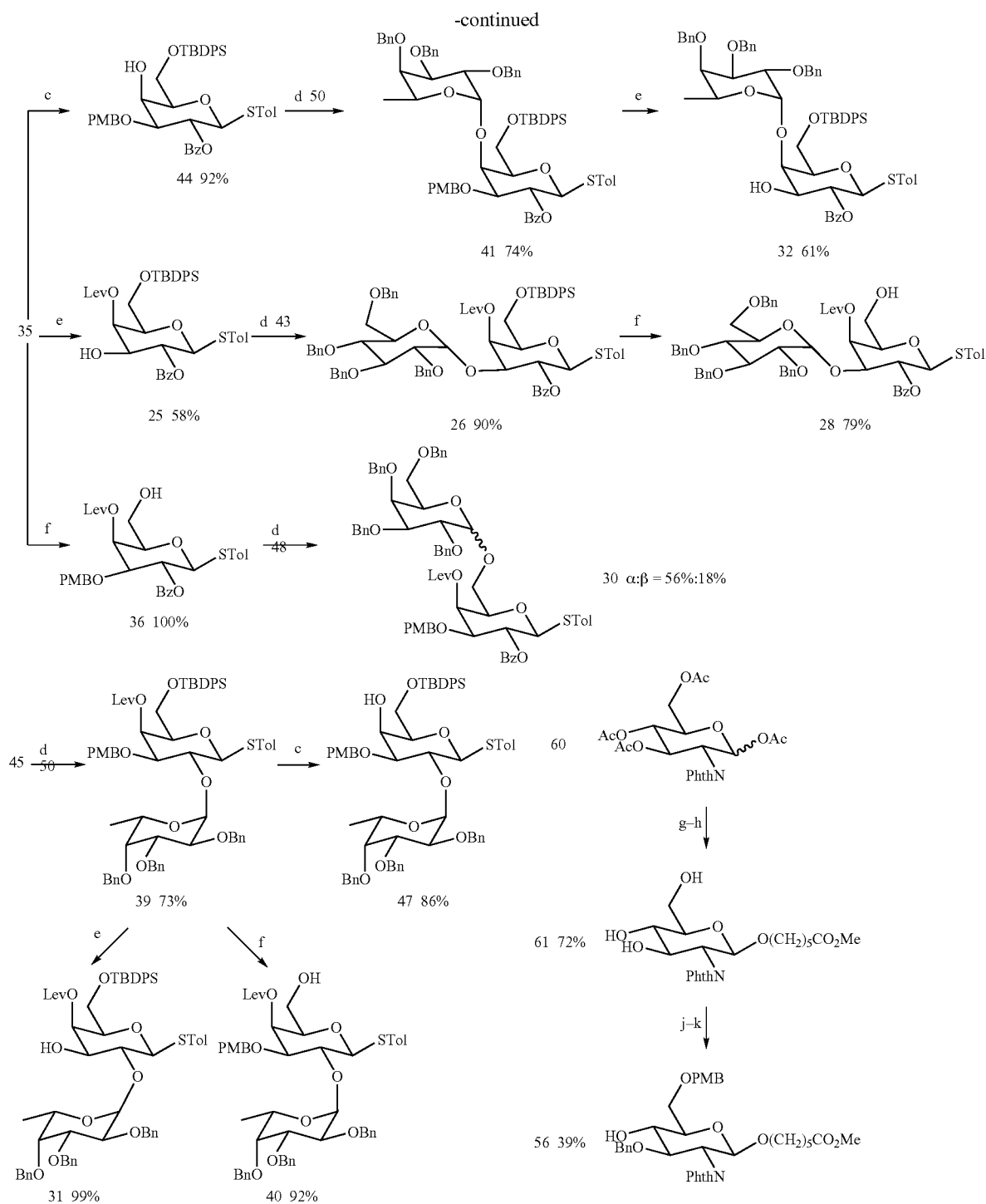

General procedure for glycosylation: To a cold (−40° C.) mixture of glycosyl donor (1.5 equiv.), acceptor (1.0 equiv.), NIS (1.6 equiv.) and MS., was added $CH_2Cl_2$ by syringe, and the mixture was stirred for 20 min, then added TfOH (0.015 equiv.). The mixture was stirred at −20° C. for 0.5 h, then gradually raised to room temperature. The reaction was monitored by TLC. After the reaction is finished, solid $Na_2SO_3$, $NaHCO_3$ and few drops of water were added into the reaction mixture and the mixture was stirred for 5 min, diluted with $CH_2Cl_2$, filtered, washed with sat. $NaHCO_3$ and brine, dried over $Na_2SO_4$ (or $MgSO_4$) and concentrated. The residue was chromatographed to give the named compounds.

p-Methylphenyl 2,3,4,6-Tetra-O-acetyl-1-thio-α-D-mannopyranoside (1):

To a mixture of D-mannose pentaacetate (16.0 g, 0.041 mol) and p-thiocresol (7.6 g, 0.0615 mol) in $CH_2Cl_2$ (200 mL), boron trifluoride diethyl etherate (6.8 mL, 0.0533 mol)

was added. The mixture was stirred overnight. The reaction mixture was then diluted with $CH_2Cl_2$ (200 mL), washed with sat. $NaHCO_3$ (2×120 mL) and water (100 mL). The organic layer was dried over $Na_2SO_4$. The solvent was removed, and the residue was purified by column chromatography on silia gel (hexanes/EtOAc 3:1) to give product (16.2 g, 87%) as a syrup: $^1$HNMR (500 MHz, $CDCl_3$), δ 7.38 (d, J=8.0 Hz, 2H), 7.12 (d, J=8.0 Hz, 2H), 5.49 (dd, 1H, J=2.5, 1.5 Hz), 5.42 (d, 1H, J=1.0 Hz), 5.30–5.35 (m, 2H), 4.54–4.58 (m, 1H), 4.30 (dd, 1H, J=12.5, 6.0 Hz), 4.11 (dd, 1H, J=12.0, 2.5 Hz), 2.33 (s, 3H), 2.15 (s, 3H), 2.08 (s, 3H), 2.06 (s, 3H), 2.02 (s, 3H); HRMS (M+Cs) calcd for $C_{21}H_{26}O_9SCs$ 587.0352. found 587.0331.

p-Methylphenyl 2,3,6-Tri-O-benzoyl-4-O-(2,3,4,6-tetra-O-benzoyl-β-D-galactopyranosyl)-β-D-glucopyranoside (2):

Peracetylated lactoside 6 (ibid, Balavoine, G. et al 1995) (2 g, 2.695 mmol) was dissolved in anhydrous methanol (25 mL) and the solution of 25% NaOMe in methanol (w/v, 0.5 mL) was added dropwise. After stirring at room temperature for 0.5 h, the solution was neutralized by Amberlite HR-120 ($H^+$), filtered and concentrated. The residue was dissolved in dry pyridine (10 mL) and treated with excess benzoylchloride (3 mL) and p-dimethylamino pyridine (100 mg) for 5 h at 50° C. The mixture was evaporated to dryness under reduced pressure and the residue was diluted with $CH_2Cl_2$ (250 mL), washed with saturated aq. $NaHCO_3$, brine, dried over $Na_2SO_4$, filtered and concentrated. The residue was chromatographed (Hexane/EtOAc, 4:1) to give 2 (3.06 g, 96%): $[α]_D22$ +37.8° (c, 0.5, $CHCl_3$); ($^1$H-NMR (500 MHz, $CDCl_3$), δ 2.23 (S, 3H), 3.69 (d, 2H, J=6.5 Hz), 3.88 (ddd, 1H, J=10.0, 4.5 and 1.5 Hz), 3.93 (t, 1H, J=6.5 Hz, H4), 4.18 (t, 1H, J=9.5 Hz), 4.51 (dd, 1H, J=12.0 and 5.0 Hz), 4.67 (dd, 1H, J=12.0 and 1.5 Hz), 4.85 (d, 1H, J=10.0 Hz), 4.89 (d, J=8.0 Hz), 5.42 (dd, 1H, J=9.5 and 1.5 Hz), 5.43 (dd, 1H, J=10.0 and 4.5 Hz), 5.74 (dd, 1H, J=10.0 and 7.5 Hz), 5.76 (d, 1H, J=3.0 Hz), 5.82 (t, 1H, J=9.5 Hz), 6.90 (d, 2H, J=8.0 Hz), 7.11–7.61 (m, 24H), 7.73 (d, 2H, J=8.0 Hz), 7.9–8.0 (m, 12H); HRMS for $C_{68}H_{56}O_{17}SCs$ (M+Cs) calcd 1309.2293. found 1309.2222.

p-Methylphenyl 3,6-Di-O-benzoyl-2-deoxy-2-phthalimido-1-thio-β-D-glucopyranoside (8):

p-Methylphenyl 2-deoxy-2-phthalimido-1-thio-β-D-glucopyranoside (ibid, Balavoine, G. et al. 1995) (185 mg, 0.44 mmol) in $CH_2Cl_2$ (8 mL) was treated with benzoylchloride (203 μL, 1.76 mmol) and pyridine (177 μL, 2.2 mmol) (see 2). The residue was purified by flash chromatography (Hexane/EtOAc, 3:1) to give the title compound (205 mg, 75%) as a white solid: $[α]_D22$ +107° (c, 0.1, $CHCl_3$); 1H-NMR (400 MHz, CDCl3), δ 2.02 (s, 3H), 3.70 (s, 1H), 3.86 (t, 1H, J=9.4 Hz), 4.03 (m, 1H), 4.47 (t, 1H, J=10.4 Hz), 4.70 (dd, 1H, J=12.1, 5.1 Hz), 4.78 (dd, 1H, J=12.0, 4.0 Hz), 5.83 (d, 1H, J=10.4 Hz), 5.99 (dd, 1H, J=10.2, 9.1 Hz), 7.23–8.08 (m, 8H); 13C-NMR (400 MHz, CDCl3) δ 21.10, 53.44, 63.71, 70.01, 74.69, 78.21, 83.05, 123.54, 127.30, 128.29, 128.33, 128.63, 129.51, 129.69, 129.78, 129.83, 131.07, 131.43, 133.16, 133.40, 133.59, 134.13, 134.26, 138.29, 166.65, 166.87, 167.14, 167.89; HRMS for $C_{35}H_{29}NO_8SCs$ (M+Cs) calcd 756.0668. found 756.0690.

p-Methylphenyl 2,3,6-Tri-O-Benzoyl-4-O-(2,3,4,6-tetra-O-benzoyl-β-D-galactopyranosyl)-β-D-glucopyranoside (9):

The glycosylation of donor 48 (151.2 mg, 0.234 mmol) and the acceptor 10 (100 mg, 0.167 mmol) were performed under general procedure as described above. Chromatography of the crude material gave the title compound 9 (121 mg, 65%) as white solid, and succinimide directive 58 (22 mg, 15% of the donor 48) as a byproduct. Data for 9: $[α]_D22$ +26.8° (c, 0.5, $CHCl_3$); $^1$H-NMR (500 MHz, $CDCl_3$), δ 2.25 (S, 3H, Me of STol), 3.38 (m, 2H), 3.76 (dd, 1H, J=10.5 and 4.0 Hz), 3.84 (dd, 1H, J=10.5 and 2.5 Hz), 3.90–4.0 (m, 3H), 4.17 (t, 1H, J=9.5 Hz), 4.19 (d, 1H, J=11.5 Hz), 4.23 (d, 1H, J=12.0 Hz), 4.28 (d, 1H, J=12.0 Hz), 4.41 (d, 1H, J=11.0 Hz), 4.56 (dd, 1H, J=12.0 and 4.5 Hz), 4.59 (d, 2H, J=2.5 Hz), 4.77 (d, 1H, J=11.5 Hz), 4.87 (d, 1H, J=12.0 Hz), 4.94 (dd, 1H, J=12.0 and 2.0 Hz), 4.99 (d, 2H, J=3.5 Hz), 5.36 (t, 1H, J=10.0 Hz), 5.85 (t, 1H, J=7.5 Hz), 6.88 (d, 2H, J=8.0 Hz), 7.05–7.52 (m, 35H), 7.63 (t, 1H, J=7.0 Hz), 7.92 (d, 2H, J=8.0 Hz), 7.95 (d, 2H, J=8.0 Hz), 8.02 (d, 2H, J=8.0 Hz); HRMS for $C_{68}H_{64}O_{13}SCs$ (M+Cs) calcd 1253.3122. found 1253.3056. Anal. Calcd for $C_{68}H_{64}O_{13}S$: C, 72.94; H, 5.75; S, 2.86. Found C, 72.94; H, 5.60; S, 3.25. Data for 58: $^1$H-NMR (500 MHz, $CDCl_3$), δ 2.51–2.64 (m, 4H), 3.42 (dd, 1H, J=9.5 and 7.0 Hz), 3.49 (dd, 1H, J=9.5 and 6.0 Hz), 4.03 (d, 1H, J=2.5 Hz), 4.36–4.49 (m, 5H), 4.55 (dd, 1H, J=10.0 and 3.0 Hz), 4.57 (d, 1H, J=9.0 Hz), 4.67 (d, 1H, J=11.5 Hz), 4.75 (d, 1H, J=11.5 Hz), 4.82 (d, 1H, J=11.5 Hz), 4.94 (d, 1H, J=11.5 Hz), 6.13 (d, 1H, J=7.5 Hz), 7.20–7.37 (m, 20H); HRMS for $C_{38}H_{39}O_7NCs$ (M+Cs) calcd 754.1781. found 754.1763.

p-Methylphenyl 2,3,6-Tri-O-benzoyl-1-thio-β-D-glucopyranoside (10):

The title compound was prepared from peracetylated glucoside 5 (ibid, Magnusson, G. J. 1977) by the following five-step synthesis:

1). Compound 5 (2.2 g, 4.8 mmol) was treated with 1M NaOMe in methanol (0.5 mL) in anhydrous methanol (35 mL) by the procedure described in the preparation of 2.

2). The residue was dissolved in dry acetonitrile (20 mL) and p-anisaldehyde dimethylacetal (1.3 g, 7 mmol) and camphorsulfonic acid (100 mg) were added. After stirring at room temperature for 2 h, the mixture was neutralized by adding pyridine, then evaporated to dryness.

3). The residue was treated with excess benzoyl chloride (1.64 mL, 13.6 mmol) and 4-dimethylamino pyridine (0.5 g) in dry pyridine (10 mL) for 2 h at 50° C. (see 2). The residue was crystallized from ethylacetate and hexane to afford the 2,3-benzoyl-4,6-p-methoxybenzylydine product as white crystals (2.4 g, 83% yield for three steps): m.p. 202–203° C.; $^1$H-NMR (500 MHz, $CDCl_3$), δ 2.34 (S, 3H, Me of STol), 3.73 (ddd, 1H, J=14.0, 9.5 and 4.5 Hz, H5), 3.75 (s, 3H, OMe), 3.83–3.88 (m, 2H), 4.43 (dd, 1H, J=10.5 and 4.5 Hz), 4.96 (d, 1H, J=10.0 Hz, H-1), 5.44 (t, 1H, J=9.5 Hz), 5.49 (s, 1H), 5.77 (t, 1H, J=9.5 Hz), 6.83 (d, 2H, J=9.0 Hz), 7.12 (d, 2H, J=8.0 Hz), 7.25–7.41 (m, 8H), 7.47 (t, 1H, J=7.5 Hz), 7.53 (t, 1H, J=7.5 Hz), 7.93 (d, 2H, J=8.0 Hz), 7.97 (d, 2H, J=8.0 Hz); HRMS for $C_{35}H_{32}O_8SCs$ (M+Cs): calcd 745.0872. found 745.0849.

4). The above mentioned benzylidene derivative (2.0 g, 3.27 mmol) was suspended in 80% acetic acid-water (v/v, 25 mL) and the reaction was stirred at 50° C. for 1 h. The mixture was evaporated to dryness. The residue was dissolved in dry toluene (20 mL) and evaporated again to dryness. This procedure was repeated three times.

5). The crude residue was then dissolved in dichloromethane (20 mL) followed by addition of triethylamine (3 mL) and benzoylchloride (0.57 mL, 4.95 mmol). After 1 h at room temperature, the reaction was quenched by addition of ethyl acetate and water and the mixture was evaporation to dryness. The product was crystallized from ethylacetate and hexane to afford 10 (1.5 g, 77%) as white crystals: $[α]_D22$ +56° (c, 0.5, $CHCl_3$); $^1$H-NMR (500 MHz, $CDCl_3$), m.p. 197° C.; δ 2.28 (s, 3H), 3.46 (d, 1H, J=4.0

Hz), 3.84–3.86 (m, 2H), 4.72–4.76 (m, 2H), 4.89 (d, 1H, J=10.0 Hz, H-1), 5.37 (t, 1H, J=9.5 Hz), 5.47 (t, 1H, J=9.0 Hz), 6.96 (d, 2H, J=8.0 Hz), 7.31–7.40 (m, 6H), 7.47–7.54 (m, 4H), 7.63 (t, 1H, J=7.5 Hz), 7.93 (d, 2H, J=8.0 Hz), 7.98 (d, 2H, J=8.0 Hz), 8.09 (d, 2H, J=8.0 Hz). HRMS for $C_{34}H_{30}O_8SCs$ (M+Cs) calcd 731.0716. found 731.0689. Anal. Calcd for $C_{34}H_{30}O_8S$: C, 68.21; H, 5.05; S, 5.36. Found C, 68.79; H, 5.06; S, 5.13.

p-Methylphenyl 3,4,6-Tri-O-acetyl-2-deoxy-2-phthalimido-1-thio-β-D-galactopyranoside (11):

1,3,4,6-Tetra-O-acetyl-2-deoxy-2-phthalimido-β-D-galactopyranose (Nilsson, U. et al. *Carbohydr. Res.* 1990, 208, 260) (1.7 g, 3.56 mmol) in $CH_2Cl_2$ (20 mL) was treated with thiocresol (663 mg, 5.34 mmol) and $BF_3.Et_2O$ (1.5 mL) by the procedure described in the preparation of 1. After workup, the crude product was crystallized from $Et_2O$. to gave the title compound 11 (1.62 g, 83%): m.p. 141–142° C.; $[\alpha]_D22$ +45.4° (c, 0.5, $CHCl_3$); $^1$H-NMR (400 MHz, $CDCl_3$), δ 1.97 (s, 3H), 2.05 (s, 3H), 2.08 (s, 3H), 2.31 (s, 3H), 4.09–4.24 (m, 3H), 4.62 (t, 1H, J=10.8 Hz), 5.49 (d, 1H, J=3.2 Hz), 5.64 (d, 1H, J=10.8 Hz), 5.80 (dd, 1H, J=10.8, 3.2 Hz), 7.07 (d, 2H, J=8.1 Hz), 7.32 (d, 2H, J=8.1 Hz), 7.76–7.80 (m, 4H); $^{13}$C-NMR (400 MHz, $CDCl_3$) δ 20.52, 20.69, 21.14, 50.11, 61.63, 66.85, 68.81, 74.48, 84.35, 123.65, 129.62, 133.21, 134.40, 162.01, 163.10, 167.16, 167.90, 171.22; HRMS for $C_{27}H_{27}NO_9SCs$ (M+Cs) calcd 674.0461. found 674.0435.

p-Methylphenyl 3-O-Acetyl-6-O-benzoyl-2-dexy-2-phthalimido-1-thio-β-D-glucopyranoside (12):

p-Methylphenyl 2-deoxy-2-phthalimido-1-thio-β-D-glucopyranoside (ibid, Balavoine, G. et al 1995) (420 mg, 1.01 mmol) was treated with camphorsulfonic acid (30 mg) and anisaldehyde dimethylacetale (0.2 mL, 1.2 mmol) (see the preparation of 5). The residue in pyridine (2 mL) was cooled to 0° C., acetic anhydride (0.3 mL, 3 mmol) was added and the reaction was stirred for 1.5 h. After workup, the mixture in HOAc/water (1:1, 20 mL) was heated at 60° C. for 30 min. After cooling to room temperature, the reaction mixture was evaporated to dryness. The residue was dissolved in $CH_2Cl_2$ (20 mL) and washed with saturated aq. $NaHCO_3$ and $NH_4Cl$, dried over $MgSO_4$ and the solvent removed under reduced pressure. This material, without further purification, was treated with pyridine (2 mL) and benzoylchloride (121 μL, 1.05 mmol) at 0° C. for 30 min, then evaporated to dryness. The residue was purified by flash chromatography (Hexane/EtOAc, 2:1) to give 12 (340 mg, 60% over four steps) as white white solid: $[\alpha]_D22$ −8.6° (c, 0.5, $CHCl_3$); $^1$H-NMR (400 MHz, $CDCl_3$), δ 1.88 (s, 3H), 2.24 (s, 3H), 3.51 (m, 1H), 3.71 (t, 1H, J=8.0 Hz), 3.96 (m, 1H), 4.27 (t, 1H, J=10.3 Hz), 4.63–4.75 (m, 2H), 5.76 (m, 1H), 5.80 (d, 1H, J=10.4 Hz), 6.94 (d, 2H, J=8.0 Hz), 7.32 (d, 2H, J=8.1 Hz), 7.60–7.74 (m, 3H), 7.81–7.87 (m, 2H), 8.05–8.08 (?); 13C-NMR (400 MHz, CDCl3), δ 20.56, 21.06, 53.54, 63.64, 69.42, 74.07, 77.97, 82.72, 123.53, 127.13, 128.26, 128.33, 129.45, 129.60, 129.72, 129.78, 131.02, 131.46, 133.20, 133.59, 134.20, 134.37, 138.25, 166.67, 167.16, 167.90, 171.22; HRMS for $C_{30}H_{27}NO_8SClCs$ (M+Cs) calcd 694.0512. found 694.0537.

p-Methylphenyl 2,3,4-Tri-O-benzoyl-1-thio-β-D-galactopyranoside (13):

Compound 16 (3.6 g, 5.06 mmol) was treated with the mixture of $CH_3CN$-(aq)HF (90:10, 100 mL) for 1 h. The solution was then concentrated and the residue diluted with $CH_2Cl_2$ (300 mL), washed with saturated $NaHCO_3$ (2×150 mL), dried ($Na_2SO_4$), filtered and concentrated. The residue was purified by flash chromatography (Hexane/EtOAc, from 2:1 to 1:2) to give 13 (2.92 g, 96.8%): $[\alpha]_D22$ +112.6° (c, 1, $CHCl_3$); $^1$H-NMR (400 MHz, $CDCl_3$), δ 8.01–7.14 (19H), 5.83 (d, 1H, J=3.16 Hz, H-4), 5.77 (t, 1H, J=9.92 Hz, H-2), 5.67 (dd, 1H, J=3.16 and 9.88 Hz, H-3), 4.968 (d, 1H, J=9.88 Hz, H-1), 4.08(t, 1H, J=6.68 Hz, H-5), 3.85 (dd, 1H, J=6.68 and 11.88 Hz, H-6), 3.85 (dd, 1H, J=6.68 and 11.88 Hz, H-6); $^{13}$C-NMR (400 MHz, $CDCl_3$), δ 166.47, 165.45, 165.13, 85.73, 77.76, 73.10, 68.91, 67.95, 60.6821.31; HRMS for $C_{34}H_{30}O_8Cs$ (M+Cs) calcd 731.0716. found 731.0736.

p-Methylphenyl 3,4,6-Tri-O-benzoyl-1-thio-β-D-galactopyranoside (15):

A suspended mixture of p-Methylphenyl 1-thio-β-D-galactopyranoside (Vargas-Berenguel, A. et al. *J. Chem. Soc. Perkin Trans* 1 1994, 3287) (100 mg, 0.350 mmol) and $Bu_2SnO$ (266 mg, 1.04 mmol) in toluene-benzene (1:1, 10 mL) was refluxed for 10 min. The mixture was concentrated to a volume of 2 mL by distillation under Ar, then the hot solution (about 100° C.) was treated with benzoyl chloride (130 μL, 1.12 mmol). After being stirred for 1 h at this temperature, the reaction mixture was diluted with EtOAc (20 mL), cooled to room temperature, filtered through Celite and concentrated. Chromatography of the residue (hexane/EtOAc, 4:1 to 2:1 to 1:1) furnished 15 (192 mg, 91.7%) as white white solid: $[\alpha]_D22$ +15° (c, 0.5, $CHCl_3$); $^1$H-NMR (250 MHz, $CDCl_3$), δ 5.91 (d, 1H, J=3.1 Hz, H-4), 5.43 (dd, 1H, J=3.3, 9.7 Hz, H-3), 4.720 (d, 1H, J=9.6 Hz, H-1), 4.29 (bt, 1H, J=6.5 Hz, H-5), 4.62 (dd, 1H, J=6.6 Hz, H-6) 4.37 (dd, 1H each, J=11.5 Hz, H-6'), 4.03 (t, 1H, J=9.6 Hz, H-2), 2.38 (s, 3H, Me); $^{13}$C-NMR (270 MHz, $CDCl_3$) δ 165.98, 165.90, 165.29, 88.26, 74.97, 74.47, 68.59, 67.34, 62.45, 21.28; HRMS for $C_{40}H_{44}O_8SiCs$ (M+Cs) calcd 845.1581. found 845.1609.

p-Methylphenyl 2,3,4-Tri-O-benzoyl-6-O-t-butyldimethyl-silyl-1-thio-β-D-galactopyranoside (16):

A solution of p-Methylphenyl 1-thio-β-D-galactopyranoside (ibid, Vargas-Berenguel, A. et al. 1994) (4.0 g, 14.0 mmol) in DMF (10 mL) was treated with imidazole (1.4 g, 20.6 mmol) and t-butyldimethylsilyl chloride (2.26 g, 14.5 mmol) at 0° C. for 12 h. The mixture was evaporated under reduced pressure and the residue was purified by flash chromatography (Hexane/EtOAc, from 4:1 to 1:1) to give the corresponding 6-O-t-butyldimethylsilyl ether (5.3 g, 96%) as syrup. Part of this product (4.0 g, 10.0 mmol) was treated with pyridine (50 mL), excess of benzoyl chloride (8 mL) and 4-dimethylamino pyridine (100 mg) at 50° C. for 1 h. After workup, the residue was purified by chromatography on a silica gel column (Hexane/EtOAc, 4:1) to afford the title compound 16 (6.96 g 97.7%) as syrup: $[\alpha]_D22$ +102° (c, 0.8, $CHCl_3$); $^1$H-NMR (400 MHz, $CDCl_3$), δ 5.93 (d, 1H, J=3.2, H-4), 5.66 (t, 1H, J=9.84 Hz, H-2), 5.56 (dd, 1H, J=3.24, 9.96 Hz, H-3), 4.935 (d, 1H, J=9.80 Hz, H-1), 4.05 (bt, 1H, J=7.08 Hz, H-5), 3.85 (dd, 1H, J=5.92, 10.0 Hz, H-6), 3.85 (dd, 1H, J=7.52, 10.0 Hz, H-6); $^{13}$C-NMR (400 MHz, $CDCl_3$) δ 165.52, 165.21, 165.09, 86.09, 73.32, 68.12, 67.95, 60.96, 25.77, 25.73, 21.34, −5.60, −5.70; HRMS for $C_{40}H_{44}O_8SiCs$ (M+Cs) calcd 845.1581. found 845.1609.

p-Methylphenyl 4,6-O-Benzylidine-2-deoxy-2-phthalimido-1-thio-β-D-glucopyranoside (17).

p-methylphenyl 2-deoxy-2-phthalimido-1-thio-β-D-glucopyranoside (ibid, Balavoine, G. et al. 1995) (820 mg, 1.98 mmol) was treated with benzaldehyde dimethylacetale (385 μL, 2.56 mmol) and camphorsulfonic acid (50 mg) in dry $CH_3CN$ (20 mL) as the procedure described for the preparation of 5. The residue was crystallized from EtOH (−25° C.) to give 17 (780 mg, 79%) as white crystals: m.p. 121–122° C.; [α]$_D$22 +34° (c, 0.5, CHCl$_3$); $^1$H-NMR (400 MHz, CDCl$_3$), δ 7.75–7.06 (13H), 5.624 (d, 1H, J=10.52 Hz, H-1), 5.60 (dd, 1H, J=2.96, 9.48 Hz, H-3), 4.39 (dd, 1H, J=4.76, 10.48 Hz, H-6), 4.30 (t, 1H, J=10.16 Hz, H-2), 3.81 (t, 1H, J=10.16 Hz, H-6), 3.67 (dd, 1H, J=4.88, 9.80 Hz, H-5), 3.58 (t, 1H, J=9.16 Hz, H-4), 2.29 (s, 3H, Me); $^{13}$C-NMR (400 MHz, CDCl$_3$) δ 101.93, 84.43, 81.88, 70.24, 69.71, 68.55, 55.57, 21.12; HRMS for C$_{28}$H$_{25}$NO$_6$SCs (M+Cs) calcd 636.0457. found 636.0475.

p-Methylphenyl 2-Azido-4,6-O-benzylidene-3-O-chloroacetyl-2-dexoy-1-thio-β-D-glalactopyranoside (18):

The tittle compound was prepared from p-methylphenyl 2-dexoy-2-azido-1-thio-β-D-galalactopyranoside (Luening, B. et al. *Glycoconjugate J.* 1989, 6, 5–19) (527 mg, 1.70 mmol), benzaldehyde dimethylacetale (280 μL, 1.87 mmol) and camphorsulfonic acid (30 mg, 0.15 mmol) in dry CH$_3$CN (15 mL) as described above. Flash chromatography of the crude residue (Hexane/EtOAc, 2:1) gave the corresponding 4,6-O-benzylidine derivative 18a (584 mg, 86%) as white solid:

$^1$H-NMR (400 MHz, CDCl$_3$), δ 2.34 (s, 3H), 3.39 (s, 1H), 3.49 (t, 1H, J=7.6 Hz), 3.57 (m, 1H), 3.94 (dd, 1H, J=10.0, 1.2 Hz), 4.05 (d, 1H, J=3.5 Hz), 4.31 (d, 1H, J=9.5 Hz), 4.32 (m, 1H), 7.32 (d, 2H, J=8.1 Hz), 7.60–7.74 (m, 5H), 7.81–7.87 (m, 2H); $^{13}$C-NMR (400 MHz, CDCl$_3$) δ 21.10, 61.70, 69.0, 69.5, 72.8, 79.2, 84.8, 101.1, 126.2, 126.5, 128.1, 129.2, 129.6, 134.5, 137.3, 138.5; HRMS for C$_{20}$H$_{21}$N$_3$O$_4$SNa (M+Na) calcd 422.1150. found 422.1134.

The above mentioned 4,6-O-benzylidine derivative (212 mg, 0.53 mmol) was dissolved in dry pyridine (5 mL) and cooled to 0° C. The mixture was treated with chloroacetyl chloride (47.8 μL, 0.6 mmol) and the reaction progress was monitored by TLC. After being stirred for 20 min at room temperature, the solvent was removed by evaporation under a high vacuum and the residue was purified on a silica gel column (Hexane/EtOAc, 2:1) to afford 18 (247 mg, 98%) as white white solid: [α]$_D$22 −28° (c, 0.5, CHCl$_3$); $^1$H-NMR (400 MHz, CDCl$_3$) δ 2.34 (s, 3H), 3.56 (m, 1H), 3.81 (t, 1H,=10.1 Hz), 4.00 (dd, 1H, J=12.4, 1.6 Hz), 4.08 (AB$_q$, 2H, J=12.2 Hz), 4.36 (dd, 1H, J=3.4, 0.8 Hz), 4.39 (dd, 1H, J=12.4, 1.7 Hz), 4.45 (d, 1H, J=9.8 Hz), 4.84 (dd, 1H, J=10.8, 3.4 Hz), 5.47 (s, 1H), 7.05–7.07 (m, 2H), 7.37–7.40 (m, 5H), 7.60–7.62 (m, 2H); $^{13}$C-NMR (400 MHz, CDCl$_3$) δ 21.25, 40.45, 58.08, 69.11, 69.38, 72.27, 76.68, 85.21, 100.92, 125.77, 126.42, 128.16, 129.28, 129.58, 134.72, 137.32, 138.35, 166.83; HRMS for C$_{22}$H$_{22}$N$_3$O$_5$SClNa (M+Na) calcd. 498.0866. found 498.0882.

p-Methylphenyl 2,4,6-Tri-O-benzoyl-1-thio-β-D-galactopyranoside (19):

Compound 13 (300 mg, 0.502 mmol) was dissolved in the mixture of pyridine-H$_2$O (4:1, 3 mL) to which AgF (30 mg) was added and the mixture was stirred at 50° C. for 20 min. The reaction mixture was concentrated under reduced pressure and the residue was chromatographied (Hexane/EtOAc, 2:1) to give 19 (96 mg, 32%) as white powder: [α]$_D$22 −10.4° (c, 0.5, CHCl$_3$); $^1$H-NMR (400 MHz, CDCl$_3$) δ 8.11–7.02 (19H), 5.77 (d, 1H, J=3.36 Hz, H-4), 5.26 (t, 1H, J=9.64 Hz, H-2), 4.879 (d, 1H, J=9.88 Hz, H-1), 4.58 (dd, 1H, J=7.24, 11.56 Hz, H-6), 4.45 (dd, 1H, J=5.44, 11.60 Hz, H-6), 3.85 (bt, 1H, J=6.44 Hz, H-5), 4.15 (dq, 1H, J=3.56, 6.28 and 9.64 Hz, H-3), 2.77 (d, 1H, J=6.24 Hz, OH), 2.34 (s, 3H, Me); HRMS for C$_{34}$H$_{30}$O$_8$SCs (M+Cs) calcd 731.0716. found 731.0737. Anal. Calcd for C$_{34}$H$_{30}$O$_8$S: C, 68.21; H, 5.05; S, 5.36. Found: C, 67.65; H, 4.96; S, 5.45.

p-Methylphenyl 4,6-O-Benzylidine-2,3di-O-chloroacetyl-1-thio-β-D-galactopyranoside (20):

p-Methylphenyl 1-thio-β-D-galactopyranoside (ibid, Vargas-Berenguel, A. 1994) (3.5 g, 12.24 mmol) was suspended in CH$_3$CN (30 mL), and treated with benzaldehyde dimethylacetal (9.35 mL, 18.36 mmol) and camphorsulfonic acid (100 mg). The mixture was stirred at room temperature until all the starting material had been consumed (2 h). After evaporation of the solvent, the crude product was crystallized from MeOH to afford the corresponding 4,6-O-benzylidine derivative (3.8 g, 83%). Part of this product (200 mg, 0.535 mmol) was dissolved in CH$_2$Cl$_2$ (5 mL) and treated with pyridine (300 μL) and chloroacetyl chloride (153 μL, 1.91 mmol). After usual workup, the crude product was purified by chromatography (Hexane/EtAc, 1:1) to give title compound 20 (276 mg, 98%) as white solid: [α]$_D$22 −1° (c, 0.5, CHCl$_3$); $^1$H-NMR (500 MHz, CDCl$_3$) δ 7.49 (d, 2H, J=8.0 Hz), 7.09 (d, 2H, J=8.0 Hz), 5.45 (s, 1H), 5.24 (t, 1H, J=10.0 Hz), 5.08 (dd, 1H, J=3.5, 12.4 Hz), 4.68 (d, 1H, J=10.0 Hz), 4.4 (m, 2H), 4.11–4.01 (m, 6H), 3.62 (s, 1H), 2.35 (s, 3H); HRMS for C$_{24}$H$_{24}$Cl$_2$O$_7$SCs (M+Cs) calcd 658.9674. found 658.9692.

p-Methylphenyl 3,4,6-Tri-O-acetyl-2-deoxy-2-(2,2,2-trichloroethoxylcarbonylamino)-1-thio-β-D-glucopyranoside (21):

The tittle compound was prepared from 1,3,4,6-tetra-O-acetyl-2-deoxy-2-(2,2,2-trichloroethoxylcarbonylamino)-β-D-glucopyranose (Boullanger, P. et al *Carbohydr. Res.* 1990, 202, 151) (11.8 g, 22.5 mmol), thiocresol (3.07 g, 24.75 mmol) and BF$_3$-Et$_2$O (10 mL) in dry CH$_2$Cl$_2$ (60 mL) by the procedure described above (see compound 1) The crude product was crystallization from ether to give 21 (11.8 g, 89%) as white crystals: m.p. 175–176° C.; [α]$_D$22 +3° (c, 0.5, CHCl$_3$); $^1$H-NMR (400 MHz, CDCl$_3$) δ 2.00 (s, 3H), 2.01 (s, 3H), 2.09 (s, 3H), 2.35 (s, 3H), 3.71–3.73 (m, 1H), 4.11–4.25 (m, 2H), 4.73 (d, 1H, J=12.0 Hz), 4.79 (d, 1H, J=10.8 Hz), 5.01 (t, 1H, J=9.8 Hz), 5.26 (d, 1H, J=9.8 Hz), 5.31 (d, 1H, J=9.1 Hz), 7.11 (d, 2H, J=8.0 Hz), 7.41 (d, 2H, J=8.0 Hz); $^{13}$C-NMR (400 MHz, CDCl$_3$); δ 20.56, 20.61, 20.73, 21.15, 54.93, 62.25, 68.44, 73.14, 74.47, 75.70, 86.65, 95.36, 127.84, 129.71, 133.62, 138.70, 153.85, 169.45, 170.61; HRMS for C$_{22}$H$_{26}$NO$_9$SCl$_3$Na (M+Na) calcd 610.0266. found 610.0286. Anal. Calcd for C$_{22}$H$_{26}$NO$_9$SCl$_3$: C, 45.03; H, 4.47; N, 2.39. Found: C, 45.46; H, 4.26; N, 2.30.

p-Methylphenyl 2,3,6-Tri-O-benzoyl-1-thio-β-D-galactopyranoside (22):

Compound 33 (200 mg, 0.342 mmol) was dissolved in a mixture of TFA-CH$_2$Cl$_2$ (1:1, 5 mL) and stirred for 1 h. The reaction mixture was diluted with CH$_2$Cl$_2$ (50 mL), washed with saturated NaHCO$_3$, dried over Na$_2$SO$_4$, filtered and concentrated. The residue was further treated with BzCl (56 μl, 0.479 mmol) and pyridine. After general workup, the residue was chromatographed (Hexanes/AcOEt, 3:2) to give 22 (153 mg, 85%); $^1$H-NMR (500 MHz, CDCl$_3$), δ 8.16–6.95 (19H), 5.80 (t, 1H, J=10.0 Hz, H-2), 5.38 (dd, 1H, J=3.0 and 10.0 Hz, H-3), 4.920 (d, 1H, J=10.0 Hz, H-1), 4.66 (m, 2H, H-6), 4.40 (d, 1H, J=2.50 Hz, H-4), 4.12 (bt, 1H, J=6.0 Hz, H-5), 2.27 (s, 3H, -Me); $^{13}$C-NMR (500 MHz, CDCl$_3$), δ 166.4, 165.8, 165.3, 87.1, 76.2, 67.9, 67.6, 63.4, 21.1; HRMS (M+Cs) calcd for C$_{34}$H$_{30}$O$_8$SCs 731.0716. found 731.0736.

p-Methylphenyl 4,6-O-Benzylidine-2-deoxy-2-phthalimido-1-thio-β-D-galactopyranoside (23a):

p-Methylphenyl 2-deoxy-2-phthalimido-1-thio-β-D-galactopyranoside 1.5 g (3.91 mmol) in dry CH$_2$Cl$_2$ (15 mL)

was treated with camphorsulfonic acid (30 mg, 0.15 mmol) and benzaldehyde dimethylacetal (0.59 mL, 3.94 m'''ol). Flash chromatography (Hexane/AcOEt 1:2) of the residue gave 23a (1.83 g, 93%) as white white solid;

$^1$H-NMR (500 MHz, CDCl$_3$), δ 2.35 (s, 3H), 3.70 (m, 1H), 4.06 (dd, 1H, J=12.0 Hz, 2.0 Hz), 4.12 (dd, 1H, J=14.5, 7.0 Hz), 4.28 (m, 1H), 4.39–4.51 (m, 3H), 5.56 (s, 1H), 5.61 (d, 1H, J=10 Hz, H-1), 7.07 (d, 2H, J=8.0 Hz), 7.39–7.48 (m, 7H), 7.72–7.87 (m, 4H); HRMS (M+Cs) calcd for C$_{28}$H$_{25}$O$_6$NSCs 636.0457. found 636.0435.

p-Methylphenyl 4,6-O-Benzylidine-3-O-chloroacetyl-2dexoy-2-N-phthalimido-1-thio-β-D-galactopyranoside (23):

Compound 23a (580 mg, 1.15 mmol) was treated with chloroacetyl chloride (238 μL, 3.45 mmol) and pyridine (5 mL) at 0° C. by the procedure described above (see the preparation of 18). The residue was purified by flash chromatography (Hexane/EtOAc, 2:1) to give 23 (647 mg 97%) as white solid; [α]$_D$22 +10° (c, 0.5, CHCl$_3$); $^1$H-NMR (500 MHz, CDCl$_3$), δ 2.34 (s, 3H), 3.75 (s, 1H), 3.82–3.90 (AB$_q$, 2H, J=15 Hz), 4.07 (dd, 1H, J=11.5 Hz, 1.5 Hz), 4.40 (dd, 1H. J=12.5 Hz, 1.5 Hz), 4.51 (d, 1H, J=3.5 Hz), 4.77 (t, 1H, J=10.5), 5.52 (s, 1H), 5.67 (d, 1H, J=10.4 Hz), 5.76–5.79 (dd, 1H, J=11.0 Hz, 3.5 Hz), 7.04 (d, 2H, J=8.0 Hz), 7.38–7.46 (m, 7H), 7.74–7.77 (m, 2H), 7.84–7.89 (m, 2H); $^{13}$C-NMR (500 MHz, CDCl$_3$), δ 21.22, 40.47, 49.33, 69.63, 71.74, 72.57, 82.50, 101.03, 123.49, 123.68, 126.53, 126.57, 126.72, 128.15, 129.18, 129.53, 131.27, 131.46, 134.15, 134.28, 134.32, 137.41, 138.40, 166.79, 166.87, 168.30; HRMS (M+Cs) calcd for C$_{30}$H$_{26}$NO$_7$SClCs 712.0173. found 712.0196.

p-Methylphenyl 2-O-Benzoyl-4,6-O-benzylidine-3-O-chloroacetyl-1-thio-β-D-galactopyranoside (24):

Compound 42 (80 mg, 0.167 mmol) was treated with ClAcCl (27 μL, 0.335 mmol) and pyridine (100 μL) in CH$_2$Cl$_2$ (2 mL). Chromatography (Hexanes-AcOEt 1:1) of the residue gave 24 (87 mg, 94%) as white powder: $^1$H-NMR (500 MHz, CDCl$_3$), δ 8.05–7.04 (14H), 5.54 (t, 1H, J=10.0 Hz, H-2), 5.49 (s, 1H, ArCH), 5.22 (dd, 1H, J=3.5 and 10.0 Hz, H-3), 4.828 (d, 1H, J=10.0 Hz, H-1), 4.45 (d, 1H, J=3.5 Hz, H-4), 4.43 (d, 1H, J=11.0 Hz, H-6), 4.06 (d, 1H, J=11.0 Hz, H-6), 3.98 and 3.89 (d$_{AB}$, 1H each, J=15.0 Hz, ClCH$_2$), 3.67 (bs, 1H, H-5), 2.34 (s, 3H, Me); $^{13}$C-NMR (500 MHz, CDCl$_3$), δ 167.2, 164.8, 101.2, 85.2, 75.0, 73.3, 69.6, 69.1, 67.2, 40.6, 21.05; HRMS (M+Cs) calcd for C$_{29}$H$_{27}$O$_7$ClCs 687.0220. found 687.0235.

p-Methylphenyl 2-O-Benzoyl-6-O-t-butyldiphenylsilyl-4-O-levulinyl-1-thio-β-D-galactopyranoside (25):

To a stirred solution of 35 (1.1 g, 1.3 mmol) in CH$_2$Cl$_2$ (45 mL), trifluoroacetic acid (8 mL) was added at −20° C. After stirring for 20 nm at this temperature, methanol (8 mL) and CH$_2$Cl$_2$ (80 mL) were then added to the reaction mixture, and the mixture was washed with saturated NaHCO$_3$ (3×30 mL) and brine (30 mL), then dried over Na$_2$SO$_4$. After removal of the solvent, the residue was purified by chromatography on a silica gel column (hexanes-EtOAc 2.5:1) to yield 25 (547 mg, 58%) as white solids: $^1$HNMR (500 MHz, CDCl$_3$), δ 8.08 (d, J=7.5 Hz, 2H), 7.66 (t, J=7.5 Hz, 4H), 7.59 (t, 1H, J=7.5 Hz), 7.37–7.48 (m, 8H), 7.33 (d, J=8.0 Hz), 7.02 (d, 2H, J=8.5 Hz), 5.58 (d, 1H, J=3.5 Hz), 5.13 (t, 1H, J=10.0 Hz), 4.76 (d, 1H, J=10.0 Hz), 3.95 (dt, 1H, J=3.0, 8.5 Hz), 3.76–3.82 (m, 2H), 3.66–3.72 (m, 1H), 3.01 (d, 1H, J=8.0 Hz), 2.67–2.79 (m, 2H), 2.42–2.56 (m, 2H), 2.30 (s, 3H), 2.16 (s, 3H), 1.05 (s, 9H); $^{13}$C-NMR (125 MHz, CDCl$_3$), δ 207.7, 172.0, 166.3, 138.1, 135.6, 135.6, 133.2, 133.1, 133.1, 133.0, 130.0, 129.8, 129.8, 129.7, 129.6, 128.9, 128.4, 127.7, 86.7, 77.83, 73.18, 71.58, 70.36, 61.97, 38.41, 29.68, 28.17, 26.75, 21.13, 19.11; HRMS (M+Cs) calcd for C$_{41}$H$_{46}$O$_8$SSiCs 859.1737. found 859.1704. Anal. Calcd for C$_{41}$H$_{46}$O$_8$SSi: C, 67.74; H, 6.38; S, 4.41. Found: C, 68.10; H, 6.46; S, 4.91.

p-Methylphenyl 2-O-Benzoyl-3-O-(2,3,4,6-tetra-O-benzyl-α-D-glucopyranosyl)-6-O-t-butyldiphenylsilyl-4-O-levulinyl-1-thio-β-D-galactopyranoside (26):

Compound 26 was prepared from 25 (60.0 mg) and 43 (80.1 mg) as described in general glycosylation procedure to yield 25 (93.1 mg, 90%): $^1$H-NMR (500 MHz, CDCl$_3$), δ 7.98 (dd, J=8.0 Hz, 1.0 Hz, 2H), 7.63–7.69 (m, 4H), 7.16–7.45 (m, 29H), 7.00 (d, 2H, J=8.0 Hz), 6.79 (dd, 2H, J=8.0, 2.0 Hz), 5.66 (d, 1H, J=3.0 Hz), 5.46 (t, 1H, J=9.0 Hz), 5.16 (d, 1H, J=3.5 Hz), 4.81 (d, 1H, J=11.0 Hz), 4.69 (d, 1H, J=12.0 Hz), 4.59 (d, 2H, J=11.0 Hz), 4.54 (d, 1H, J=11.5 Hz), 4.46 (d, 1H, J=12.0 Hz), 4.36 (d, 1H, J=12.0 Hz), 4.20 (d, 1H, J=11.0 Hz), 4.05–4.07 (m, 1H), 3.80 (dd, 1H, J=9.5, 6.0 Hz), 3.72 (t, 1H, J=6.0 Hz), 3.63–3.69 (m, 4H), 3.39–3.44 (m, 2H), 3.35 (t, 1H, J=9.5 Hz), 3.30 (dd, 1H, J=10.5, 4.0 Hz), 2.39–2.45 (m, 1H), 2.23–2.33 (m, 6H), 1.95 (s, 3H), 1.06 (s, 9H); $^{13}$C-NMR (125 MHz, CDCl$_3$), δ 206.1, 171.6, 165.0, 138.6, 138.5, 138.4, 137.9, 137.9, 135.6, 135.6, 133.1, 133.0, 132.9, 129.8, 129.7, 129.7, 129.6, 129.5, 129.1, 128.6, 128.3, 128.2, 128.2, 127.9, 127.8, 127.7, 127.7, 127.6, 127.5, 127.4, 127.3, 127.3, 127.1, 93.32, 87.08, 81.41, 79.31, 77.96, 77.38, 75.45, 74.28, 73.91, 73.31, 73.17, 70.54, 68.26, 65.31, 62.22, 37.84, 29.66, 29.50, 27.98, 26.76, 21.09, 19.13; HRMS (M+Cs) calcd for C$_{75}$H$_{80}$O$_{13}$SSiCs 1381.4143. found 1381.4077.

p-Methylphenyl 3,6-Di-O-benzoyl-2-deoxy-2-(2,2,2-trichloroethoxylcarbonylamino)-1-thio-β-D-glucopyranoside (27):

Compound 21 (2.0 g, 3.41 mmol) in MeOH (10 mL) was treated with a catalytic amount of 1M NaOMe for 5 h, then neutralized with IR-120 (H$^+$), filtered and concentrated. To a solution of the crude product (610 mg, 1.324 mmol), pyridine (700 μL) and DMAP (50 mg) in CH$_2$Cl$_2$ (20 mL), was added BzCl (338 μL, 2.916 mmol). The mixture was refluxed for 5 h under Ar, then concentrated and coevaporated twice with toluene, diluted with CH$_2$Cl$_2$ (100 mL), washed with 10% aq. H$_2$SO$_4$, brine, and sat. aq NaHCO$_3$, dried over Na$_2$SO$_4$, filtered and concentrated. Column chromatography (Hexane/AcOEt, 2:1 to 1:2) of the residue gave 27 (495 mg, 56%) as white white solid; [α]$_D$22 +28.4° (c, 0.5, CHCl$_3$); $^1$H-NMR (500 MHz, CDCl$_3$), δ 5.50 (d, 1H, J=9.5 Hz, H-3), 5.41 (t, 1H, J=9.5 Hz), 4.844 (d, 1H, J=10.0 Hz, H-1), 4.74–4.64 (m, 3H), 4.55 (d, 1H, J=12.0 Hz, OCH$_2$CCl$_3$), 3.90 (q, 1H, J=10.0 Hz, H-2), 3.79 (m, 2H, H-5, H-4), 3.42 (d, 1H, J=5.0 Hz, OH), 2.27 (s, 3H, Me); HRMS (M+Cs) calcd for C$_{30}$H$_{20}$O$_8$Cl$_3$NSCs 799.9655. found 799.9680.

p-Methylphenyl 2-O-Benzoyl-3-O-(2,3,4,6-tetra-O-benzyl-α-D-glucopyranosyl)-4-O-levulinyl-1-thio-β-D-galactopyranoside (28).

Compound 28 was prepared from 26 (76.0 mg) as described for the preparation of 36, yielding 28 (48.3 mg, 79%): $^1$H-NMR (400 MHz, CDCl$_3$), δ 7.99 (d, J=7.5 Hz, 2H), 7.43 (t, J=7.4 Hz, 1H), 7.36 (d, J=8.0 Hz, 2H), 7.20–7.31 (m, 20H), 7.09 (d, J=8.1 Hz, 2H), 6.84 (d, J=7.5, 2.0 Hz, 2H), 5.48–5.52 (m, 2H), 4.98 (d, J=3.4 Hz, 1H), 4.84 (d, J=10.9 Hz, 1H), 4.74 (d, J=9.9 Hz, 1H), 4.66 (d, J=10.9 Hz, 1H), 4.61 (s, 2H), 4.58 (d, J=11.4 Hz, 1H), 4.42 (d, J=12.0 Hz, 1H), 4.27 (d, J=12.0 Hz, 1H), 4.22 (d, J=11.3 Hz, 1H), 4.04–4.08 (m, 1H), 3.68–3.79 (m, 3H), 3.57–3.63 (m, 2H), 3.38–3.44 (m, 2H), 3.15–3.23 (m, 2H), 2.64 (br. s, 1H), 2.26–2.53 (m, 7H), 2.09 (s, 3H); $^{13}$C-NMR (100 MHz, CDCl$_3$), δ 206.73, 173.55, 165.07, 138.58, 138.44, 138.40, 138.23, 137.77, 133.13, 133.08, 129.77, 129.56, 128.73, 128.29, 128.25, 127.96, 127.80, 127.71, 127.60, 127.51, 127.43, 127.24, 127.14, 94.32, 87.00, 81.46, 78.96, 77.28, 75.44, 74.76, 74.24, 73.31, 73.15, 70.66, 69.04, 69.03, 67.90, 66.20, 60.21, 37.72, 29.63, 27.82, 21.11; HRMS (M+Cs) calcd for C$_{59}$H$_{62}$O$_{13}$SCs 1143.2965. found 1143.2920.

p-Methylphenyl 2-O-Benzyl-4,6-O-benzylidine-3-O-chloroacetyl-1-thio-β-D-galactopyranoside (29):

Compound 49 (200 mg, 0.431 mmol) was treated with chloroacetylchloride (69 μL, 0.862 mmol) and pyridine (2.0 mL). The residue was purified by chromatography (Hexanes/AcOEt, 1:1) to give 29 (229 mg, 98%) as syrup; [α]$_D$22 +27.4° (c, 0.5, CHCl$_3$); $^1$H-NMR (400 MHz, CDCl$_3$), δ 7.63–7.04 (14H), 5.48 (s, 1H, ArCH), 5.01 (dd, 1H, J=3.36 and 9.64 Hz, H-3), 4.81 and 4.50 (d, 1H each, J=10.96 Hz, ArCH$_2$), 4.642 (d, 1H, J=9.5 Hz, H-1), 4.40 (dd, 1H, J=1.5 and 12.5 Hz, H-6), 4.39–4.36 (m, 2H), 4.00–3.79 (m, 4H), 3.50 (bs, 1H, H-5), 2.36 (d, 1H, J=11.0 Hz, OH), 2.35 (s, 3H, Me); $^{13}$C-NMR (500 MHz, CDCl$_3$), δ 166.78, 100.75, 86.35, 77.03, 75.11, 73.60, 73.31, 69.07, 68.96, 40.50, 21.02; HR0MS (M+Cs) calcd for C$_{29}$H$_{29}$O$_6$ClSCs 673.0428. found 673.0457. Anal. Calcd for C$_{29}$H$_{29}$O$_6$ClS: C, 64.38; H, 5.40. Found: C, 64.18; H, 5.32.

p-Methylphenyl 2-O-Benzoyl-6-O-(2,3,4,6-tetra-O-benzyl-β-D-galactopyranosyl)-4-O-levulinyl-3-O-p-methoxybenzyl-1-thio-β-D-galactopyranoside (30):

Compound 30 was prepared from 36 (49.0 mg) and 48 (78.1 mg) as described in the general glycosylation procedure to give 30 (16.2 mg, 18%): $^1$H-NMR (500 MHz, CDCl$_3$), δ 7.97 (d, J=8.0 Hz, 2H), 7.60 (t, J=7.5 Hz, 1H), 7.46 (t, J=7.5 Hz, 2H), 7.19–7.36 (m, 22H), 6.95 (t, J=8.5 Hz, 4H), 6.57 (d, J=9.0 Hz, 2H), 5.50 (d, J=3.0 Hz, 1H), 5.32 (t, J=10.0 Hz, 1H), 4.94 (d, J=12.5 Hz, 1H), 4.92 (d, J=11.5 Hz, 1H), 4.68–4.76 (m, 4H), 4.63 (d, J=11.5 Hz, 1H), 4.46 (d, J=12.5 Hz, 1H), 4.45 (d, J=12.0 Hz, 1H), 4.41 (d, J=7.5 Hz, 1H), 4.40 (d, J=12.0 Hz, 1H), 4.21 (d, J=12.5 Hz, 1H), 3.76–3.92 (m, 5H), 3.70 (s, 3H), 3.50–3.60 (m, 5H), 2.57–2.75 (m, 4H), 2.20 (s, 3H), 2.13 (s, 3H); $^{13}$C-NMR (125 MHz, CDCl$_3$), δ 206.3, 171.9, 165.1, 159.1, 138.8, 138.6, 138.5, 137.8, 137.6, 133.0, 132.8, 132.3, 129.9, 129.9, 129.6, 129.6, 129.5, 129.5, 129.3, 129.2, 128.4, 128.3, 128.3, 128.3, 128.2, 128.0, 127.8, 127.5, 127.4, 113.6, 104.0, 86.64, 82.06, 79.49, 76.82, 76.67, 75.08, 74.56, 73.49, 73.40, 73.24, 73.09, 70.42, 69.42, 68.57, 68.48, 67.05, 55.10, 38.14, 29.68, 28.13, 21.00; HRMS (M+Cs) calcd for C$_{67}$H$_{70}$O$_{14}$SCs 1263.3541. found 1263.3604.

p-Methylphenyl 2-O-(2,3,4-Tri-O-benzyl-α-L-fucopyranosyl)-6-O-t-butyldiphenylsilyl-4-O-levulinyl-1-thio-β-D-galactopyranoside (31):

Compound 31 was prepared from 39 (100 mg) as described for the preparation of 25, yielding 31 (89 mg, 99%) as syrup: $^1$H-NMR (500 MHz, CDCl$_3$), δ 7.64 (t, J=7.5 Hz, 4H), 7.22–7.43 (m, 23H), 7.00 (d, J=8.0 Hz, 2H), 5.50 (d, J=3.0 Hz, 1H), 4.97 (d, J=3.0 Hz, 1H), 4.96 (d, J=12.0 Hz, 1H), 4.86 (d, J=12.0 Hz, 1H), 4.78 (d, J=12.0 Hz, 1H), 4.75 (s, 2H), 4.66 (d, J=12.0 Hz, 1H), 4.64 (d, J=2.5 Hz, 1H), 4.52 (d, J=9.5 Hz, 1H), 4.28 (q, J=6.5 Hz, 1H), 4.04–4.09 (m, 1H), 3.97 (dd, J=10.0, 2.5 Hz, 1H), 3.83 (dt, J=9.0, 2.5 Hz, 1H), 3.63–3.75 (m, 4H), 3.57 (t, J=9.0 Hz, 1H), 2.58–2.70 (m, 2H), 2.51 (t, J=7.0 Hz, 2H), 2.29 (s, 3H), 2.12 (s, 3H), 1.20 (d, J=6.5 Hz, 3H), 1.03 (s, 9H); $^{13}$C-NMR (125 MHz, CDCl$_3$), δ 206.3, 171.8, 138.5, 138.4, 137.4, 137.3, 135.6, 133.2, 133.1, 132.3, 129.9, 129.7, 129.6, 129.5, 128.6, 128.4, 128.3, 128.2, 128.0, 127.7, 127.7, 127.6, 127.4, 101.2, 86.6, 79.97, 79.80, 77.76, 77.38, 75.83, 74.73, 74.66, 74.17, 72.52, 69.44, 67.33, 62.08, 38.14, 29.78, 28.05, 26.74, 21.07, 19.10, 16.43; HRMS (M+Cs) calcd for C$_{61}$H$_{70}$O$_{11}$SSiCs 1171.3462. found 1171.3423.

p-Methylphenyl 2-O-Benzoyl-4-O-(2,3,4-tri-O-benzyl-α-L-fucopyranosyl)-6-O-t-butyldiphenylsilyl-1-thio-β-D-galactopyranoside (32):

Compound 32 was prepared from 41 (48 mg) as described for the preparation of 25, yielding 32 (26.3 mg, 61%): $^1$H-NMR (500 MHz, CDCl$_3$), δ 8.12 (dd, J=8.0, 1.0 Hz, 2H), 7.65–7.68 (m, 4H), 7.57 (tt, J=7.5, 1.0 Hz, 1H), 7.16–7.49 (m, 25H), 6.90 (d, J=8.0 Hz, 2H), 5.33 (t, J=10.0 Hz, 1H), 5.02 (d, J=11.5 Hz, 1H), 4.93 (t, J=12.5 Hz, 2H), 4.84 (d, J=11.5 Hz, 1H), 4.76 (d, J=12.0 Hz, 1H), 4.70 (d, J=3.5 Hz, 1H), 4.67 (d, J=12.0 Hz, 1H), 4.66 (d, J=10.0 Hz, 1H), 4.65 (d, J=11.5 Hz, 1H), 4.00 (dd, J=10.5, 3.5 Hz, 1H), 3.95 (d, J=3.0 Hz, 1H), 3.73–3.84 (m, 4H), 3.56–3.62 (m, 2H), 3.47 (d, J=1.5 Hz, 1H), 2.19 (s, 3H), 1.01 (s, 9H), 0.79 (d, J=6.5 Hz, 3H); $^{13}$C-NMR (125 MHz, CDCl$_3$), δ 165.5, 138.6, 138.4, 137.5, 137.2, 135.6, 133.7, 133.2, 132.8, 130.4, 129.9, 129.7, 129.2, 128.8, 128.5, 128.4, 128.4, 128.4, 128.2, 128.1, 127.9, 127.7, 127.6, 102.0, 85.7, 80.98, 79.70, 79.25, 77.38, 76.35, 74.67, 74.36, 74.19, 73.14, 71.84, 67.30, 62.86, 29.65, 26.78, 21.10, 16.21; HRMS (M+Cs) calcd for C$_{63}$H$_{68}$O$_{10}$SSiCs 1177.3357. found 1177.3397.

p-Methylphenyl 2,3-Di-O-benzoyl-4,6-O-benzylidine-1-thio-β-D-galactopyranoside (33):

p-Methylphenyl 4,6-O-benzylidine-1-thio-β-D-galactopyranoside (1.0 g, 2.67 mmol) was treated with BzCl (2 mL)-pyridine (3 mL) in CH$_2$Cl$_2$ (10 mL). Chromatography (Hexane/AcOEt, 1:1) of the residue gave 33 (1.48 g, 95%); [α]$_D$22 +34° (c, 0.5, CHCl$_3$); $^1$H-NMR (500 MHz, CDCl$_3$), δ 5.76 (t, 1H, J=10.0 Hz, H-2), 5.49 (s, 1H, ArCH), 5.34 (dd, 1H, J=3.5 and 10.0 Hz, H-3), 4.902 (d, 1H, J=10.0 Hz, H-1), 4.57 (d, 1H, J=3.0 Hz, H-4), 4.44, 4.08 (dd, 1H each, J=1.5 and 12.5 Hz, H-6), 3.75 (s, 1H, H-5), 2.34 (s, 3H, -Me); HRMS (M+Cs) calcd for C$_{34}$H$_{30}$O$_7$SCs 715.0767. found 715.0792. Anal. Calcd for C$_{34}$H$_{30}$O$_7$S: C, 70.09; H, 5.19; S, 5.50. Found: C, 70.05; H, 5.02; S, 6.06.

p-Methylphenyl 4,6-O-Benzylidine-2-O-chloroacetyl-1-thio-β-D-galactopyranoside (34):

To the solution of the p-methylphenyl 4,6-O-benzylidine-1-thio-β-D-galactopyranoside (2.5 g, 6.68 mmol), DCC (1.65 g, 8.0 mmol) and DMAP (200 mg) in CH$_2$Cl$_2$ (40 mL), was added levulinic acid (770 μL, 7.35 mmoL). The mixture was stirred at rt. for 3 h, then pyridine (2.5 mL) and chloroacetylchloride (537 μL, 13.36 mmol) were added. After stirring for overnight, the mixture was diluted with CH$_2$Cl$_2$ (150 mL), washed with water, 10% H$_2$SO$_4$, water, sat. aq. NaHCO$_3$, dried over Na$_2$SO$_4$, filtered and concentrated. The residue was chromatographed (Hexane/AcOEt, 2:1 to 1:1) to give p-methylphenyl 4,6-O-benzylidine-2-O-chloroacetyl-3-O-levulinyl-1-thio-β-D-galactopyranoside (1.32 g, 36%) which was treated with NH$_2$NH$_2$ (1 mL)-AcOH(2 mL) in THF-MeOH(10:1, 10 mL). The residue was concentrated, diluted with CH$_2$Cl$_2$ (150 mL), washed with sat. aq NaHCO$_3$, dried (Na$_2$SO$_4$), filtered and concentrated. Chromatography of the residue gave 34 (1.03 g, 95%) as white white solid: [α]$_D$22 −17.6° (c, 0.5, CHCl$_3$); $^1$H-NMR (400 MHz, CDCl$_3$), δ 7.50–7.10 (9H), 5.47 (s, 1H, ArCH), 5.01 (t, 1H, J=9.64 Hz, H-2), 4.579 (d, 1H, J=9.76 Hz, H-1), 4.36 (dd, 1H, J=1.48 and 12.48 Hz, H-6), 4.17 (dd, 1H, J=1.0 and 3.64 Hz, H-4), 4.14 (s, 2H, CH$_2$Cl), 3.73 Bs, 1H, H-3), 3.51 (d, 1H, J=1.08 Hz, H-5), 2.66 (bs, 1H, OH), 2.35 (s, 3H, Me); $^{13}$C-NMR (500 MHz, CDCl$_3$), δ 166.41, 138.53, 137.20, 101.39, 84.29, 75.45, 72.32, 71.76, 69.75, 68.98, 40.84, 21.21; HRMS (M+Cs) calcd for C$_{22}$H$_{23}$O$_6$ClSCs 473.0802. found 473.0817.

p-Methylphenyl 2-O-Benzoyl-6-O-t-butyldiphenylsilyl-4-O-levulinyl-3-O-p-methoxybenzyl-1-thio-β-D-galactopyranoside (35):

Compound 45 (1.97 g, 2.65 mmol) was treated with pyridine (50 mL) and benzoyl chloride (1.2 mL, 10.6 mmol). The residue was subjected to a column chromatography on silica gel (hexanes/EtOAc 4:1) to give 35 (2.24 g, 100%) as a syrup: $^1$H-NMR (500 MHz, CDCl$_3$), δ 7.98 (d, J=8.0 Hz, 2H), 7.65–7.68 (m, 4H), 7.60 (t, J=7.5 Hz, 1H), 7.37–7.48 (m, 8H), 7.32 (d, J=8.0 Hz, 2H), 7.01 (d, J=9.0 Hz, 2H), 6.99 (d, J=8.0 Hz, 2H), 6.59–6.62 (m, 2H), 5.66 (d, J=3.0 Hz, 1H), 5.31 (t, J=10.0 Hz, 1H), 4.68 (d, J=10.0 Hz, 1H), 4.54 (d, J=12.5 Hz, 1H), 4.33 (d, J=12.5 Hz, 1H), 3.80–3.85 (m, 1H), 3.68–3.73 (m, 5H), 3.62 (dd, J=9.5, 3.0 Hz, 1H), 2.55–2.73 (m, 4H), 2.27 (s, 3H), 2.13 (s, 3H), 1.07 (s, 9H); $^{13}$C-NMR (125 MHz, CDCl$_3$), δ 206.1, 171.8, 165.1, 159.1, 137.9, 135.6, 135.6, 133.1, 133.0, 132.9, 129.9, 129.9, 129.8, 129.8, 129.6, 129.5, 129.3, 129.2, 128.3, 127.8, 127.7, 113.5, 87.0, 77.67, 76.87, 70.35, 69.62, 66.16, 61.99, 55.11, 38.18, 29.75, 28.18, 26.74, 21.08, 19.12; HRMS (M+Cs) calcd for C$_{49}$H$_{54}$O$_9$SSiCs 979.2312. found 979.2349.

p-Methylphenyl 2-O-Benzoyl-4-O-levulinyl-3-O-p-methoxybenzyl-1-thio-β-D-galactopyranoside (36):

A mixture of 35 (330 mg, 0.39 mmol), HF-pyridine complex (3.5 mL), acetic acid (5.0 mL), and dry THF (25 mL) was stirred for 11 h under argon. The reaction mixture was diluted with EtOAc (150 mL), then washed with saturated aq. NaHCO$_3$ (3×30 mL) and brine (30 mL), dried over Na$_2$SO$_4$. Filtered and concentrated under reduced pressure. The residue was purified by chromatography on a silica gel column (hexanes-EtOAc 1:1.5) to yield 36 (237 mg, 100%) as a syrup: $^1$HNMR (500 MHz, CDCl$_3$), δ 7.99 (dd, J=8.5, 1.0 Hz, 2H), 7.61 (t, J=7.0, 1.0 Hz, 1H), 7.47 (t, J=8.0 Hz, 2H), 7.32–7.34 (m, 2H), 7.06 (d, J=8.0 Hz, 2H), 7.00 (d, J=9.0 Hz, 2H), 6.59–6.62 (m, 2H), 5.53 (d, J=3.0 Hz, 1H), 5.38 (t, J=10.0 Hz, 1H), 4.70 (d, J=10.0 Hz, 1H), 4.53 (d, J=12.0 Hz, 1H), 4.31 (d, J=12.5 Hz, 1H), 3.77–3.80 (m, 1H), 3.71 (s, 3H), 3.62–3.70 (m, 2H), 2.82–2.89 (m, 1H), 2.67–2.74 (m, 2H), 2.57–2.64 (m, 2H), 2.30 (s, 3H), 2.19 (s, 3H), 2.04 (d, J=0.5 Hz, 1H); $^{13}$C-NMR (125 MHz, CDCl$_3$), δ 206.9, 173.1, 165.1, 159.2, 138.1, 133.1, 129.9, 129.5, 129.1, 128.8, 128.2, 113.6, 86.86, 77.40, 76.64, 70.37, 69.67, 66.62, 60.51, 55.08, 38.00, 29.70, 28.01, 21.02; HRMS (M+Cs) calcd for C$_{33}$H$_{36}$O$_9$SCs 741.1134. found 741.1155.

p-Methylphenyl 3-O-Benzyl-4,6-O-benzylidine-2-O-levulinyl-1-thio-β-D-galactopyranoside (37):

p-methylphenyl 3-O-benzyl-4,6-O-benzylidine-1-thio-β-D-galactopyranoside (300 mg, 0.646 mmol) in CH$_2$Cl$_2$ (5 mL) were treated with levulinic acid (120 μL, 0.97 mmol), DCC (200 mg) and DMAP (50 mg) by the procedure described for the preparation of 34. The residue was purified by column chromatography (Hexane/AcOEt, 1:1) to give 37 (345 mg, 95%) as white solid: [α]$_D$22 −2.6° (c, 0.5, CHCl$_3$); $^1$HNMR (500 MHz, CDCl$_3$), δ 7.49–7.03 (m, 14 H), 5.42 (s, 1H), 5.26 (t, 1H, J=10.0 Hz, H-2), 4.65, 4.61 (d, each 1H, J=12.5 Hz), 4.573 (d, 1H, J=9.5 Hz, H-1), 4.33 (d, 1H, J=12.0 Hz), 4.14 (d, 1H, J=3.5 Hz), 3.97 (d, 1H, J=$^J$2.0 Hz), 3.60 (dd, 1H, J=10.0 and 3.5 Hz), 3.41 (s, 1H), 2.77, 2.62 (m, 2H each), 2.32, 2.19 (s, 3H each); 13C-NMR (125 MHz, CDCl3), δ 206.4, 171.7, 138.1, 138.0, 137.6, 101.2, 85.3, 78.4, 73.2, 71.2, 69.9, 69.2, 68.6, 37.9, 29.9, 28.1, 21.2; HRMS (M+Cs) calcd for C$_{32}$H$_{34}$O$_7$SCs 695.1080. found 695.1054.

p-Methylphenyl 2,3-Di-O-acetyl-6-O-benzyl-1-thio-β-D-galactopyranoside (38).

p-Methylphenyl 4,6-O-benzylidine-1-thio-β-D-galactopyranoside (200 mg, 0.437 mmol) was treated with Ac$_2$O-pyridine (1:2, 3 mL) as described for the preparation of 12. Flash chromatography (Hexanes/AcOEt 1:1) of the residue gave p-methylphenyl 2,3-di-O-acetyl-4,6-O-benzylidine-1-thio-β-D-galactopyranoside (358 mg, 97%). One part of the product (200 mg, 0.437 mmol) was mixed with MS. 3A (300 mg) and NaCNBH$_3$ (155 mg, 2.19 mmol) in THF (2 mL), and 1M HCl-Et$_2$O solution was added until no more gas was coming out. The mixture was diluted with CH$_2$Cl$_2$ (20 mL) and filtered through Celite, washed with brine, dried (Na$_2$SO$_4$), filtered and concentrated. Chromatography (hexanes-AcOEt, 1:1) of the residue gave 38 (184 mg, 92%) as white solid: [α]$_D$22 +7° (c, 0.5, CHCl$_3$); $^1$H-NMR (500 MHz, CDCl$_3$), δ 41–7.05 (9H), 5.27 (t, 1H, J=9.5 Hz, H-2), 4.95 (dd, 1H, J=3.0 and 9.5 Hz, H-3), 4.625 (d, 1H, J=10.0 Hz, H-1), 4.55 (ABq, 2H, J=12.0 Hz, ArCH2), 4.16 (bs, 1H, H-4), 3.77 (m, 2H, H-6), 3.70 (t, 1H, J=5.0 Hz, H-5), 2.74 (d, 1H, J=3.5 Hz, OH), 2.30, 2.08, 2.06 (s, 3H each, Me); HRMS (M+Na) calcd for C$_{24}$H$_{28}$O$_7$SNa 483.1453. found 483.1465.

p-Methylphenyl 2-O-(2,3,4-Tri-O-benzyl-α-L-fucopyranosyl)-6-O-t-butyldiphenylsilyl-4-O-levulinyl-3-O-p-methoxybenzyl-1-thio-β-D-galactopyranoside (39):

To a mixture of 45 (300 mg, 0.404 mmol), 50 (327 mg, 0.606 mmol), and 4 Å molecular sieves (800 mg) in CH$_2$Cl$_2$ (8 mL), NIS (143 mg, 0.606 mmol) was added under argon. After stirring for 20 min at −20° C., TfOH (65 (L, 0.3M in Et$_2$O) was added at −20° C. and the reaction mixture was stirred for 20 min. Et$_3$N (1.0 mL) was then added. The reaction mixture was filtered through celite, and the filtrate was diluted with CH$_2$Cl$_2$. The solution was washed with sat. aq. Na$_2$S$_2$O$_5$, sat. NaHCO$_3$, and brine, dried over Na$_2$SO$_4$ and concentrated. The residue was purified by column chromatography on silica gel (hexanes/EtOAc 4:1) to give 39 (343 mg, 73%): $^1$H-NMR (500 MHz, CDCl$_3$), δ 7.60–7.63 (m, 4H), 7.19–7.43 (m, 23H), 7.06 (d, J=9.0 Hz, 2H), 7.01 (d, J=8.0 Hz, 2H), 6.76–6.80 (m, 2H), 5.76 (d, J=4.0 Hz, 1H), 5.63 (d, J=3.0 Hz, 1H), 4.94 (d, J=11.5 Hz, 1H), 4.79 (d, J=11.5 Hz, 1H), 4.74 (d, J=10.0 Hz, 1H), 4.72 (d, J=11.5 Hz, 1H), 4.58–4.69 (m, 5H), 4.26 (d, J=10.5 Hz, 1H), 3.97–4.07 (m, 3H), 3.76 (s, 3H), 3.71–3.75 (m, 3H), 3.59–3.65 (m, 2H), 2.49–2.56 (m, 4H), 2.29 (s, 3H), 2.07 (s, 3H), 1.14 (d, J=6.5 Hz, 3H), 1.02 (s, 9H); $^{13}$C-NMR (100 MHz, CDCl$_3$), δ 171.73, 158.91, 138.76, 138.61, 138.43, 137.23, 135.61, 135.55, 133.17, 132.94, 131.56, 130.42, 129.76, 129.67, 129.58, 128.68, 128.35, 128.29, 128.14, 128.10, 127.70, 127.67, 127.51, 127.40, 127.33, 113.60, 97.57, 87.52, 82.57, 79.47, 77.71, 77.10, 75.55, 74.68, 73.14, 72.81, 71.53, 70.25, 67.37, 65.95, 62.00, 55.22, 38.13, 29.74, 28.08, 26.72, 21.04, 19.06, 16.58; HIS (M+Cs) calcd for C$_{69}$H$_{78}$O$_{12}$SSiCs 1291.4038. found 1291.4100.

p-Methylphenyl 2-O-(2,3,4-Tri-O-benzyl-α-L-fucopyranosyl)-4-O-levulinyl-3-O-p-methoxybenzyl-1-thio-β-D-galactopyranoside (40):

Compound 40 was prepared from 39 (86.0 mg) as described for the preparation of 36, yielding 40 (62.6 mg, 92%): $^1$H-NMR (500 MHz, CDCl$_3$), δ 7.18–7.37 (m, 17H), 7.09 (d, J=8.0 Hz, 2H), 7.04 (d, J=8.5 Hz, 2H), 6.78 (d, J=8.5 Hz, 2H), 5.76 (d, J=4.0 Hz, 1H), 5.45 (d, J=3.5 Hz, 1H), 4.94 (d, J=11.5 Hz, 1H), 4.80 (d, J=11.5 Hz, 1H), 4.76 (d, J=10.0 Hz, 1H), 4.73 (d, J=11.5 Hz, 1H), 4.58–4.68 (m, 4H), 4.55 (d, J=10.5 Hz, 1H), 4.27 (d, J=10.5 Hz, 1H), 4.05–4.09 (m, 3H), 4.00 (dd, J=10.0, 2.5 Hz, 1H), 3.82 (dd, J=9.0, 3.5 Hz, 1H), 3.77 (s, 3H), 3.73 (br. s, 1H), 3.67 (dd, J=11.5, 6.5 Hz, 1H), 3.59 (t, J=6.5 Hz, 1H), 3.51 (dd, J=11.0, 6.5 Hz, 1H), 2.59–2.75 (m, 3H), 2.50–2.56 (m, 1H), 2.32 (s, 3H), 2.13 (s, 3H), 1.17 (d, J=6.5 Hz, 3H); $^{13}$C-NMR (125 MHz, CDCl$_3$), δ 206.4, 173.2, 159.0, 138.7, 138.6, 138.3, 137.6, 132.0, 129.8, 129.6, 129.5, 128.5, 128.3, 128.2, 128.1, 128.1, 127.7, 127.5, 127.4, 127.4, 113.6, 97.6, 87.08, 82.10, 79.42, 77.66, 76.75, 75.51, 74.68, 73.15, 72.82, 71.79, 70.13, 67.40, 66.41, 60.53, 55.20, 37.93, 29.70, 27.92, 21.04, 16.58; HRMS (M+Cs) calcd for C$_{53}$H$_{60}$O$_{12}$SCs 1053.2860. found 1053.2830.

p-Methylphenyl 2-O-Benzoyl-4-O-(2,3,4-tri-O-benzyl-α-L-fucopyranosyl)-6-O-t-butyldiphenylsilyl-3-O-p-methoxybenzyl-1-thio-β-D-galactopyranoside (41):

Compound 41 was prepared from 44 (311 mg) and 50 (337 mg) as described for the preparation of 39, yielding 41 (356 mg, 74%): $^1$H-NMR (500 MHz, CDCl$_3$), δ 8.02 (dd, J=8.0, 1.0 Hz, 2H), 7.69 (dd, J=8.0, 1.0 Hz, 2), 7.63 (dd, J=8.0, 1.5 Hz, 2H), 7.59 (t, J=7.5 Hz, 1H), 7.17–7.48 (m, 25H), 6.98 (t, J=8.5 Hz, 4H), 6.63 (d, J=8.5 Hz, 2H), 5.76 (t, J=9.5 Hz, 1H), 5.57 (d, J=4.0 Hz, 1H), 4.92 (d, J=12.0 Hz, 1H), 4.87 (d, J=11.5 Hz, 1H), 4.77 (d, J=12.0 Hz, 2H), 4.67 (d, J=12.0 Hz, 1H), 4.56 (d, J=11.5 Hz, 1H), 4.49 (d, J=11.5 Hz, 1H), 4.44 (d, J=12.5 Hz, 1H), 4.39 (d, J=11.5 Hz, 1H), 4.21 (d, J=2.0 Hz, 1H), 3.96 (dd, J=11.0, 7.5 Hz, 1H), 3.89 (dd, J=10.5, 4.0 Hz, 1H), 3.63–3.77 (m, 7H), 3.44 (q, J=6.5 Hz, 1H), 3.34 (d, J=2.0 Hz, 1H), 2.21 (s, 3H), 1.07 (s, 9H), 0.74 (d, J=6.5 Hz, 3H); $^{13}$C-NMR (125 MHz, CDCl$_3$), δ 164.9, 159.2, 139.4, 139.0, 138.6, 137.0, 135.7, 135.5, 133.4, 133.0, 132.9, 131.6, 130.9, 130.3, 129.8, 129.7, 129.6, 129.5, 129.3, 128.6, 128.3, 128.2, 128.1, 128.1, 127.9, 127.7, 127.5, 127.5, 127.2, 126.8, 113.7, 96.6, 87.8, 81.27, 80.23, 78.32, 77.51, 77.21, 75.12, 74.50, 73.61, 71.83, 71.46, 70.32, 69.22, 66.63, 64.76, 55.15, 26.84, 21.04, 16.54; HRMS (M+Cs) calcd for C$_{71}$H$_{76}$O$_{11}$SSiCs 1297.3932. found 1297.3995.

p-Methylphenyl 2-O-Benzoyl-4,6-O-benzylidine-1-thio-β-D-galactopyranoside (42):

p-methylphenyl 4,6-O-benzylidine-1-thio-β-D-galactopyranoside (300 mg, 0.802 mmol) in CH$_2$Cl$_2$ (10 mL) was treated with DCC (238 mg, 1.16 mmol) DMAP (50 mg) and levulinic acid (100 µL, 0.963 mmol) as described for the preparation of 34. The residue was treated with pyridine (500 µL) and BzCl (400 µL) under reflux condition. After workup, the residue was chromatographed (Hexane/AcOEt, 2:1 to 1:1) to give p-Methylphenyl 2-O-benzoyl-4,6-O-benzylidine-3-O-levulinyl-1-thio-β-D-galactopyranoside (226 mg, 49%), which was treated with NH$_2$NH$_2$(100 µL)-AcOH(200 µL) in THF-MeOH(10:1, 5 mL). The residue was concentrated, diluted with CH$_2$Cl$_2$ (150 mL), washed with sat. aq NaHCO$_3$, dried (Na$_2$SO$_4$), filtered and concentrated. Chromatography of the residue gave 42 (185 mg, 99%): 1H-NMR (500 MHz, CDCl$_3$), δ 7.50–7.10 (14H), 5.52 (s, 1H, ArCH), 5.20 (t, 1H, J=9.5 Hz, H-2), 4.760 (d, 1H, J=10.0 Hz, H-1), 4.40 (dd, 1H, J=1.5 and 12.5 Hz, H-6), 4.24 (bd, 1H, J=3.5 Hz, H-4), 4.04 (dd, 1H, J=1.5 and 12.5 Hz, H-6), 3.87 (ddd, 1H, J=3.0 and 9.5 Hz, H-3) 3.59 (bs, 1H, H-5), 2.62 (d, 1H, J=11.0 Hz, OH), 2.35 (s, 3H, Me); $^{13}$C-NMR (500 MHz, CDCl$_3$), δ 165.96, 101.44, 84.80, 75.60, 72.90, 70.67, 69.88, 69.10, 21.21; HRMS (M+Na) calcd for C$_{27}$H$_{26}$O$_6$SNa 501.1348. found 501.1364.

p-Methylphenyl 2-O-benzoyl-6-O-t-butyldiphenylsilyl-3-O-p-methoxybenzyl-1-thio-β-D-galactopyranoside (44):

To a stirred solution of 35 (420 mg, 0.496 mmol) in THF-MeOH (10:1 v/v, 22 mL), 1M NH$_2$NH$_2$—AcOH (1:2.5 v/v) in THF-MeOH (5:1 v/v) (5 mL) was added. The reaction mixture was stirred for 4 h, then evaporated until dryness. The residue was diluted with EtOAc (80 mL), washed with saturated aq. NaHCO$_3$ and brine, and dried over Na$_2$SO$_4$. The dried organic layer was concentrated under reduced pressure, and the residue was purified by chromatography on a silica gel column (hexanes-EtOAc 4:1) to give 44 (343 mg, 92%) as solids: $^1$H-NMR (500 MHz, CDCl$_3$), δ 8.01 (dd, J=8.0, 1.0 Hz, 2H), 7.68–7.71 (m, 4H), 7.60 (t, J=7.0, 1.5 Hz, 1H), 7.36–7.48 (m, 8H), 7.33 (d, J=8.0 Hz, 2H), 7.07 (d, J=8.5 Hz, 2H), 6.99 (d, J= 8.0 Hz, 2H), 6.67 (d, J=9.0 Hz, 2H), 5.43 (t, J=10.0 Hz, 1H), 4.67 (d, J=10.0 Hz, 1H), 4.57 (d, J=12.0 Hz, 1H), 4.45 (d, J=12.0 Hz, 1H), 4.12 (br. S, 1H), 3.94–4.00 (m, 2H), 3.71 (s, 3H), 3.61 (dd, J=9.0, 3.0 Hz, 1H), 3.56 (t, J=6.0 Hz, 1H), 2.54 (d, J=1.0 Hz, 1H), 2.27 (s, 3H), 1.07 (s, 9H); $^{13}$C-NMR (125 MHz, CDCl$_3$), δ 165.2, 159.3, 137.7, 135.6, 135.6, 133.2, 133.2, 133.0, 132.6, 130.1, 129.9, 129.7, 129.5, 129.5, 129.3, 128.3, 127.7, 113.8, 87.06, 79.02, 78.75, 71.01, 69.85, 66.30, 63.15, 55.12, 26.81, 21.08, 19.19; HRMS (M+Cs) calcd for C$_{44}$H$_{48}$O$_7$SSiCs 881.1944. found 881.1976.

p-Methylphenyl 6-O-t-Butyldiphenylsilyl-4-O-levulinyl-3-O-p-methoxybenzyl-1-thio-β-D-galactopyranoside (45):

A mixture of p-Methylphenyl 2-O-chloroacetyl-3-O-p-methoxybenzyl-4-O-levulinyl-6-O-t-butyldiphenylsilyl-1-thio-β-D-galactopyranoside (ibid, Wong, C.-H. et al 1998) (550 mg, 0.672 mmol), saturated NaHCO$_3$ in MeOH—H$_2$O (5:1 v/v) solution (50 mL), and THF (12 mL) was stirred for 6 h at 60° C. The solvent was then removed under reduced pressure and the residue was diluted with EtOAc (150 mL) and water (30 mL). The organic layer was separated and the aqueous layer was extracted with EtOAc (2×25 mL). The organic fractions were combined and washed with brine and dried over Na$_2$SO$_4$. The dried organic layer was concentrated, and the residue was purified by chromatography on a silica gel column (hexanes-EtOAc 3:1) to yield 45 (498 mg, 100%) as a syrup: $^1$H-NMR (500 MHz, CDCl$_3$), δ 7.63–7.66 (m, 4H), 7.36–7.45 (m, 8H), 7.26 (d, J=8.5 Hz, 2H), 7.04 (d, J=8.0 Hz, 2H), 6.87 (d, J=8.5 Hz, 2H), 5.63 (d, J=3.0 Hz, 1H), 4.71 (d, J=11.0 Hz, 1H), 4.46 (d, J=9.5 Hz, 1H), 4.40 (d, J=11.0 Hz, 1H), 3.79 (s, 3H), 3.78 (dd, J=12.5, 9.0 Hz, 1H), 3.64–3.68 (m, 2H), 3.62 (dt, J=1.5, 9.5 Hz, 1H), 3.44 (dd, J=9.0, 3.0 Hz, 1H), 2.50–2.67 (m, 4H), 2.42 (d, J=1.5 Hz, 1H), 2.30 (s, 3H), 2:12 (s, 3H), 1.05 (s, 9H); $^{13}$C-NMR (125 MHz, CDCl$_3$), δ 205.9, 171.7, 159.4, 138.1, 135.6, 135.6, 133.1, 133.0, 129.9, 129.8, 129.8, 129.6, 129.4, 128.2, 127.7, 113.9, 88.4, 79.83, 77.58, 71.17, 68.38, 66.21, 61.89, 55.25, 38.06, 29.79, 28.02, 26.74, 21.10, 19.10; HRMS (M+Cs) calcd for C$_{42}$H$_{50}$O$_8$SSiCs 875.2050. found 875.2082.

p-Methylphenyl 2,3-Di-O-benzyl-4,6-O-benzylidine-1-thio-β-D-galactopyranoside (46) and p-methylphenyl 2-O-Benzyl-4,6-O-benzylidine-1-thio-β-D-galactopyranoside (49):

To a mixture of p-Methylphenyl 4,6-O-benzylidine-1-thio-β-D-galactopyranoside (2.0 g, 5.35 mmol) and BnBr (1.08 mL, 6.42 mmol) in a mixture of CH$_2$Cl$_2$ (75 mL) and 1.0 M aq. NaOH (27 mL), was added Bu$_4$N—HSO$_4$ (367 mg, 1.07 mmol). The mixture was stirred vigorously for 20 h under reflux, then diluted with CH$_2$Cl$_2$ (100 mL), washed with brine, dried over Na$_2$SO$_4$, filtered and concentrated. Chromatography (Hexanes/AcOEt, 5:1 to 1:1) of the residue gave dibenzylated 46 (170 mg 6%) as syrup; [α]$_D$22 −23° (c, 0.5, CHCl$_3$); $^1$H-NMR (500 MHz, CDCl$_3$), δ 5.48 (s, 1H, ArCH), 4.72 (m, 4H, ArCH$_2$), 4.577 (d, 1H, J=9.50 Hz, H-1), 4.37 (dd, 1H, J=1.5 and 12.0 Hz, H-6), 4.14 (d, 1H, J=3.5 Hz, H-4), 3.98 (dd, 1H, J=1.5 and 12.5 Hz, H-6), 3.85 (t, 1H, J=9.5 Hz, H-2), 3.63 (dd, 1H, J=3.5 and 9.5 Hz, H-3), 3.40 (Bs, 1H, H-5), 3.51 (d, 1H, J=1.08 Hz, H-5), 2.31 (s, 3H, Me); $^{13}$C-NMR (500 MHz, CDCl$_3$), δ 138.5, 138.1, 137.9, 137.6, 133.4, 101.3, 86.5, 81.4, 75.4, 75.3, 73.6, 71.8, 69.7, 69.4, 21.1; p-Methylphenyl 3-O-Benzyl-4,6-O-benzylidine-1-thio-β-D-galactopyranoside (1.10 g, 44.7%): $^1$H-NMR (500 MHz, CDCl$_3$), δ 5.39 (s, 1H, ArCH), 4.68 (m, 2H, ArCH$_2$), 4.435 (d, 1H, J=9.5 Hz, H-1), 4.30 (dd, 1H, J=1.0 and 12.5 Hz, H-6), 4.09 (d, 1H, J=3.5 Hz, H-4), 3.92 (dd, 1H, J=1.5 and 12.5 Hz, H-6), 3.85 (t, 1H, J=9.5 Hz, H-2), 3.47 (dd, 1H, J=3.5 and 9.5 Hz, H-3), 3.38 (Bs, 1H, H-5), 2.31 (s, 3H, Me); $^{13}$C-NMR (500 MHz, CDCl$_3$), δ 101.0, 87.0, 80.1, 73.2, 71.5, 69.9, 69.3, 67.0, 21.2; HRMS (M+Na) calcd for C$_{27}$H$_{28}$O$_5$SCs 597.0712. found 597.0728; and 49 (780 mg, 31.4%) as syrup: $^1$H-NMR (500 MHz, CDCl$_3$), δ 5.51 (s, 1H, ArCH), 4.77 and 4.67 (d, 1H each, ArCH$_2$), 4.541 (d, 1H, J=9.9 Hz, H-1), 4.34 (bd, 1H, J=12.0 Hz, H-6), 4.12 (d, 1H, J=3.5 Hz, H-4), 3.97 (bd, 1H, J=12.5 Hz, H-6), 3.60 (t, 1H, J=9.0 Hz, H-2), 3.75 (bs, 1H, H-3), 3.40 (Bs, 1H, H-5), 2.60 (bs, 1H, OH), 2.33 (s, 3H, Me); $^{13}$C-NMR (500 MHz, CDCl$_3$), δ 101.3, 86.3, 77.0, 75.7, 75.2, 74.2, 69.6, 69.2, 21.1; HRMS (M+Cs) calcd for C$_{27}$H$_{28}$O$_5$SCs 597.0712. found 597.0727.

p-Methylphenyl 2-O-(2,3,4-tri-O-benzyl-α-L-fucopyranosyl)-6-O-t-butyldiphenylsilyl-3-O-p-methoxybenzyl-1-thio-β-D-galactopyranoside (47):

Compound 47 was prepared from 39 (73.0 mg) as described for the preparation of 44, yielding 47 (57.3 mg, 86%): $^1$H-NMR (500 MHz, CDCl$_3$), δ 7.63–7.65 (m, 4H), 7.22–7.41 (m, 23H), 7.13 (d, J=8.5 Hz, 2H), 7.00 (d, J=8.0 Hz, 2H), 6.80 (d, J=8.5 Hz, 2H), 5.75 (d, J=3.5 Hz, 1H), 4.95 (d, J=12.0 Hz, 1H), 4.80 (d, J=11.5 Hz, 1H), 4.65–4.77 (m, 5H), 4.60 (q, J=6.5 Hz, 1H), 4.53 (d, J=11.5 Hz, 1H), 4.43 (d, J=11.5 Hz, 1H), 4.01–4.12 (m, 4H), 3.83–3.89 (m, 2H), 3.76 (s, 3H), 3.67–3.73 (m, 2H), 3.45 (t, J=6.0 Hz, 1H), 2.36 (br. s, 1H), 2.28 (s, 3H), 1.14 (d, J=6.0 Hz, 3H), 1.02 (s, 9H); $^{13}$C-NMR (125 MHz, CDCl$_3$), δ 159.2, 138.8, 138.6, 138.5, 137.0, 135.6, 135.5, 135.5, 133.2, 133.1, 131.4, 130.7, 129.7, 129.6, 129.5, 129.3, 128.7, 128.4, 128.3, 128.1, 127.8, 127.7, 127.5, 127.4, 113.9, 97.6, 87.34, 84.24, 79.59, 78.00, 77.66, 75.70, 74.66, 73.37, 72.78, 71.55, 70.38, 67.31, 65.54, 63.04, 55.19, 29.66, 26.76, 21.04, 16.55; HRM (M+Cs) calcd for C$_{64}$H$_{72}$O$_{10}$SSiCs 1193.3670. found 1193.3613.

p-Methylphenyl 2,3,4,6-Tetra-O-benzyl-1-thio-β-D-galactopyranoside (48):

p-Methylphenyl 1-thio-β-D-galactopyranoside (1.0 g, 3.5 mmol) was dissolved in dry DMF (15 mL) and cooled to −10° C. At this temperature (840 mg, 35 mmol) NaH was added and the mixture allowed to warm up to rt. and stirred for an additional 10 min. Then BnBr (4.1 mL, 35 mmol) was added, and the mixture was stirred for 5 h. At 0° C. 10 mL H$_2$O was added and the mixture extracted with EtOAc (3×50 mL). The organic layer was dried over MgSO$_4$ and evaporated to dryness. Flash chromatography using Hexane/EtOAc (5:1) gave the title compound as a white solid (2.01 g, 89%). [α]$_D$22 −1.2° (c, 0.5, CHCl$_3$); $^1$H-NMR (400 MHz, CDCl$_3$), δ 2.27 (s, 3H), 3.56–3.65 (m, 4H), 3.89 (t, 1H, J=9.4 Hz) 3.97 (s, 1H), 4.42 (AB$_q$, 2H, J=11.6 Hz), 4.59–4.60 (m, 3H), 4.70 (m, 3H), 4.73 (AB$_q$, 2H, J=10.1 Hz), 4.95 (d, 1H, J=11.5 Hz), 6.98 (d, 2H, J=8.6 Hz), 7.25–7.47 (m, 22H); $^{13}$C-NMR (400 MHz, CDCl$_3$), δ 21.04, 68.68, 72.63, 73.48, 74.34, 75.54, 77.16, 77.24, 84.13, 87.95, 127.36, 127.49, 127.60, 127.65, 127.71, 127.78, 127.86, 128.09, 128.26, 128.35, 129.49, 132.10; HRMS (M+Cs) calcd for C$_{41}$H$_{42}$O$_5$SCs 779.1807. found 779.1782.

p-Methylphenyl 2,3,4-Tri-O-benzyl-1-thio-β-L-fucopyranoside (50):

p-Methylphenyl 2,3,4-Tri-O-acetyl-1-thio-β-L-fucopyranoside (ibid, Brukart, M. D. et al. 1997) (2.5 g, 6.31 mmol) was treated with NaOMe-MeOH. The product was further treated with 85% NaH (463 mg, 22.7 mmol) and BnBr (5.8 mL, 37.86 mmol) in DMF (25 mL). After reaction was finished, hexane (30 mL) and water (300 mL) were added into the vigorously stirred solution. The solid product was filtered, washed with water (2×5 mL) and hexane-AcOEt (15:1, 2×5 mL). The crude product was suspended in a hot (70° C.) mixture of AcOEt-Hexane (10:1), and stirred for 10 min, cooled to rt, filtered to gave pure 50 (2.6 g, 76%) as solid: [α]$_D$22 +8° (c, 0.5, CHCl$_3$); HRMS (M+Cs) calcd for C$_{34}$H$_{36}$O$_4$SCs 672.1290. found 672.1287.

Methyl 2,3-Di-O-acetyl-6-O-benzyl-4-O-[2,4,6-tri-O-benzoyl-3-O-(2,3,4,6-tetra-O-benzyl-α-D-galactopyranosyl)-β-D-galactopyranosyl]-α-D-glucopyranoside (52):

A mixture of 48 (37.5 mg, 0.052 mmol), 19 (24 mg, 0.039 mmol) and MS-AW-300 (400 mg) in CH$_2$Cl$_2$ (2 mL) was stirred at 0 C for 15 min, then NIS (13.5 mg, 0.057 mmol) was added followed by 0.5 M TfOH in Et$_2$O (10 μL, 0.005 mmol). After 30 min a solution of 51 (36 mg, 0.080 mmol) in CH$_2$Cl$_2$ (0.5 mL) and MS AW-300 (100 mg) was added followed by NIS (13.5 mg, 0.057 mmol). The mixture was stirred for 2 h at rt, then solid Na$_2$S$_2$O$_3$, NaHCO$_3$ and two drops of H$_2$O were added and stirred for 5 min, diluted with CH$_2$Cl$_2$ (25 mL), filtered through Celite, washed with brine, dried (Na$_2$SO$_4$), filtered and concentrated. Chromatography (hexanes-AcOEt, 2:1 to 1:1) of the residue gave 52 (35.9 mg, 64%) as syrup: $^1$H-NMR (400 MHz, CDCl$_3$), δ 5.80 (d, 1H, J=3.1 Hz), 5.56 (dd, 1H, J=8.4 and 10.1 Hz), 5.48 (d, 1H, J=9.8 Hz), 5.09 (d, 1H, J=3.2 Hz), 4.86 (d, 1H, J=3.6 Hz), 4.79 (dd, 1H, J=3.7 and 10.4 Hz), 4.69 (d, 1H, J=11.4 Hz), 4.60 (d, 1H, J=8.1 Hz), 4.58 (d, 1H, J=12.0 Hz), 3.95 (m, 2H), 3.85 (dd, 1H, J=3.2 Hz), 3.81–3.74 (m, 2H), 3.69 (m, 2H), 3.28 (s, 3H), 2.05, 1.96 (s, 3H each); $^{13}$C-NMR (500 MHz, CDCl$_3$), δ 170.3, 169.7, 166.1, 165.8, 164.3, 243.6, 243.3, 243.0, 138.8, 138.6, 138.2, 138.1, 100.7, 96.9, 95.6, 78.8, 75.1, 75.0, 74.5, 74.3, 73.4, 73.3, 73.1, 72.5, 71.5, 71.4, 71.3, 70.0, 69.9, 69.7, 68.9, 67.6, 86.6, 62.3, 20.9, 20.7; HRMS (M+Cs) calcd for C$_{79}$H$_{80}$O$_{21}$Cs 1497.4246. found 1497.4362.

Methyl 2,3-Di-O-acetyl-6-O-benzyl-4-O-[2,3,4-tri-O-benzoyl-60-(3,4,6-tri-O-acetyl-2-deoxy-2-(2,2,2,-trichloroethoxylcarbonylamino)-β-D-glucopyranosyl)-β-D-galactopyranosyl]-α-D-glucopyranoside (53):

A mixture of 21 (70 mg, 0.12 mmol), 13 (48 mg, 0.08 mmol) and MS-AW-300 (400 mg) in CH$_2$Cl$_2$ (2 mL) was stirred at 0 C for 15 min, then NIS (30.5 mg, 0.132 mmol) was added followed by 0.1 M solution of TfOH (5 μL) in Et$_2$O. After 15 min a solution of 51 (72 mg, 0.16 mmol) in CH$_2$Cl$_2$ (0.5 mL) and MS AW-300 (100 mg) were added followed by NIS (33 mg, 0.13 mmol). The mixture was stirred for 1 h followed by workup as described in the preparation of 52. Chromatography (hexanes-AcOEt, 3:2 to 1:1) of the residue gave 53 (62.5 mg, 60%) as white white solid: $^1$H-NMR (500 MHz, CDCl$_3$), δ 5.80 (d, 1H, J=3.1 Hz), 5.77 (d, 1H, J=8.2 Hz), 5.56 (dd, 1H, J=8.2 and 10.0 Hz), 5.42 (t, 1H, J=10.0 Hz), 5.34 (bt, 1H, J=9.4 Hz), 5.25 (dd, 1H, J=3.2 and 10.3 Hz), 5.0 (m, 3H), 4.87 (d, 1H, J=3.5 Hz), 4.75 (d, 1H, J=12.5 Hz), 4.70 (d, 1H, J=8.3 Hz), 4.38 (d, 1H, J=12.5 Hz). 3.31 (s, 3H), 2.07, 2.06 (s, 3H each), 2.01 (s, 9H); 13C-NMR (500 MHz, CDCl3), δ 170.6, 170.4, 169.6, 169.5, 165.4, 165.3, 164.6, 133.6, 133.3, 133.2, 100.7, 100.1, 97.1, 74.3, 74.2, 73.6, 72.5, 72.0, 71.8, 71.6, 70.8, 70.7, 70.0, 69.6, 68.6, 68.2, 67.6, 67.1, 61.8; 56.2, 55.3, 31.6, 29.7, 29.6, 22.63, 21.22, 20.8, 20.6; HRMS (M+Cs) calcd for C$_{60}$H$_{64}$O$_{25}$NSiCs 1436.1887. found 1436.1824.

Methyl 2,3-Di-O-acetyl-6-O-benzyl-4-O-[2-O-benzyl-4,6-O-benzylidine-3-O-(2,3,4-tri-O-benzyl-α-L-fucopyranosyl)-α-D-galactopyranosyl]-α-D-glucopyranoside (54):

To a cold (0° C.) solution of compound 50 (32 mg, 0.6 mmol), compound 49 (19 mg, 0.04 mmol), 2,6-dit-butyl-4-methylpyridine (25 mg, 0.12 mmol) and MS-AW-300 (300 mg) in CH$_2$Cl$_2$ (2 mL) was added freshly prepared 1M DMTST in CH$_2$Cl$_2$ (120 μL, 0.12 mmol). After 1 h, a solution of methyl 2,3-di-O-acetyl-6-O-benzyl-α-D-glucopyranosideside 51 (36 mg, 0.08 mmol) in CH$_2$Cl$_2$ (0.5 mL) and MS AW-300 (100 mg) was added followed by adding 1M DMTST (120 μL, 0.12 mmol). The mixture was stirred for 2 h, then diluted with CH$_2$Cl$_2$ (25 mL), filtered through Celite, washed with satd.aq. NaHCO$_3$, dried (Na$_2$SO$_4$), filtered and concentrated. The residue was chromatographed (hexanes-AcOEt, 3:1 to 1:1) to give 54 (28.4 mg, 63%) as syrup: $^1$H-NMR (500 MHz, CDCl$_3$), δ 5.53 (t, 1H, J=9.5 Hz), 5.33 (s, 1H), 5.32 (d, 1H, J=3.0 Hz), 5.14 (d, 1H, J=3.5 Hz), 4.92–4.49 (m, 12H), 4.28 (dd, 1H, J=3.0 and 10.0 Hz), 4.10 (t, 1H, J=9.5 Hz), 3.87 (dd, 1H, J=3.0 and 10.0 Hz), 3.72 (bt, 1H, J=12.5 Hz), 3.39 (s, 3H), 2.07, 2.06 (s, 3H each), 0.97 (d, 1H J=6.5 Hz); HRMS (M+Cs) calcd for C65H72O17Cs 1257.3824. found 1257.3870.

Methyl 2,3-Di-O-acetyl-6-O-benzyl-4-O-{2,3,4-tri-O-benzoyl-6-O-[3,6-di-O-benzoyl-2-deoxy-2-(2,2,2,-trichloroethoxylcarbonylamino)-4-O-(2,3,4,6-tetra-O-benzyl-β-D-galactopyranosyl)-β-D-glucopyranosyl]-β-D-galactopyranosyl}-α-D-glucopyranoside (55):

A mixture of 48 (73 mg, 0.112 mmol), 27 (50 mg, 0.075 mmol) and MS-AW-300 (400 mg) in CH$_2$Cl$_2$ (3 mL) was stirred at −25° C. for 20 min, then NIS (27.8 mg, 0.118 mmol) was added followed by 1 M TfOH (10 μL, 0.001 mmol). After 20 min, 13 (68.8 mg, 0.112 mmol), MS AW-300 (100 mg) and NIS (18.6 mg, 0.079 mmol) were added. The mixture was stirred at 0° C. for 1 h, then a solution of 51 (250 μL of 125 mg/0.5 mL, 0.150 mmol) and NIS (40 mg, 0.169 mmol) was added and stirred for 50 min, worked up as described in the preparation of 52. Chromatography (hexanes-AcOEt, 3:2 to 1:1) of the residue gave 55 (56 mg, 39.2%) as syrup: $^1$H-NMR (500 MHz, CDCl$_3$), δ 5.80 (d, 1H, J=3.1 Hz), 5.59 (t, 1H, J=9.5 Hz), 5.52 (dd, 1H, J=8.2 and 10.0 Hz), 5.41 (t, 1H, J=9.1 Hz), 5.24 (dd, 1H, J=3.2 and 10.4 Hz), 5.03 (d, 1H, J=3.4 Hz), 5.25 (dd, 1H, J=3.2 and 10.3 Hz), 4.94 (dd, 1H, J=3.5 and 10.0 Hz), 4.67 (d, 1H, J=7.9 Hz), 3.29 (s, 3H), 2.07, 2.02 (s, 3H each), 2.01 (s, 9H); HRMS (M+Cs) calcd for C$_{102}$H$_{102}$O$_{29}$NCl$_3$Cs 2042.4657. found 2042.

5-Methoxycarbonylpentyl 3-O-Benzyl-2-deoxy-6-O-p-methoxybenzyl-2-phthalimido-β-D-glucopyranoside (56):

The tittle compound was prepared via three-step:
1). 61b (16.0 g, 36.6 mmol) in dry acetonitrile (200 mL) was treated with anisaldehyde dimethyl acetyl (9.3 mL, 54.9 mmol) and 10-camphorsulfonic acid (173.5 mg) as described for the preparation of 5. The residue was subjected to a column chromatography on silica gel (hexanes/EtOAc 2:1) to give 5-Methoxycarbonylpentyl 2-deoxy-4,6-O-p-methoxybenzylidene-2-phthalimido-β-D-glucopyranoside (16.4 g, 81%) as solids: $^1$H-NMR (400 MHz, CDCl$_3$), δ 7.84–7.87 (m, 2H), 7.71–7.75 (m, 2H), 7.42 (d, J=8.7 Hz, 2H), 6.89 (d, J=8.8 Hz, 2H), 5.52 (s, 1H), 5.24 (d, J=8.5 Hz, 1H), 4.57–4.63 (m, 1H), 4.36 (dd, J=10.2, 4.3 Hz, 1H), 4.22 (dd, J=10.5, 8.5 Hz, 1H), 3.78–3.85 (m, 5H), 3.55–3.66 (m, 5H), 3.37–3.45 (m, 1H), 2.64 (d, J=3.5 Hz, 1H), 1.93–2.07 (m, 2H), 1.32–1.51 (m, 4H), 1.05–1.15 (m, 2H); $^{13}$CNMR (100 MHZ, CDCl$_3$), δ 173.86, 160.24, 134.13, 131.56, 129.40, 127.59, 123.42, 113.69, 101.83, 98.81, 82.19, 69.66, 68.62, 68.58, 66.09, 56.53, 55.27, 51.39, 33.67, 28.91, 25.24, 24.34; HRMS (M+Cs) calcd for C$_{29}$H$_{33}$O$_{10}$NCs 688.1159. found 688.1188.

2). A solution of the product (8.85 g, 15.9 mmol) form step (1) in dry DMF (40 mL), NaH (60%, 0.95 g, 23.8 mmol) was added in portions. After stirring for 10 min, benzyl bromide (2.9 mL, 23.8 mmol) and Bu$_4$NI (3.5 g, 9.5 mmol) were added at 0° C. The reaction mixture was stirred for 3 h at 0° C. then added MeOH (8 mL) and stirred for 10 min. The reaction mixture was poured to ice-water (200 mL) and extracted with EtOAc (3×150 mL). The combined organic liquid was dried over Na$_2$SO$_4$. The solvent was removed and the residue was subjected to a column chromatography on silica gel (hexanes/EtOAc 3:1) to give 5-Methoxycarbonylpentyl 3-O-benzyl-2-deoxy-4,6-O-p-methoxybenzylidene-2-phthalimido-β-D-glucopyranoside (5.56 g, 54%) as white solids: $^1$HNMR (500 MHz, CDCl$_3$), δ 7.66–7.85 (m, 4H), 7.45 (d, J=8.5 Hz, 2H), 7.00 (dd, J=8.0, 1.5 Hz, 2H), 6.86–6.94 (m, 5H), 5.58 (s, 1H), 5.18 (d, J=8.5 Hz, 1H), 4.78 (d, J=12.5 Hz, 1H), 4.49 (d, J=12.5 Hz, 1H), 4.40 (dd, J=10.5, 9.0 Hz, 1H), 4.38 (dd, J=10.5, 5.5 Hz, 1H), 4.20 (dd, J=10.5, 8.5 Hz, 1H), 3.74–3.86 (m, 6H), 3.58–3.67 (m, 4H), 3.38 (dt, J=9.5, 6.5 Hz, 1H), 1.92–2.03 (m, 2H), 1.33–1.44 (m, 4H), 1.03–1.12 (m, 2H); $^{13}$CNMR (125 MHz, CDCl$_3$), δ 173.8, 160.0, 137.9, 133.9, 131.6, 129.8, 128.0, 127.3, 123.3, 113.6, 101.3, 98.8, 83.05, 74.58, 74.02, 69.59, 68.73, 66.10, 55.81, 55.27, 51.44, 33.67, 28.91, 25.24, 24.35; HRMS (M+Cs) calcd for C$_{36}$H$_{39}$O$_{10}$NCs 778.1628. found 778.1652.

3). The product (2.7 g, 4.19 mmol) from setp 2 was mixed with NaCNBH$_3$ (1.38 g, 21 mmol), DMF (35 mL), and 3 Å molecular sieves (5.0 g), and a solution of trifluoroacetic acid (3.2 mL, 42 mmol) in DMF (25 mL) was added dropwise at 0° C. The reaction mixture was stirred for 1.5 h at 0° C., then 24 h at room temperature. After addition of further trifluoroacetic acid (3.0 mL) in DMF (20 mL), the reaction mixture was stirred for another 24 h at room temperature. The mixture was diluted with EtOAc (50 mL) and MeOH (5 mL), filtered through Celite, and the cake was washed with EtOAc (150 mL). The combined filtrates were washed with cold water (200 mL), cold sat. NaHCO$_3$ (200 mL), and brine (2×100 mL), dried over Na$_2$SO$_4$. The solvent was removed and the residue was purified by column chromatography on silica gel (hexanes/EtOAc 2:1) to give 56 (2.45 g, 90%) as an oil: $^1$H-NMR (500 MHz, CDCl$_3$), δ 7.68–7.81 (m, 4H), 7.28 (d, J=8.5 Hz, 2H), 7.04–7.06 (m, 2H), 6.92–6.96 (m, 3H), 6.89 (d, J=8.5 Hz, 2H), 5.12 (d, J=8.0 Hz, 1H), 4.75 (d, J=12.0 Hz, 1H), 4.57 (d, J=11.5 Hz, 1H), 4.53 (d, J=12.5 Hz, 1H), 4.51 (d, J=11.5 Hz, 1H), 4.21 (dd, J=11.0, 8.5 Hz, 1H), 4.13 (dd, J=11.0, 8.5 Hz, 1H), 3.81 (s, 3H), 3.73–3.82 (m, 4H), 3.60–3.64 (m, 1H), 3.59 (s, 3H), 3.35 (dt, J=9.5, 6.5 Hz, 1H), 3.07 (d, J=2.0 Hz, 1H), 1.91–2.02 (m, 2H), 1.32–1.45 (m, 4H), 1.01–1.12 (m, 2H); $^{13}$C-NMR (125 MHz, CDCl$_3$), δ 173.8, 159.3, 138.2, 133.7, 129.6, 129.4, 128.1, 127.8, 127.3, 113.9, 98.2, 78.55, 74.66, 74.20, 73.36, 73.36, 70.45, 69.18, 55.31, 55.20, 51.31, 33.60, 28.87, 25.17, 24.35; HRMS (M+Cs) calcd for C$_{36}$H$_{41}$O$_{10}$NCs 780.1785. found 780.1759.

5-Methoxycarbonylpentyl 4-O-[3-O-(2,3,4,6-Tetra-O-benzyl-α-D-galactopyranosyl)-4-O-(2,3,4-tri-O-benzyl-α-L-fucopyranosyl)-2-O-benzoyl-6-O-t-butyldiphenylsilyl-β-D-galactopyranosyl]-3-O-benzyl-2-deoxy-6-O-p-methoxybenzyl-2-phthalimido-β-D-glucopyranoside (57):

To a solution of the disaccharide 32 (15.0 mg, 0.01437 mmol) and the fucoside 50 (13.9 mg, 0.02155 mmol) in CH$_2$Cl$_2$ (2 mL) was added 4 Å molecular sieves (300 mg), and the mixture was stirred for 20 min at room temperature under argon. A fresh prepared solution of DMTST from methyl disulfide (8.2 mg, 86.2 μmol) and methyl trifluoromethanesulfonate (14.3 mg, 86.2 μmol) in CH$_2$Cl$_2$ (0.5 mL) was added to the above stirred mixture at 0° C., and the progress of the reaction was followed by TLC. The reaction mixture was stirred at 0° C. for 30 min and then at room temperature for 1 h, then a solution of compound 62 (27.9 mg, 0.04311 mmol) in CH$_2$Cl$_2$ (0.5 mL), NIS (5.1 mg, 0.02155 mmol), and TfOH (25 μL, 0.3 M etheral solution) were added. The reaction mixture was stirred for 30 min at room temperature, then quenched by adding Et$_3$N (0.8 mL), diluted with CH$_2$Cl$_2$, filtered. The organic phase was successively washed with saturated aqueous Na$_2$S$_2$O$_3$, NaHCO$_3$, and brine, dried over Na$_2$SO$_4$ and concentrated. The residue was purified by column chromatography on silica gel (hexanes/EtOAc 3:1 to 2:1) to give product 57 (17.2 mg, 57%) as a thick oil: $^1$H-NMR (500 MHz, CDCl$_3$), δ 8.00 (d, J=8.0 Hz, 2H), 7.08–7.77 (m, 46H), 6.96–6.97 (m, 4H), 6.81–6.85 (m, 6H), 6.76 (d, J=6.0 Hz, 2H), 6.64 (t, J=7.5 Hz, 1H), 6.55 (t, J=7.5 Hz, 2H), 5.98 (d, J=3.5 Hz, 1H), 5.90 (dd, J=10.0, 7.5 Hz, 1H), 5.28 (d, J=3.5 Hz, 1H), 4.94 (d, J=8.0 Hz, 1H), 4.88 (d, J=12.5 Hz, 1H), 4.83 (d, J=7.5 Hz, 1H), 4.81 (d, J=11.5 Hz, 1H), 4.78 (d, J=11.5 Hz, 1H), 4.64–4.71 (m, 2H), 4.59 (d, J=11.0 Hz, 1H), 4.55 (d, J=12.5 Hz, 1H), 4.54 (d, J=12.0 Hz, 1H), 4.45 (d, J=11.0 Hz, 2H), 4.43 (d, J=12.0 Hz, 1H), 4.27–4.36 (m, 6H), 4.17 (d, J=12.0 Hz, 1H), 3.98–4.09 (m, 5H), 3.93 (d, J=12.0 Hz, 1H), 3.85–3.90 (m, 2H), 3.73–3.80 (m, 5H), 3.57–3.68 (m, 5H), 3.56 (s, 3H), 3.51 (q, J=6.5 Hz, 1H), 3.36–3.42 (m, 3H), 3.19–3.27 (m, 4H), 1.84–1.96 (m, 2H), 1.25–1.35 (m, 4H), 1.10 (s, 9H), 0.95–1.03 (m, 2H), 0.90 (d, J=6.5 Hz, 3H); $^{13}$C-NMR (100 MHz, CDCl$_3$), δ 164.43, 159.11, 139.45, 139.42, 139.17, 138.78, 138.66, 138.51, 138.17, 137.88, 135.69, 135.48, 133.53, 133.47, 133.00, 130.40, 129.82, 129.74, 129.33, 128.70, 128.53, 128.45, 128.38, 128.33, 128.24, 128.19, 128.15, 128.00, 127.87, 127.74, 127.69, 127.66, 127.51, 127.48, 127.22, 126.84, 126.58, 113.71, 100.44, 98.15, 94.78, 94.29, 78.72, 78.28, 77.22, 77.17, 76.51, 75.59, 74.97, 74.83, 74.69, 74.65, 74.50, 74.22, 73.44, 73.34, 73.03, 72.84, 72.07, 71.46, 69.75, 69.06, 68.97, 67.90, 66.64, 64.92, 63.76, 55.74, 55.24, 51.35, 33.69, 29.70, 28.83, 27.02, 25.27, 24.37, 22.69, 19.25, 16.84, 14.13; HRMS (M+Cs) calcd for C$_{126}$H$_{135}$O$_{25}$NSiCs 2222.8147. found 2222.8294.

5-Methoxycarbonylpentyl 3,4,6-Tri-O-acetyl-2-deoxy-2-phthalimido-β-D-glucopyranoside (61a):

To a mixture of 60 (ibid, Nilsson, U. et al 1990) (30.0 g, 62.89 mmol) and methyl 6-hydroxylhexate (13.8 g, 94.3 mmol) in CH$_2$Cl$_2$ (550 mL), BF$_3$.OEt$_2$ (120 mL, 943 mmol) was added at 0° C. After the reaction mixture was stirred overnight, Water (15 mL) was added to the mixture. The mixture was diluted with CH$_2$Cl$_2$ (400 mL), washed with sat. NaHCO$_3$ (3×200 mL) and brine (200 mL), and dried over Na$_2$SO$_4$, filtered and concentrated. The residue was purified by column chromatography on silica gel (hexanes/EtOAc 2.5:1) to give 61a (26.0 g, 73%) as solid: $^1$H-NMR (500 MHz, CDCl$_3$), δ 7.84–7.89 (m, 2H), 7.73–7.77 (m, 2H), 5.79 (dd, J=10.5, 9.0 Hz, 1H), 5.36 (d, J=8.5 Hz, 1H), 5.18 (dd, J=10.0, 9.5 Hz, 1H), 4.34 (dd, J=12.0, 4.5 Hz, 1H), 4.31 (dd, J=10.5, 8.5 Hz, 1H), 4.18 (dd, J=12.5, 2.5 Hz, 1H), 3.81–3.89 (m, 2H), 3.61 (s, 3H), 3.44 (dt, J=10.0, 6.5 Hz, 1H), 2.12 (s, 3H), 2.04 (s, 3H), 1.97–2.07 (m, 2H), 1.87 (s, 3H), 1.37–1.51 (m, 4H), 1.04–1.18 (m, 2H); $^{13}$C-NMR (125 MHz, CDCl$_3$), δ 173.8, 170.7, 170.2, 169.5, 134.3, 131.3, 123.6, 98.10, 71.79, 70.74, 69.73, 68.97, 62.00, 54.59, 51.38, 33.67, 28.84, 25.20, 24.37, 20.75, 20.57, 20.44; HRMS (M+Na) calcd for C$_{27}$H$_{33}$O$_{12}$NNa 586.1900. found 586.1920.

5-Methoxycarbonylpentyl 2-Deoxy-2-phthalimido-β-D-glucopyranoside (61b):

Compound 61a (26.0 g, 46.18 mmol) was treated with NaOMe/MeOH (25 wt. %, 2.7 mL) in MeOH (200 mL) at room temperature. After 6 h, the mixture was neutralized (IRC-50 resin, weak acid) and concentrated to give product 61b (20.0 g, 99%) as semisolids: $^1$H-NMR (500 MHz, CDCl$_3$), δ 7.78–7.82 (m, 2H), 7.68–7.72 (m, 2H), 5.16 (d, J=8.5 Hz, 1H), 4.63 (d, J=4.5 Hz, 1H), 4.25–4.31 (m, 2H), 4.06 (dt, J=2.0, 8.5 Hz, 1H), 3.88–3.89 (m, 2H), 3.76 (dt, J=10.0, 6.5 Hz, 1H), 3.65–3.71 (m, 1H), 3.59 (s, 3H), 3.48 (t, J=6.5 Hz, 1H), 3.43 (dt, J=9.5, 3.5 Hz, 1H), 3.38 (dt, J=10.0, 6.5 Hz, 1H), 1.90–2.02 (m, 2H), 1.31–1.43 (m, 4H), 1.00–1.09 (m, 2H); $^{13}$CNMR (125 MHz, CDCl$_3$), δ 174.0, 168.4, 134.0, 131.6, 123.4, 98.31, 75.53, 71.53, 71.20, 69.43, 61.63, 56.66, 51.38, 33.65, 28.84, 25.18, 24.34; HRMS (M+Na) calcd for C$_{21}$H$_{27}$O$_9$NNa 460.1584. found 460.1598.

Mathematical Model

So as to be able to analyze the problem of designing optimal syntheses of oligosaccharides with a computer, it was necessary to quantify the relationship between yield and relative rate constants for donors in the database. A short treatment for this problem is shown below. It gives the mathematical relationship between yield under optimal conditions (no side reactions, 100% reaction with promoter, etc.) and the relative rate ratio between the two donors being considered for each individual step.

Relationship between Relative Rates and Substrate Consumption

Assumptions: Each competing reaction can be described by a second-order rate equation:

$$\partial A_1/\partial t = -k_1[A_1][E] \quad \partial A_2/\partial t = -k_2[A_2][E]$$

(i) Integrated Second-Order Rate Equation. Solving for [E] for one of them and substituting into the other, one obtains $$\partial A_1/[A_1] = (k_1/k_2)\partial A_2/[A_2]$$

This is then integrated over the bounds of the experiment:

$$\int_{[A_1]_0}^{[A_1]_t} \partial A_1/[A_1] = k_1/k_2 \int_{[A_2]_0}^{[A_2]_t} \partial A_2/[A_2]$$

$\ln [A_1]_t - \ln [A_1]_o = (k_1/k_2)(\ln [A_2]_t - \ln [A_2]_o)$

Finally, $$k_1/k_2 = (\ln [A_1]_t/[A_1]_o)/(\ln [A_2]_t/[A_2]_o) = \{(\ln [A_1]_t/[A_1]_o)\}/\{(\ln([A_2]_t)/[A_2]_o)\} \quad (1)$$

(ii) The Yield Equation. Assumptions: All reacting starting material goes to product:

$[A_1]_t/[A_1]_o = 1 - ([P]_t/[A_1]_o)([A_2]_t/[A_2]_o) = 1 - [Q]_t/[A_2]_o$

The two donors are present in equimolar concentrations:

$[A_1]_o = [A_2]_o$

The only detractor from yield is competition from the undesired donor:

yield$= [P]_t/[A_1]_o = 1 - [Q]_t/[A_2]_o$

Borrowing eq 1 for the relationship between rate constant ratios and consumption of starting material, we can quickly use it to predict the production of the two products P (desired) and Q (undersired).

$$k_1/k_2 = (\ln [A_1]_t/[A_1]_o)/(\ln [A_2]_t/[A_2]_o) = \ln(1-[P]_t/[A_1]_o)/\ln(1-[Q]_t/[A_2]_o) \quad (2)$$

Rearranging, we find that $\ln((1-[Q]_t/[A_2]_o)^{k_1/k_2}) = \ln(1-[P]_t/[A_2]_o)$ $(1-[Q]_t/[A_2]_o)^{k_1/k_2} = 1-[P]_t/[A_1]_o$ Finally, employing the simple yield relations listed in the assumptions above, this becomes $$(\text{yield})^{k_1/k_2} = 1 - \text{yield} \quad (3)$$

Figure 20:
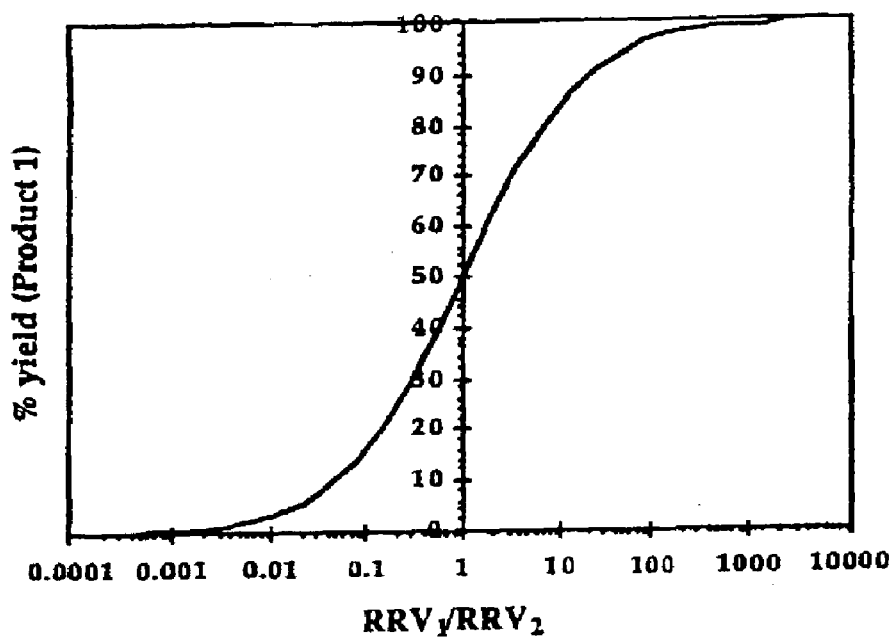
FIG. 20 illustrates a picture of the OptiMer program in operation. In the background on the left is a FileMaker Pro database which contains the donor library. Upon hitting the "Run Research" button, OptiMer launches and then presents the user with a dialongue box requesting the target oligosaccharide sequence (foreground). The results appear in the remainaing window as a list of donor sequence "hits" accompanied by optimum yield calculations, and then a list of the frequency of donor appearance at each step from the top 100 hits (for use with large libraries). The chemist may opt to either take one of the best sequences found or select from the list of best donors at each position to design his own sequence on the basis of knowledge of donor availability or other desired properties.

This is not directly solvable for yield. However, a computer can find the solution through a number of approaches involving iterative solution. Persons without access to a computer may simply refer to FIG. 20 for the solution to this equation, which is possible to draw because eq 3 may be solved for $k_1/k_2$.

Optimer:

In order to search the library of donors for the combination of donors which produces the best possible yield, a computer program, OptiMer, was constructed using C/C++ using Metrowerks CodeWarrior Professional Release 3 to run on Macintosh PowerPC computers to identify sets of available donors which best satisfy the yield calculation shown in equation 2 above. The program interfaces with a database of donors stored using the FileMaker Pro 4.0. When the user signals his readiness to run a search, the C++ program loads the database and searches it to identify the 100 best sets of available characterized oligosaccharide donors. For large sequences, a "Monte Carlo" search method is also available, which simply picks combinations at random. The frequency with which each donor appears at each step in the list of the best 100 donor sets is tabulated and the user is presented with a list of donors at each step which tend to give the highest overall yields. The user is then free to make an educated choice as to which donors to use based on availability, cost and donor reactivity.

One potential limitation of this approach stems from the extremely dense information capacity inherent in the carbohydrate code (Laine, R. A. *Pure & Appl. Chem.* 1997, 69, 1867). This manifests itself as an extremely rapid increase in the computational burden with increasing library size and increasing number of monomer units in the oligomer. As a result, the following optimizations were made to the search logic: The program only checks donors for a reaction step which have a donor reactivity less than or equal to the reactivity of the donor used in the previous step. As a result, the program will return no result in which the reactivities of the donors do not decrease (or stay the same) over the course of the multi-step reaction. In addition, the program (when not in "Monte Carlo" mode) checks the sequences in order of decreasing reactivity for the donor used in step one. If the program finds that a particular donor at step one yields no "hits" for all combinations of donors for steps which follow it, the program will not examine less reactive step one donors. This can be done because a more reactive step one donor will always give a better estimated yield than a slower one, provided the reactivities of the other donors are kept constant. For large libraries which are well represented for all values for most donors, there is an intelligent search option which further restricts the search at each step to the range of values around the expected optimal reactivity.

For a hexasaccharide search using a library with two hundred random donors with reactivities ranging from 1 to 10000 available for each step, the normal set of optimizations reduce the number of sequences needed to be scanned from 320 billion to approximately 70 million (a factor of 4500). (The intelligent search further accelerates it by a factor of 3 or 4.) Given that current desktop computers manage about 200 million CPU clock cycles per second, searching the full sequence space even at one CPU cycle per sequence would require 15 minutes of search time. (The real number of cycles per sequence is orders of magnitude larger than that.)

OptiMer calculates the stepwise yield by a minimization of an error function which is based on the yield equation (3). This error function should have its minimum for values of yield and $k_1/k_2$ which best satisfy Equation (3), and it should always be positive, with a minimum of zero for 0<yield<1 (100%):

error=(yield$^{k_1/k_2}$+yield−1)$^2$

An initial guess as to the correct yield value was obtained using a simpler stepwise yield equation which assumes first order kinetics [yield=$k_1/(k_1+k_2)$]. This value was optimized by picking two yield values which are somewhat higher and lower than the original value, and evaluating the error function for all three yield values. This provided three points (yield vs. error for the given $k_1/k_2$) with which to calculate a parabolic approximation of the error function (error=A+B(yield)+C (yield$^2$). From this, a better estimate for the yield can be directly obtained, based on the minimum of the parabolic function (minimum=−B/2 C). This was performed in an iterative fashion, in the process narrowing the bracketing outlying points and optimizing the yield value until the yield value had converged to stepwise changes of less than 0.00001%. The yield values so obtained were checked against equation 3 (which can be solved for $k_1/k_2$) and were found to deviate from the expected value by no more than ±0.001% over the range $10^{-6} < k_1/k_2 < 10^6$. Past this range, the yield is expected to be extremely close to 0% ($k_1/k_2 < 10^{-6}$) and 100% ($k_1/k_2 > 10^6$). Errors outside the tested range are expected to influence the overall yield calculation insignificantly, since the yield behaves asymptotically in these areas. The stepwise yield are multiplied together to obtain a overall calculated yield for the set of donors if the overall yield is large enough to be included in the list of top hits, the set of donors is stored for later output to the user.

Typical experimental procedures for the synthesis of building blocks:

(1) p-Methylphenyl 2-deoxy-2-phthalimido-3-O-benzoyl-4,6-O-benzylidene-1-thio-β-D-glucopyranoside:

To a cold (0° C.) mixture of p-methylphenyl 2-deoxy-2-phthalimido-4,6-O-benzylidene-1-thio-β-D-glucopyranoside (150 g, 2.98 mmol) and pyridine (50 mL) was added benzoyl chloride (1.38 mL, 11.92 mmol). The mixture was then stirred overnight and concentrated. The residue was subjected to a column chromatography on silica gel (hexanes/EtOAc 3:1 to 2:1) to give product (1.81 g, 100%) as a colorless foam: $^1$H NMR (500 MHz, CDCl$_3$) δ 7.65–7.88 (m, 6H), 7.47 (t, J=7.4 Hz, 1H), 7.28–7.41 (m, 9H), 7.09 (d, J=7.9 Hz, 2H), 6.18 (t, J=9.4 Hz, 1H), 5.83 (d, J=10.6 Hz, 1H), 5.55 (s, 1H), 4.52 (t, J=10.3 Hz, 1H), 4.43–4.48 (m, 1H), 3.83–3.92 (m, 3H), 2.32 (s, 3H); $^{13}$C NMR (125 MHz, CDCl3) δ 167.87, 167.10, 165.59, 138.67, 136.77, 134.27, 134.11, 133.61, 133.11, 131.58, 131.16, 129.76, 129.13, 129.03, 128.25, 128.16, 127.31, 126.15, 123.69, 123.60, 101.52, 84.29, 79.40, 70.95, 70.62, 68.60, 54.29, 21.18; HRMS (M+Na) calcd for C$_{35}$H$_{29}$O$_7$NSNa 630.1562. found 630.1571.

(2) p-Methylphenyl 2-deoxy-2-phthalimido-3-O-benzoyl-6-O-benzyl-1-thio-β-D-glucopyranoside:

To a mixture of p-methylphenyl 2-deoxy-2-phthalimido-3-O-benzoyl-4,6-O-benzylidene-1-thio-β-D-glucopyranoside (290 mg, 0.4778 mmol) and sodium cyanoborohydride (395 mg, 5.97 mmol) in THF (25 mL, distilled from Na) containing 3 Å molecular sieves (2.0 g), hydrogen chloride in diethyl ether (1.0 M solution, ~6 mL) was added until the evolution of gas ceased. After stirring for 20 min, the reaction mixture was diluted with CH$_2$Cl$_2$ (30 mL) and filtered through Celite. The filtrate was 133.48, 129.90, 129.81, 128.47, 123.67, 83.37, 79.78, 75.64, 70.55, 6250, 53.53, 21.17; HRMS (M+Na) calcd for C$_{28}$H$_{25}$O$_7$NSNa 542.1249. found 542.1259.

(4) p-Methylphenyl 2-deoxy-2-phthalimido-3-O-benzoyl-6O-t-butyldiphenylsilyl-1-thio-β-D-glucopyranoside:

A mixture of p-methylphenyl 2-deoxy-2-phthalimido-3-O-benzoyl-1-thio-β-D-glucopyranoside (70.0 mg, 0.1349 mmol), tert-butylchlorodiphenylsilane (83.2 mg, 0.2968 mmol), and imidazole (27.8 mg, 0.4047 mmol) in DMF (4 mL) was stirred for 4 h. The mixture was diluted with EtOAc (35 mL) and washed with water (3×10 mL). The organic layer was dried over Na$_2$SO$_4$ and concentrated. The residue was purified by column chromatography on silica gel (hexanes/EtOAc 4:1 to 3:1) to give product (82.0 mg, 80%) as a thick oil: $^1$H NMR (500 MHz, CDCl$_3$) δ 7.85 (dd, J=83, 1.1 Hz, 2H), 7.80 (d, J=6.4 Hz, 1H), 7.73–7.77 (m, 5H), 7.60–7.66 (m, 2H), 7.28–7.47 (m, 11H), 7.00 (d, J=8.1 Hz, 2H), 5.93 (dd, J=10.3, 8.9 Hz, 1H), 5.77 (d, J=10.4 Hz, 1H), 4.47 (t, J=10.3 Hz, 1H), 4.01–4.09 (m, 2H), 3.97 (t, J=9.3 Hz, 1H), 3.78 (dt, J=9.6, 4.3 Hz, 1H), 3.18 (br. s, 1H), 2.28 (s, 3H), 1.09 (s, 9H); $^{13}$C NMR (125 MHz, CDCl$_3$) δ 167.88, 167.17, 166.84, 138.14, 135.65, 135.60, 134.17, 134.04, 133.30, 133.26, 132.95, 132.91, 131.55, 131.21, 129.84, 129.77, 129.61, 128.90, 128.30, 127.79, 127.76, 123.54, 123.50, 83.29, 79.76, 75.38, 71.05, 64.12, 53.54, 26.80, 21.10, 19.22; HRMS (M+Na) calcd for C$_{44}$H$_{43}$O$_7$NSSiNa 780.2427, found 780.2460 washed with H$_2$O (15 mL), sat. NaHCO$_3$ (15 mL), and brine (10 mL). The organic layer was dried (Na$_2$SO$_4$) and concentrated. The residue was subjected to column chromatography (hexanes/EtOAc 3:1) to give product (280 mg, 96%) as a foam: $^1$H NMR (500 MHz, CDCl$_3$) δ 7.86 (dd, J=8.4, 1.0 Hz, 2H), 7.82 (d, J=6.4 Hz, 1H), 7.75 (d, J=6.3 Hz, 1H), 7.65–7.69 (m, 2H), 7.48 (t, J=75 Hz, 1H), 7.28–7.37 (m, 9H), 7.03 (d, J=7.7 Hz, 2H), 5.90 (dd, J=10.2, 8.8 Hz, 1H), 5.73 (d, J=10.4 Hz, 1H), 4.58–4.65 (ABq, J=11.9 Hz, 2H), 4.48 (t, J=10.4 Hz, 1H), 3.81–3.95 (m, 4H), 3.15 (d, J=3.7 Hz, 1H), 2.29 (s, 3H); $^{13}$C NMR (125 MHz, CDCl$_3$) δ 167.86, 167.20, 166.86, 138.38, 137.86, 134.22, 134.11, 133.49, 133.38, 131.59, 131.27, 129.88, 129.66, 128.90, 128.43, 128.37, 127.77, 127.72, 123.58, 83.47, 78.71, 75.27, 73.72, 71.41, 70.10, 53.54, 21.14; HRMS (M+Na) calcd for C$_{35}$H$_{31}$O$_7$NSNa 632.1719. found 632.1747.

(3) p-Methylphenyl 2-deoxy-2-phthalimido-3-O-benzoyl-1-thio-β-D-glucopyranoside:

p-Methylphenyl 2-deoxy-2-phthalimido-3-O-benzoyl-4,6O-benzylidene-1-thio-β-D-glucopyranoside (530 mg, 0.873 mmol) was dissolved in aqueous trifluoroacetic acid (10 mL, 80%), and the mixture was kept at 55° C. overnight and then concentrated and co-concentrated with toluene. The residue was chromatographed (silica gel, hexanes/EtOAc 3:1 to 1:1) to give product (387 mg, 85%) as solids: $^1$H NMR (400 MHz, CDCl$_3$) δ 7.68–7.88 (m, 6H), 7.51 (t, J=7.4 Hz, 1H), 7.35 (t, J=7.8 Hz, 2H), 7.29 (d, J=8.1 Hz, 2H), 7.08 (d, J=7.9 Hz, 2H), 5.87 (dd, J=10.2, 8.9 Hz, 1H), 5.75 (d, J=10.5 Hz, 1H), 4.48 (t, J=10.4 Hz, 1H), 4.02 (dd, J=12.0, 3.2 Hz, 1H), 3.87–3.94 (m, 2H), 3.70–3.75 (m, 1H), 2.32 (s, 3H); $^{13}$C NMR (100 MHz, CDCl$_3$) δ 167.23, 138.68, 134.33, 134.31, 133.61,

What is claimed is:

1. A fully protected mannoside possessing the following structure:

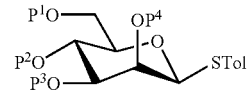

wherein $P^1$ and $P^2$ may make up a 1,3-diol protecting group possessing the following structure:

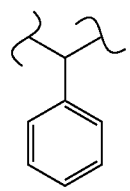

or $P^1$ and $P^2$ may be independently selected from the following group of radicals: -TBS, TBDPS, -Bn, -PMB, -Bz, ClAc-, -Lev; and wherein P³ and P⁴ may make up a 1,2-diol protecting group having the following structure:

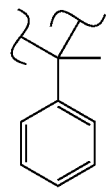

or alternatively, P³ and P⁴ are independently selected from the group of radicals consisting of -TBS, -Bn, -PMB, -Bz, and -Lev;

wherein -PMB is para-methoxybenzyl, -Lev is levulinyl, and -STol is p-methylphenylthio; -TBS is tert-butyldimethylsilyl; and -TBDPS is tert-butyl-diphenylsilyl.

2. A fully protected mannoside according to claim 1 possessing the following structure:

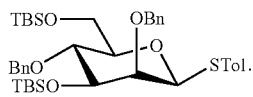

3. A fully protected mannoside according to claim 1 possessing the following structure:

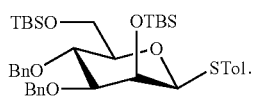

4. A fully protected mannoside according to claim 1 possessing the following structure:

5. A fully protected mannoside according to claim 1 possessing the following structure:

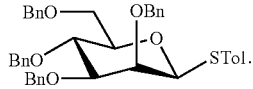

6. A fully protected mannoside according to claim 1 possessing the following structure:

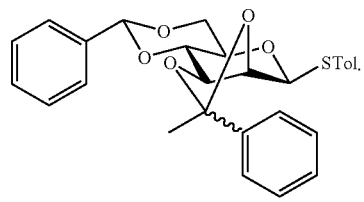

7. A fully protected mannoside according to claim 1 possessing the following structure:

8. A fully protected mannoside according to claim 1 possessing the following structure:

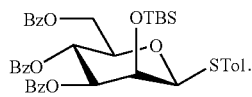

9. A fully protected mannoside according to claim 1 possessing the following structure:

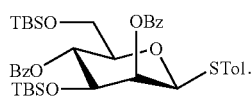

10. A fully protected mannoside according to claim 1 possessing the following structure:

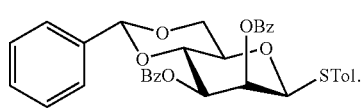

11. A fully protected mannoside according to claim 1 possessing the following structure:

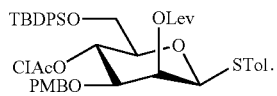

12. A fully protected mannoside according to claim 1 possessing the following structure:

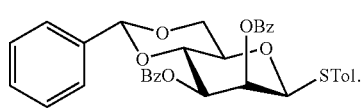

* * * * *